(12) United States Patent
Choudhary et al.

(10) Patent No.: US 12,049,528 B2
(45) Date of Patent: Jul. 30, 2024

(54) PHOTOPOLYMERIZABLE BLOCK POLYMERS AND METHODS OF PRODUCING AND USING THE SAME

(71) Applicant: Align Technology, Inc., San Jose, CA (US)

(72) Inventors: Umesh Upendra Choudhary, Santa Cruz, CA (US); Jessica Kalay Su, San Jose, CA (US); Michael Christopher Cole, San Jose, CA (US); Jennifer Marie Chavez, Santa Clara, CA (US)

(73) Assignee: ALIGN TECHNOLOGY, INC., San Jose, CA (US)

( * ) Notice: Subject to any disclaimer, the term of this patent is extended or adjusted under 35 U.S.C. 154(b) by 0 days.

(21) Appl. No.: 17/728,900

(22) Filed: Apr. 25, 2022

(65) Prior Publication Data
US 2022/0363792 A1 Nov. 17, 2022

Related U.S. Application Data

(60) Provisional application No. 63/179,004, filed on Apr. 23, 2021, provisional application No. 63/179,007, filed on Apr. 23, 2021.

(51) Int. Cl.
| | |
|---|---|
| *C08F 2/46* | (2006.01) |
| *C08F 2/50* | (2006.01) |
| *C08F 220/12* | (2006.01) |
| *C08F 220/30* | (2006.01) |
| *C08G 61/04* | (2006.01) |
| *A61C 7/00* | (2006.01) |
| *B33Y 70/00* | (2020.01) |
| *B33Y 80/00* | (2015.01) |

(52) U.S. Cl.
CPC .............. *C08F 220/12* (2013.01); *C08F 2/50* (2013.01); *C08F 220/301* (2020.02); *C08F 220/302* (2020.02); *A61C 7/00* (2013.01); *B33Y 70/00* (2014.12); *B33Y 80/00* (2014.12)

(58) Field of Classification Search
CPC ............ C08F 220/1806; C08F 220/301; C08F 220/1805; C08F 220/1811; C08F 220/12; C08F 293/005; C08F 226/06; C08F 8/12; C08F 2/50; C08F 2810/30; C08F 2810/40; C08F 2438/03; C08F 2438/01; C07C 69/86; C07C 69/54; C07C 2601/08; C07C 2601/14; A61C 7/002; A61C 7/08; A61C 7/00; A61K 6/887; C08L 33/04; B33Y 70/00; B33Y 80/00
USPC ........... 522/161, 155, 50, 6, 189, 184, 71, 1; 520/1
See application file for complete search history.

(56) References Cited

U.S. PATENT DOCUMENTS

| | | |
|---|---|---|
| 5,820,368 A | 10/1998 | Wolk |
| 6,183,248 B1 | 2/2001 | Chishti et al. |
| 6,309,215 B1 | 10/2001 | Phan et al. |
| 6,386,864 B1 | 5/2002 | Kuo |
| 6,454,565 B2 | 9/2002 | Phan et al. |
| 6,471,511 B1 | 10/2002 | Chishti et al. |
| 6,524,101 B1 | 2/2003 | Phan et al. |
| 6,572,372 B1 | 6/2003 | Phan et al. |
| 6,607,382 B1 | 8/2003 | Kuo et al. |
| 6,705,863 B2 | 3/2004 | Phan et al. |
| 6,783,604 B2 | 8/2004 | Tricca |
| 6,790,035 B2 | 9/2004 | Tricca et al. |
| 6,814,574 B2 | 11/2004 | Abolfathi et al. |
| 6,830,450 B2 | 12/2004 | Knopp et al. |
| 6,947,038 B1 | 9/2005 | Anh et al. |
| 7,074,039 B2 | 7/2006 | Kopelman et al. |
| 7,104,792 B2 | 9/2006 | Taub et al. |
| 7,121,825 B2 | 10/2006 | Chishti et al. |
| 7,160,107 B2 | 1/2007 | Kopelman et al. |
| 7,192,273 B2 | 3/2007 | McSurdy, Jr. |
| 7,347,688 B2 | 3/2008 | Kopelman et al. |
| 7,354,270 B2 | 4/2008 | Abolfathi et al. |
| 7,448,514 B2 | 11/2008 | Wen |
| 7,481,121 B1 | 1/2009 | Cao |
| 7,543,511 B2 | 6/2009 | Kimura et al. |
| 7,553,157 B2 | 6/2009 | Abolfathi et al. |
| 7,600,999 B2 | 10/2009 | Knopp |
| 7,658,610 B2 | 2/2010 | Knopp |
| 7,766,658 B2 | 8/2010 | Tricca et al. |
| 7,771,195 B2 | 8/2010 | Knopp et al. |
| 7,854,609 B2 | 12/2010 | Chen et al. |
| 7,871,269 B2 | 1/2011 | Wu et al. |
| 7,878,801 B2 | 2/2011 | Abolfathi et al. |
| 7,878,805 B2 | 2/2011 | Moss et al. |
| 7,883,334 B2 | 2/2011 | Li et al. |

(Continued)

FOREIGN PATENT DOCUMENTS

| | | | |
|---|---|---|---|
| CN | 101367888 | * 2/2009 | |
| WO | WO-2013162804 A1 | * 10/2013 | ............ C08F 220/10 |

OTHER PUBLICATIONS

Lewandowski et al, CN 101367888 Machine Translation, Feb. 18, 2009 (Year: 2009).*
Bielawski et al., "Synthesis of Telechelic Polyacrylates With Unsaturated End-groups," Polymer, Jun. 2003, vol. 44 (13), pp. 3721-3726.
Kinoshita et al., "Raft-based Synthesis and the Gelation Property of Telechelic Polymers That Can Immobilize Biomacromolecules," Journal of Polymer Science Polymer Chemistry, Feb. 2017, vol. 55 (8), pp. 1356-1365.

(Continued)

*Primary Examiner* — Jessica Whiteley

(74) *Attorney, Agent, or Firm* — Seed IP Law Group LLP

(57) ABSTRACT

Provided herein are curable compositions for use in a high temperature lithography-based photopolymerization process, and telechelic block polymers and methods of using such polymers in curable compositions to produce medical devices such as orthodontic appliances comprising the polymeric compositions comprising the telechelic block polymers.

22 Claims, 8 Drawing Sheets

(56) References Cited

U.S. PATENT DOCUMENTS

| | | |
|---|---|---|
| 7,914,283 B2 | 3/2011 | Kuo |
| 7,947,508 B2 | 5/2011 | Tricca et al. |
| 8,152,518 B2 | 4/2012 | Kuo |
| 8,172,569 B2 | 5/2012 | Matty et al. |
| 8,235,715 B2 | 8/2012 | Kuo |
| 8,292,617 B2 | 10/2012 | Brandt et al. |
| 8,337,199 B2 | 12/2012 | Wen |
| 8,401,686 B2 | 3/2013 | Moss et al. |
| 8,517,726 B2 | 8/2013 | Kakavand et al. |
| 8,562,337 B2 | 10/2013 | Kuo et al. |
| 8,641,414 B2 | 2/2014 | Borovinskih et al. |
| 8,684,729 B2 | 4/2014 | Wen |
| 8,708,697 B2 | 4/2014 | Li et al. |
| 8,758,009 B2 | 6/2014 | Chen et al. |
| 8,771,149 B2 | 7/2014 | Rahman et al. |
| 8,899,976 B2 | 12/2014 | Chen et al. |
| 8,899,977 B2 | 12/2014 | Cao et al. |
| 8,936,463 B2 | 1/2015 | Mason et al. |
| 8,936,464 B2 | 1/2015 | Kopelman |
| 9,022,781 B2 | 5/2015 | Kuo et al. |
| 9,119,691 B2 | 9/2015 | Namiranian et al. |
| 9,161,823 B2 | 10/2015 | Morton et al. |
| 9,241,774 B2 | 1/2016 | Li et al. |
| 9,326,831 B2 | 5/2016 | Cheang |
| 9,433,476 B2 | 9/2016 | Khardekar et al. |
| 9,610,141 B2 | 4/2017 | Kopelman et al. |
| 9,655,691 B2 | 5/2017 | Li et al. |
| 9,675,427 B2 | 6/2017 | Kopelman |
| 9,700,385 B2 | 7/2017 | Webber |
| 9,744,001 B2 | 8/2017 | Choi et al. |
| 9,844,424 B2 | 12/2017 | Wu et al. |
| 10,045,835 B2 | 8/2018 | Boronkay et al. |
| 10,111,730 B2 | 10/2018 | Webber et al. |
| 10,150,244 B2 | 12/2018 | Sato et al. |
| 10,201,409 B2 | 2/2019 | Mason et al. |
| 10,213,277 B2 | 2/2019 | Webber et al. |
| 10,299,894 B2 | 5/2019 | Tanugula et al. |
| 10,363,116 B2 | 7/2019 | Boronkay |
| 10,383,705 B2 | 8/2019 | Shanjani et al. |
| D865,180 S | 10/2019 | Bauer et al. |
| 10,449,016 B2 | 10/2019 | Kimura et al. |
| 10,463,452 B2 | 11/2019 | Matov et al. |
| 10,470,847 B2 | 11/2019 | Shanjani et al. |
| 10,492,888 B2 | 12/2019 | Chen et al. |
| 10,517,701 B2 | 12/2019 | Boronkay |
| 10,537,406 B2 | 1/2020 | Wu et al. |
| 10,537,463 B2 | 1/2020 | Kopelman |
| 10,548,700 B2 | 2/2020 | Fernie |
| 10,555,792 B2 | 2/2020 | Kopelman et al. |
| 10,588,776 B2 | 3/2020 | Cam et al. |
| 10,613,515 B2 | 4/2020 | Cramer et al. |
| 10,639,134 B2 | 5/2020 | Shanjani et al. |
| 10,743,964 B2 | 8/2020 | Wu et al. |
| 10,758,323 B2 | 9/2020 | Kopelman |
| 10,781,274 B2 | 9/2020 | Liska et al. |
| 10,813,720 B2 | 10/2020 | Grove et al. |
| 10,874,483 B2 | 12/2020 | Boronkay |
| 10,881,487 B2 | 1/2021 | Cam et al. |
| 10,912,629 B2 | 2/2021 | Tanugula et al. |
| 10,959,810 B2 | 3/2021 | Li et al. |
| 10,993,783 B2 | 5/2021 | Wu et al. |
| 11,026,768 B2 | 6/2021 | Moss et al. |
| 11,026,831 B2 | 6/2021 | Kuo |
| 11,045,282 B2 | 6/2021 | Kopelman et al. |
| 11,045,283 B2 | 6/2021 | Riley et al. |
| 11,103,330 B2 | 8/2021 | Webber et al. |
| 11,123,156 B2 | 9/2021 | Cam et al. |
| 11,154,382 B2 | 10/2021 | Kopelman et al. |
| 11,166,788 B2 | 11/2021 | Webber |
| 11,174,338 B2 | 11/2021 | Liska et al. |
| 11,219,506 B2 | 1/2022 | Shanjani et al. |
| 11,259,896 B2 | 3/2022 | Matov et al. |
| 11,273,011 B2 | 3/2022 | Shanjani et al. |
| 11,278,375 B2 | 3/2022 | Wang et al. |
| 11,318,667 B2 | 5/2022 | Mojdeh et al. |
| 11,331,166 B2 | 5/2022 | Morton et al. |
| 11,344,385 B2 | 5/2022 | Morton et al. |
| 11,376,101 B2 | 7/2022 | Sato et al. |
| 2002/0192617 A1 | 12/2002 | Phan et al. |
| 2004/0166462 A1 | 8/2004 | Phan et al. |
| 2004/0166463 A1 | 8/2004 | Wen et al. |
| 2005/0014105 A1 | 1/2005 | Abolfathi et al. |
| 2005/0186524 A1 | 8/2005 | Abolfathi et al. |
| 2005/0244768 A1 | 11/2005 | Taub et al. |
| 2006/0019218 A1 | 1/2006 | Kuo |
| 2006/0078841 A1 | 4/2006 | Desimone et al. |
| 2006/0115782 A1 | 6/2006 | Li et al. |
| 2006/0115785 A1 | 6/2006 | Li et al. |
| 2006/0199142 A1 | 9/2006 | Liu et al. |
| 2006/0234179 A1 | 10/2006 | Wen et al. |
| 2008/0118882 A1 | 5/2008 | Su |
| 2008/0160473 A1 | 7/2008 | Li et al. |
| 2008/0286716 A1 | 11/2008 | Sherwood |
| 2008/0286717 A1 | 11/2008 | Sherwood |
| 2009/0280450 A1 | 11/2009 | Kuo |
| 2010/0055635 A1 | 3/2010 | Kakavand |
| 2010/0129763 A1 | 5/2010 | Kuo |
| 2011/0269092 A1 | 11/2011 | Kuo et al. |
| 2014/0067334 A1 | 3/2014 | Kuo |
| 2014/0283983 A1* | 9/2014 | Schall .............. C08F 220/54 525/89 |
| 2015/0265376 A1 | 9/2015 | Kopelman |
| 2015/0366638 A1 | 12/2015 | Kopelman et al. |
| 2016/0193014 A1 | 7/2016 | Morton et al. |
| 2017/0007359 A1 | 1/2017 | Kopelman et al. |
| 2017/0007360 A1 | 1/2017 | Kopelman et al. |
| 2017/0007361 A1 | 1/2017 | Boronkay et al. |
| 2017/0007366 A1 | 1/2017 | Kopelman et al. |
| 2017/0007386 A1 | 1/2017 | Mason et al. |
| 2017/0135792 A1 | 5/2017 | Webber |
| 2017/0135793 A1 | 5/2017 | Webber et al. |
| 2017/0165032 A1 | 6/2017 | Webber et al. |
| 2018/0360567 A1 | 12/2018 | Xue et al. |
| 2019/0000592 A1 | 1/2019 | Cam et al. |
| 2019/0000593 A1 | 1/2019 | Cam et al. |
| 2019/0021817 A1 | 1/2019 | Sato et al. |
| 2019/0046297 A1 | 2/2019 | Kopelman et al. |
| 2019/0099129 A1 | 4/2019 | Kopelman et al. |
| 2019/0125494 A1 | 5/2019 | Li et al. |
| 2019/0125497 A1 | 5/2019 | Derakhshan et al. |
| 2019/0152152 A1 | 5/2019 | O'Leary et al. |
| 2019/0175304 A1 | 6/2019 | Morton et al. |
| 2019/0262101 A1 | 8/2019 | Shanjani et al. |
| 2019/0298494 A1 | 10/2019 | Webber et al. |
| 2019/0314119 A1 | 10/2019 | Kopelman et al. |
| 2019/0343606 A1 | 11/2019 | Wu et al. |
| 2020/0000553 A1 | 1/2020 | Makarenkova et al. |
| 2020/0100864 A1 | 4/2020 | Wang et al. |
| 2020/0100865 A1 | 4/2020 | Wang et al. |
| 2020/0100866 A1 | 4/2020 | Medvinskaya et al. |
| 2020/0155276 A1 | 5/2020 | Cam et al. |
| 2020/0188062 A1 | 6/2020 | Kopelman et al. |
| 2020/0214598 A1 | 7/2020 | Li et al. |
| 2020/0214801 A1 | 7/2020 | Wang et al. |
| 2020/0390523 A1 | 12/2020 | Sato et al. |
| 2021/0078357 A1 | 3/2021 | Venkatasanthanam et al. |
| 2021/0147672 A1 | 5/2021 | Cole et al. |

OTHER PUBLICATIONS

Messman et al., "Synthesis and Characterization of A-B-A Triblock Copolymers Derived From Chloro-telechelic Poly(L-lactide): Combining Ring-opening Polymerization (ROP) and Atom Transfer Radical Polymerization (ATRP)," Polymer Elsevier, May 2005, vol. 46 (11), pp. 3628-3638.

* cited by examiner

Vertical Dimension

Lateral Dimensions

PHOTOPOLYMERIZABLE BLOCK POLYMERS AND METHODS OF PRODUCING AND USING THE SAME

CROSS-REFERENCE

The present application is a continuation of U.S. Provisional Patent Application No. 63/179,007, filed on Apr. 23, 2021, and U.S. Provisional Patent Application No. 63/179,004, filed on Apr. 23, 2021 which are hereby incorporated by reference in their entirety for all purposes.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BACKGROUND OF THE INVENTION

Additive manufacturing (e.g., lithography-based additive manufacturing (L-AM)) techniques include a variety of techniques to fabricate objects, such as three-dimensional objects, out of photopolymerizable materials. Appliances and devices having a combination of elasticity and stiffness are desirable in various applications, such as during the fabrication of orthodontic devices or appliances, and conventional medical devices can lack these advantageous properties.

SUMMARY OF THE INVENTION

It has conventionally proven difficult to form many medical appliances through additive manufacturing techniques. One issue is that existing materials used for additive manufacturing are not biocompatible, much less appropriate for use in an intraoral environment or other part of the human body. Another issue is that existing materials used for additive manufacturing are often not viscous enough to form the precise and/or customizable features required of many appliances. Further, many current additive manufacturing techniques have relatively low curing or reaction temperatures, both for safety and cost concerns, which, for many medical appliances (including orthodontic appliances), undermines the ability to produce a product that is stable at and/or above human body temperature. Yet another issue is that existing materials used for additive manufacturing do not provide the physical, chemical, and/or thermomechanical properties (elongation, time stress-relaxation, modulus, durability, toughness, etc.) desired of aligners, other orthodontic appliances, hearing aids, and/or many medical devices. Hence, existing materials used for additive manufacturing lack many of the properties desired in medical devices, such as the ability to impart forces, torques, moments, and/or other movements that are accurate and consistent with a treatment plan.

Appliances and devices having a combination of elasticity and stiffness are desirable in various applications, such as during the fabrication of orthodontic devices or appliances. Polymeric materials can be used to fabricate orthodontic devices, enabling the use of fabrication techniques such as 3D printing. Singular polymeric materials (e.g., those that are comprised of a single polymer species) typically do not have characteristics that meet the needs of appliances and devices that are now manufactured, such as both modulus (e.g., stiffness) and elasticity. Some practitioners attempt to adjust the characteristics of the polymeric materials by adding fillers to the resin from which the polymeric material is formed. However, fillers, such as silica, can raise viscosity of resins and make them incompatible with desirable fabrication techniques. Such fillers can also increase modulus, but at the cost to elasticity. Thus, a resin that can increase internal modulus of a material without sacrificing needed elasticity is desired and in demand for various medical applications.

Orthodontic procedures typically involve repositioning a patient's teeth to a desired arrangement in order to correct malocclusions and/or improve aesthetics. To achieve these objectives, orthodontic appliances such as braces, retainers, shell aligners, and the like can be applied to the patient's teeth by an orthodontic practitioner and/or a patient. The appliance is configured to exert force on one or more teeth in order to effect desired tooth movements. The application of force can be periodically adjusted (e.g., by altering the appliance or using different types of appliances) in order to incrementally reposition the teeth to a desired arrangement. Polymeric materials can be used to fabricate appliances to be used to reposition a patient's teeth. Polymeric materials that have dual characteristics of stiffness and elasticity are desirable, as are 3D printable resins that can form such polymeric materials.

Against the issues referenced herein, the present disclosure aims to provide curable compositions for use in a high temperature lithography-based photopolymerization processes. These curable compositions may be used in a variety of applications, including for the formation of medical devices and/or those items used in an intraoral environment, e.g., intraoral devices, such as aligners, expanders, or spacers. Particularly in view of the challenges around singular polymeric materials in medical devices, the present disclosure provides photo-curable resins that comprise one or more telechelic block copolymers composed of two or more different monomers, wherein such telechelic block copolymer can comprise photopolymerizable end groups and can have a molecular weight of at most about 50 kDa, 30 kDa, or 25 kDa. Such telechelic block copolymers can provide (e.g., upon photo-curing) polymeric materials with properties that are particularly well suited for applications in medical devices, e.g., orthodontic appliances, and can hence address the demand for photo-curable compositions that allow the productions of materials with a wide range of specific mechanical properties.

Accordingly, this disclosure aims to provide compositions, methods, and systems for use in a high temperature lithography-based photopolymerization, as well as devices made from said high temperature lithography-based photopolymerization.

In various aspects, provided herein is a telechelic polymer comprising a monomer, wherein the monomer comprises a reactive functional group, and wherein two or more of the following conditions are met: (i) the monomer has a vapor pressure of at most 8000 Pa at 60° C. in its monomeric state; (ii) following 2 h heating at 90° C. in its monomeric state, the monomer has a mass loss rate of less than 0.25% per hour at 90° C.; (iii) the molecular weight of the telechelic polymer is not more than 50 kDa; and (iv) the reactive functional group comprises a photopolymerizable moiety. In some aspects, the monomer is a terminal monomer. In some aspects, the monomer is an internal monomer. In some aspects, three or more of conditions (i), (ii), (iii) and (iv) are met. In some aspects, all of conditions (i), (ii), (iii) and (iv) are met. In some aspects, the monomer has a vapor pressure from 2 Pa to 10 Pa at 60° C. in its monomeric state. In some aspects, the monomer has a vapor pressure from 2 Pa to 5 Pa at 60° C. in its monomeric state. In some aspects, following 2 h heating at 90° C., the monomer has a mass loss rate from 0.05% to 0.225% per hour at 90° C. in its monomeric state. In some aspects, following 2 h heating at 90° C., the monomer has a mass loss rate from 0.025% to 0.125% per hour at 90° C. in its monomeric state. In some aspects, the molecular weight of the telechelic polymer is from 5 kDa to 40 kDa. In some aspects, the molecular weight of the telechelic polymer is from 5 kDa to 30 kDa. In some aspects, the molecular weight of the telechelic polymer is from 5 kDa to 20 kDa. In some aspects, the molecular weight of the telechelic polymer is from 5 kDa to 15 kDa. In some aspects, the photopolymerizable moiety comprises an acrylate, methacrylate, vinyl acrylate, vinyl methacrylate, allyl ether, silene, alkyne, alkene, vinyl ether, maleimide, fumarate, maleate, itoconate, or styrenyl moiety. In some aspects, the photopolymerizable moiety comprises an acrylate or methacrylate moiety. In some aspects, the photopolymerizable moiety is capable of undergoing a photo-induced Diels-Alder click reaction or a photodimerization reaction. In some aspects, the monomer has a melting point of at least 25° C. when in its monomer state. In some aspects, the monomer is a compound according to Formula (I):

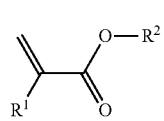

wherein,
R$^1$ is H, substituted or unsubstituted C$_1$-C$_3$ alkyl or halogen; and
R$^2$ is substituted or unsubstituted C$_{1-6}$ alkyl, substituted or unsubstituted C$_{1-6}$ heteroalkyl, substituted or unsubstituted C$_{1-6}$ carbonyl, substituted or unsubstituted C$_{1-6}$ carboxy, substituted or unsubstituted aryl, substituted or unsubstituted heteroaryl, substituted or unsubstituted cyclo(C$_{3-8}$) alkyl, or substituted or unsubstituted cyclo(C$_{3-8}$) heteroalkyl.

In some aspects, R$^1$ is H or methyl. In some aspects, R$^2$ is substituted or unsubstituted aryl, substituted or unsubstituted heteroaryl, substituted or unsubstituted cyclo(C$_{3-8}$) alkyl, or substituted or unsubstituted cyclo(C$_{3-8}$) heteroalkyl. In such instances, R$^2$ is substituted or unsubstituted aryl. In some instances, R$^2$ is substituted or unsubstituted heteroaryl. In some instances, R$^2$ is substituted or unsubstituted cyclo(C$_{5-7}$) alkyl. In some instances, R$^2$ is substituted or unsubstituted cyclo(C$_{5-7}$) heteroalkyl.

In various aspects, provided herein is a photo-curable resin comprising a telechelic polymer of the present disclosure. In some instances, the photo-curable resin is capable of undergoing polymerization-induced phase separation along one or more lateral directions during photo-curing. In some instances, the photo-curable resin, when polymerized, comprises one or more polymeric phases. In some instances, at least one polymeric phase of the one or more polymeric phases has a glass transition temperature (T$_g$) of at least 60° C., 80° C., 90° C., 100° C., or at least 110° C. In some instances, the telechelic polymer, in a polymerized form, is a component of the at least one polymeric phase that has the T$_g$ of at least 60° C., 80° C., 90° C., 100° C., or at least 110° C. In some instances, at least one polymeric phase of the one or more polymeric phases comprises a crystalline polymeric material. In some instances, the crystalline polymeric material has a melting point of at least 60° C., 80° C., 90° C., 100° C., or at least 110° C. In some instances, the photo-curable resin can further comprise a second telechelic polymer comprising a second monomer, wherein the second monomer comprises a second reactive functional group, and wherein one or more of the following conditions are met: (v) the second monomer has a vapor pressure of at most 8000 Pa at 60° C. in its monomeric state; (vi) following 2 h heating at 90° C., the second monomer has a mass loss rate of less than 0.25% per hour at 90° C. in its monomeric state; (vii) the molecular weight of the second telechelic polymer is not more than 50 kDa; and (viii) the second reactive functional group comprises a second photopolymerizable moiety. In some aspects, four or more of conditions (i), (ii), (iii), (iv), (v), (vi), (vii), and (viii) are met. In some aspects, five or more of conditions (i), (ii), (iii), (iv), (v), (vi), (vii), and (viii) are met. In some aspects, six or more of conditions (i), (ii), (iii), (iv), (v), (vi), (vii), and (viii) are met. In some aspects, seven or more of conditions (i), (ii), (iii), (iv), (v), (vi), (vii), and (viii) are met. In some aspects, all of conditions (i), (ii), (iii), (iv), (v), (vi), (vii), and (viii) are met. In some aspects, the second monomer is a terminal monomer. In some aspects, the second monomer is an internal monomer. In some aspects, the second monomer has a vapor pressure from 2 Pa to 10 Pa at 60° C. in its monomeric state. In some aspects, the second monomer has a vapor pressure from 2 Pa to 5 Pa at 60° C. in its monomeric state. In some aspects, following 2 h heating at 90° C., the second monomer has a mass loss rate from 0.05% to 0.225% at 90° C. in its monomeric state. In some aspects, following 2 h heating at 90° C., the second monomer has a mass loss rate from 0.025% to 0.125% at 90° C. in its monomeric state. In some aspects, the molecular weight of the second telechelic polymer is from 5 kDa to 40 kDa. In some aspects, the molecular weight of the second telechelic polymer is from 5 kDa to 30 kDa. In some aspects, the molecular weight of the second telechelic polymer is from 5 kDa to 20 kDa. In some aspects, the molecular weight of the second telechelic polymer is from 5 kDa to 15 kDa. In some aspects, the second photopolymerizable moiety comprises an acrylate, methacrylate, vinyl acrylate, vinyl methacrylate, allyl ether, silene, alkyne, alkene, vinyl ether, maleimide, fumarate, maleate, itoconate, or styrenyl moiety. In some aspects, the second photopolymerizable moiety comprises an acrylate or a methacrylate moiety. In some aspects, the second photopolymerizable moiety is capable of undergoing a photo-induced Diels-Alder click reaction or a photodimerization reaction. In some aspects, the second monomer has a melting point of at least 25° C. when in its monomer state. In some aspects, the second monomer is different to the first monomer, and wherein the second monomer is a compound according to Formula (II):

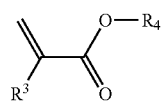

wherein,
R$^3$ is H, substituted or unsubstituted C$_{1-3}$ alkyl or halogen; and
R$^4$ is substituted or unsubstituted C$_{1-6}$ alkyl, substituted or unsubstituted C$_{1-6}$ heteroalkyl, substituted or unsubstituted C$_{1-6}$ carbonyl, substituted or unsubstituted C$_{1-6}$ carboxy, substituted or unsubstituted aryl, substituted or unsubstituted heteroaryl, substituted or unsubstituted cyclo($C_{3-8}$) alkyl, or substituted or unsubstituted cyclo ($C_{3-8}$) heteroalkyl. In some aspects, the first monomer and the second monomer are part of a telechelic block copolymer. In some aspects, the telechelic block copolymer has a block configuration of AB, wherein "A" is the first block in the telechelic block copolymer and "B" is the second block in the telechelic block copolymer. In some aspects, the telechelic block copolymer is a compound according to Formula (III):

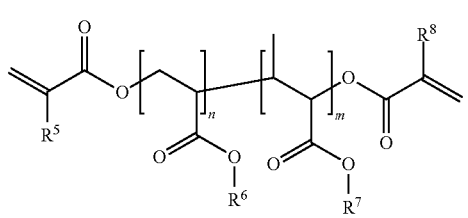

wherein, $R^5$ and $R^8$ are independently H, substituted or unsubstituted $C_{1-3}$ alkyl or halogen; $R^6$ and $R^7$ are independently substituted or unsubstituted $C_{1-6}$ alkyl, substituted or unsubstituted $C_{1-6}$ heteroalkyl, substituted or unsubstituted $C_{1-6}$ carbonyl, substituted or unsubstituted $C_{1-6}$ carboxy, substituted or unsubstituted aryl, substituted or unsubstituted heteroaryl, substituted or unsubstituted cyclo($C_{3-8}$) alkyl, or substituted or unsubstituted cyclo($C_{3-8}$) heteroalkyl, and $R^6 \neq R^7$; and n and m are independently positive integers from 1 to 300. In some cases, n and m are independently positive integers from 1 to 100.

In some aspects, the telechelic block copolymer has a configuration of ABA or BAB, wherein "A" is a block comprised of the first monomer in the telechelic block copolymer and "B" is a block comprised of the second monomer in the telechelic block copolymer. In some aspects, the telechelic block copolymer further comprises a macro-initiator. In some aspects, the macro-initiator is a polycaprolactone, a polytetrahydrofuran, a hydrogenated polyethylene, a hydroxy terminated polystyrene, a polyester diol (or diacid), a polycarbonate diol, or a polystyrene dihalide. In some aspects, the telechelic block copolymer has a polydispersity index (PDI) of from about 0.5 to about 3, or from about 1 to about 2. In some aspects, the photo-curable resin is capable of being 3D printed at a temperature of at least 25° C. In some aspects, the photo-curable resin is capable of being 3D printed at a temperature of at least 30° C., 40° C., 50° C., 60° C., 80° C., or 100° C. In some aspects, the photo-curable resin further comprises a reactive diluent. In some aspects, the photo-curable resin has a viscosity from 30 cP to 50,000 cP at a printing temperature. In some aspects, the printing temperature is from 20° C. to 150° C. In some aspects, the photo-curable resin comprises less than 20 wt % hydrogen bonding units. In some aspects, the photo-curable resin further comprises a crosslinking modifier, a light blocker, a solvent, a glass transition temperature modifier, or a combination thereof. In some aspects, the photo-curable resin comprises 0.5-99.5 wt %, 1-99 wt %, 10-95 wt %, 20-90 wt %, 25-60 wt %, or 35-50 wt % of the telechelic polymer, the second telechelic polymer, the telechelic block copolymer, or a combination thereof.

In various aspects, provided herein is a polymeric material formed from a photo-curable resin described herein. In some aspects, the polymeric material has one or more of the following characteristics: (A) a tensile modulus greater than or equal to 200 MPa; (B) a flexural stress and/or flexural modulus of greater than or equal to 1.5 MPa remaining after 24 hours in a wet environment at 37° C.; (C) an elongation at break greater than or equal to 5%; (D) a water uptake of less than 25 wt % when measured after 24 hours in a wet environment at 37° C.; (E) transmission of at least 30% of visible light through the polymeric material after 24 hours in a wet environment at 37° C.; and (F) comprises a plurality of polymeric phases, wherein at least one polymeric phase of the one or more polymeric phases has a $T_g$ of at least 60° C., 80° C., 90° C., 100° C., or at least 110° C. In some aspects, the polymeric material has at least two characteristics of (A), (B), (C), (D), (E) and (F). In some aspects, the polymeric material has at least three characteristics of (A), (B), (C), (D), (E) and (F). In some aspects, the polymeric material has at least four characteristics of (A), (B), (C), (D), (E) and (F). In some aspects, the polymeric material has at least five characteristics of (A), (B), (C), (D), (E) and (F). In some aspects, the polymeric material has all of the characteristics (A), (B), (C), (D), (E) and (F). In some aspects, the polymeric material is characterized by a water uptake of less than 20 wt %, less than 15 wt %, less than 10 wt %, less than 5 wt %, less than 4 wt %, less than 3 wt %, less than 2 wt %, less than 1 wt %, less than 0.5 wt %, less than 0.25 wt %, or less than 0.1 wt % when measured after 24 hours in a wet environment at 37° C. In some aspects, the polymeric material has greater than 60% conversion of double bonds to single bonds compared to the photo-curable resin, as measured by FTIR. In some aspects, the polymeric material has an ultimate tensile strength from 10 MPa to 100 MPa, from 15 MPa to 80 MPa, from 20 MPa to 60 MPa, from 10 MPa to 50 MPa, from 10 MPa to 45 MPa, from 25 MPa to 40 MPa, from 30 MPa to 45 MPa, or from 30 MPa to 40 MPa after 24 hours in a wet environment at 37° C. In some aspects, the polymeric material is characterized by an elongation at break greater than 10%, an elongation at break greater than 20%, an elongation at break greater than 30%, an elongation at break of 5% to 250%, an elongation at break of 20% to 250%, or an elongation at break value between 40% and 250% after 24 hours in a wet environment at 37° C. In some aspects, the polymeric material is characterized by a storage modulus of 0.1 MPa to 4000 MPa, a storage modulus of 300 MPa to 3000 MPa, or a storage modulus of 750 MPa to 3000 MPa after 24 hours in a wet environment at 37° C. In some aspects, wherein the polymeric material has a flexural stress and/or flexural modulus remaining of 100 MPa or more, 80 MPa or more, 70 MPa or more, 60 MPa or more, or 50 MPa or more after 24 hours in a wet environment at 37° C. In some aspects, at least 40%, 50%, 60%, or 70% of visible light passes through the polymeric material after 24 hours in a wet environment at 37° C. In some aspects, the polymeric material is biocompatible, bioinert, or a combination thereof. In some aspects, the polymeric material is capable of being 3D printed.

Further provided herein is a polymeric film comprising a polymeric material of the present disclosure. In some aspects, the film has a thickness of at least 100 μm and not more than 3 mm.

Further provided herein is a device comprising a polymeric material of the present disclosure or a polymeric film of the present disclosure.

Further provided herein is a medical device comprising a polymeric material of the present disclosure or a polymeric film of the present disclosure. In some aspects, the medical device is an orthodontic appliance. In some aspects, the orthodontic appliance is a dental aligner, a dental expander or a dental spacer. In some aspects, the medical device is capable of being produced by 3D printing.

In various aspects, provided herein is a method of synthesizing a telechelic block copolymer, comprising (i) coupling a telechelic polymer (A) to a second telechelic polymer (B), thereby producing the telechelic block copolymer, wherein the telechelic block copolymer comprises photopolymerizable end groups at its termini, and wherein the telechelic block copolymer has a number-average molecular weight of at most about 50 kDa. In some aspects, the telechelic polymer and the second telechelic polymer are produced by Atom Transfer Radical Polymerization (ATRP), Reversible Addition Fragmentation chain transfer polymerization (RAFT), and/or anionic polymerization.

In various aspects, provided herein is a method of forming a polymeric material, the method comprising: (i) providing a photo-curable resin of the present disclosure; (ii) exposing the photo-curable resin to a light source; and (iii) curing the photo-curable resin to form the polymeric material. In some aspects, the method further comprises inducing phase separation along one or more lateral directions in the forming polymeric material during photo-curing. In some aspects, the polymeric material comprises one or more polymeric phases. In some aspects, at least one polymeric phase of the one or more polymeric phases has a glass transition temperature ($T_g$) of at least 60° C., 80° C., 90° C., 100° C., or at least 110° C. In some aspects, the telechelic polymer, in a polymerized form, is a component of the at least one polymeric phase that has the $T_g$ of at least 60° C., 80° C., 90° C., 100° C., or at least 110° C. In some aspects, at least one polymeric phase of the one or more polymeric phases comprises a crystalline polymeric material. In some aspects, the crystalline polymeric material has a melting point of at least 60° C., 80° C., 90° C., 100° C., or at least 110° C. In some aspects, the polymeric material comprises one or more amorphous phases having the $T_g$ of at least 60° C., 80° C., 90° C., 100° C., or at least 110° C. and one or more crystalline phases comprising the crystalline polymeric material having the melting point of at least 60° C., 80° C., 90° C., 100° C., or at least 110° C. In some aspects, the polymeric material is characterized by one or more of: (i) a tensile modulus greater than or equal to 200 MPa; (ii) a flexural stress of greater than or equal to 1.5 MPa remaining after 24 hours in a wet environment at 37° C.; and (iii) an elongation at break greater than or equal to 5%. In some aspects, the method further comprises fabricating a medical device with the polymeric material. In some aspects, the medical device is an orthodontic appliance. In some aspects, the orthodontic appliance is a dental aligner, a dental expander or a dental spacer.

In various aspects, provided herein is a telechelic polymer comprising a terminal monomer, wherein the terminal monomer comprises a reactive functional group, and wherein two or more of the following conditions are met: (i) the terminal monomer has a vapor pressure of at most 12 Pa at 60° C. in its monomeric state; (ii) the terminal monomer has a mass loss of less than 0.5% after heating at 90° C. for 2 h in its monomeric state; (iii) the molecular weight of the telechelic polymer is not more than 50 kDa; and (iv) the reactive functional group comprises a photoreactive moiety. In some aspects, three or more of conditions (i), (ii), (iii) and (iv) are met. In some aspects, all of conditions (i), (ii), (iii) and (iv) are met. In some aspects, the terminal monomer has a vapor pressure from 2 Pa to 10 Pa at 60° C. in its monomeric state. In some aspects, the terminal monomer has a vapor pressure from 2 Pa to 5 Pa at 60° C. in its monomeric state. In some aspects, the terminal monomer has a mass loss from 0.1% to 0.45% after heating at 90° C. for 2 h in its monomeric state. In some aspects, the terminal monomer has a mass loss from 0.05% to 0.25% after heating at 90° C. for 2 h in its monomeric state. In some aspects, the molecular weight of the telechelic polymer is from 5 kDa to 40 kDa. In some aspects, the molecular weight of the telechelic polymer is from 5 kDa to 30 kDa. In some aspects, the molecular weight of the telechelic polymer is from 5 kDa to 20 kDa. In some aspects, the molecular weight of the telechelic polymer is from 5 kDa to 15 kDa. In some aspects, the photoreactive moiety comprises an acrylate, methacrylate, vinyl acrylate, vinyl methacrylate, allyl ether, silene, alkyne, alkene, vinyl ether, maleimide, fumarate, maleate, itoconate, or styrenyl moiety. In some aspects, the photoreactive moiety comprises an acrylate or methacrylate moiety. In some aspects, the photoreactive moiety is capable of undergoing a photo-induced Diels-Alder click reaction or a photodimerization reaction. In some aspects, the terminal monomer has a melting point of at least 25° C. when in its monomer state. In some aspects, the terminal monomer is a compound according to Formula (I):

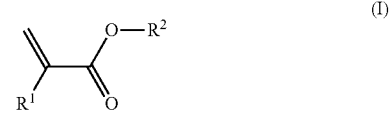

wherein,
R[1] is H, substituted or unsubstituted $C_{1-3}$ alkyl or halogen; and
R[2] is substituted or unsubstituted $C_{1-6}$ alkyl, substituted or unsubstituted $C_{1-6}$ heteroalkyl, substituted or unsubstituted $C_{1-6}$ carbonyl, substituted or unsubstituted $C_{1-6}$ carboxy, substituted or unsubstituted aryl, substituted or unsubstituted heteroaryl, substituted or unsubstituted cyclo($C_{3-8}$) alkyl, or substituted or unsubstituted cyclo($C_{3-8}$) heteroalkyl.

In some aspects, le is H or methyl. In some aspects, R[2] is substituted or unsubstituted aryl, substituted or unsubstituted heteroaryl, substituted or unsubstituted cyclo($C_{3-8}$) alkyl, or substituted or unsubstituted cyclo($C_{3-8}$) heteroalkyl. In such instances, R[2] is substituted or unsubstituted aryl. In some instances, R[2] is substituted or unsubstituted heteroaryl. In some instances, R[2] is substituted or unsubstituted cyclo($C_{5-7}$) alkyl. In some instances, R[2] is substituted or unsubstituted cyclo($C_{5-7}$) heteroalkyl.

In various aspects, provided herein is a photo-curable resin comprising a telechelic polymer of the present disclosure. In some instances, the photo-curable resin is capable of undergoing polymerization-induced phase separation along one or more lateral directions during photo-curing. In some instances, the photo-curable resin, when polymerized, comprises one or more polymeric phases. In some instances, at least one polymeric phase of the one or more polymeric phases has a glass transition temperature ($T_g$) of at least 60° C., 80° C., 90° C., 100° C., or at least 110° C. In some instances, the telechelic polymer, in a polymerized form, is a component of the at least one polymeric phase that has the $T_g$ of at least 60° C., 80° C., 90° C., 100° C., or at least 110° C. In some instances, at least one polymeric phase of the one or more polymeric phases comprises a crystalline polymeric material. In some instances, the crystalline polymeric material has a melting point of at least 60° C., 80° C., 90° C., 100° C., or at least 110° C. In some instances, the photo-curable resin can further comprise a second telechelic polymer comprising a second terminal monomer, wherein the second terminal monomer comprises a second reactive functional group, and wherein one or more of the following conditions are met: (v) the second terminal monomer has a vapor pressure of at most 12 Pa at 60° C. in its monomeric state; (vi) the second terminal monomer has a mass loss of less than 0.5% after heating at 90° C. for 2 h in its monomeric state; (vii) the molecular weight of the second telechelic polymer is not more than 50 kDa; and (viii) the second reactive functional group comprises a second photoreactive moiety. In some aspects, four or more of conditions (i), (ii), (iii), (iv), (v), (vi), (vii), and (viii) are met. In some aspects, five or more of conditions (i), (ii), (iii), (iv), (v), (vi), (vii), and (viii) are met. In some aspects, six or more of conditions (i), (ii), (iii), (iv), (v), (vi), (vii), and (viii) are met. In some aspects, seven or more of conditions (i), (ii), (iii), (iv), (v), (vi), (vii), and (viii) are met. In some aspects, all of conditions (i), (ii), (iii), (iv), (v), (vi), (vii), and (viii) are met. In some aspects, the second terminal monomer has a vapor pressure from 2 Pa to 10 Pa at 60° C. in its monomeric state. In some aspects, the second terminal monomer has a vapor pressure from 2 Pa to 5 Pa at 60° C. in its monomeric state. In some aspects, the second terminal monomer has a mass loss from 0.1% to 0.45% after heating at 90° C. for 2 h in its monomeric state. In some aspects, the second terminal monomer has a mass loss from 0.05% to 0.25% after heating at 90° C. for 2 h in its monomeric state. In some aspects, the molecular weight of the second telechelic polymer is from 5 kDa to 40 kDa. In some aspects, the molecular weight of the second telechelic polymer is from 5 kDa to 30 kDa. In some aspects, the molecular weight of the second telechelic polymer is from 5 kDa to 20 kDa. In some aspects, the molecular weight of the second telechelic polymer is from 5 kDa to 15 kDa. In some aspects, the second photoreactive moiety comprises an acrylate, methacrylate, vinyl acrylate, vinyl methacrylate, allyl ether, silene, alkyne, alkene, vinyl ether, maleimide, fumarate, maleate, itoconate, or styrenyl moiety. In some aspects, the second photoreactive moiety comprises an acrylate or a methacrylate moiety. In some aspects, the second photoreactive moiety is capable of undergoing a photo-induced Diels-Alder click reaction or a photodimerization reaction. In some aspects, the second terminal monomer has a melting point of at least 25° C. when in its monomer state. In some aspects, the second terminal monomer is different to the terminal monomer, and wherein the second terminal monomer is a compound according to Formula (II):

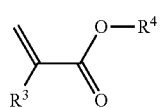

(II)

wherein,
R$^3$ is H, substituted or unsubstituted C$_{1-3}$ alkyl or halogen; and
R$^4$ is substituted or unsubstituted C$_{1-6}$ alkyl, substituted or unsubstituted C$_{1-6}$ heteroalkyl, substituted or unsubstituted C$_{1-6}$ carbonyl, substituted or unsubstituted C$_{1-6}$ carboxy, substituted or unsubstituted aryl, substituted or unsubstituted heteroaryl, substituted or unsubstituted cyclo(C$_{3-8}$) alkyl, or substituted or unsubstituted cyclo (C$_{3-8}$) heteroalkyl. In some aspects, the first telechelic polymer and the second telechelic polymer are part of a telechelic block copolymer. In some aspects, the telechelic block copolymer has a block configuration of AB, wherein "A" is the telechelic polymer and "B" is the second telechelic polymer. In some aspects, the telechelic block copolymer is a compound according to Formula (III):

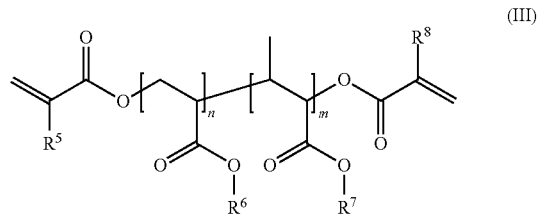

(III)

wherein,
R$^5$ and R$^8$ are independently H, substituted or unsubstituted C$_{1-3}$ alkyl or halogen;
R$^6$ and R$^7$ are independently substituted or unsubstituted C$_{1-6}$ alkyl, substituted or unsubstituted C$_{1-6}$ heteroalkyl, substituted or unsubstituted C$_{1-6}$ carbonyl, substituted or unsubstituted C$_{1-6}$ carboxy, substituted or unsubstituted aryl, substituted or unsubstituted heteroaryl, substituted or unsubstituted cyclo(C$_{3-8}$) alkyl, or substituted or unsubstituted cyclo(C$_{3-8}$) heteroalkyl, and R$^6$≠R$^7$; and
n and m are independently positive integers from 1 to 100.

In some aspects, the telechelic block copolymer has a configuration of ABA or BAB, wherein "A" is the telechelic polymer and "B" is the second telechelic polymer. In some aspects, the telechelic block copolymer further comprises a macro-initiator. In some aspects, the macro-initiator is a polycaprolactone, a polytetrahydrofuran, a hydrogenated polyethylene, a hydroxy terminated polystyrene, a polyester diol, a polycarbonate diol, or a polystyrene dihalide. In some aspects, the telechelic block copolymer has a polydispersity index (PDI) of from about 0.5 to about 3, or from about 1 to about 2. In some aspects, the photo-curable resin is capable of being 3D printed at a temperature of at least 25° C. In some aspects, the photo-curable resin is capable of being 3D printed at a temperature of at least 30° C., 40° C., 50° C., 60° C., 80° C., or 100° C. In some aspects, the photo-curable resin further comprises a reactive diluent. In some aspects, the photo-curable resin has a viscosity from 30 cP to 50,000 cP at a printing temperature. In some aspects, the printing temperature is from 20° C. to 150° C. In some aspects, the photo-curable resin comprises less than 20 wt % hydrogen bonding units. In some aspects, the photo-curable resin further comprises a crosslinking modifier, a light blocker, a solvent, a glass transition temperature modifier, or a combination thereof. In some aspects, the photo-curable resin comprises 0.5-99.5 wt %, 1-99 wt %, 10-95 wt %, 20-90 wt %, 25-60 wt %, or 35-50 wt % of the telechelic polymer, the second telechelic polymer, the telechelic block copolymer, or a combination thereof.

In various aspects, provided herein is a polymeric material formed from a photo-curable resin described herein. In some aspects, the polymeric material has one or more of the following characteristics: (A) a tensile modulus greater than or equal to 200 MPa; (B) a flexural stress of greater than or equal to 1.5 MPa remaining after 24 hours in a wet environment at 37° C.; (C) an elongation at break greater than or equal to 5%; (D) a water uptake of less than 25 wt % when measured after 24 hours in a wet environment at 37° C.; (E) transmission of at least 30% of visible light through the polymeric material after 24 hours in a wet environment at 37° C.; and (F) comprises a plurality of polymeric phases, wherein at least one polymeric phase of the one or more polymeric phases has a $T_g$ of at least 60° C., 80° C., 90° C., 100° C., or at least 110° C. In some aspects, the polymeric material has at least two characteristics of (A), (B), (C), (D), (E) and (F). In some aspects, the polymeric material has at least three characteristics of (A), (B), (C), (D), (E) and (F). In some aspects, the polymeric material has at least four characteristics of (A), (B), (C), (D), (E) and (F). In some aspects, the polymeric material has at least five characteristics of (A), (B), (C), (D), (E) and (F). In some aspects, the polymeric material has all of the characteristics (A), (B), (C), (D), (E) and (F). In some aspects, the polymeric material is characterized by a water uptake of less than 20 wt %, less than 15 wt %, less than 10 wt %, less than 5 wt %, less than 4 wt %, less than 3 wt %, less than 2 wt %, less than 1 wt %, less than 0.5 wt %, less than 0.25 wt %, or less than 0.1 wt % when measured after 24 hours in a wet environment at 37° C. In some aspects, the polymeric material has greater than 60% conversion of double bonds to single bonds compared to the photo-curable resin, as measured by FTIR. In some aspects, the polymeric material has an ultimate tensile strength from 10 MPa to 100 MPa, from 15 MPa to 80 MPa, from 20 MPa to 60 MPa, from 10 MPa to 50 MPa, from 10 MPa to 45 MPa, from 25 MPa to 40 MPa, from 30 MPa to 45 MPa, or from 30 MPa to 40 MPa after 24 hours in a wet environment at 37° C. In some aspects, the polymeric material is characterized by an elongation at break greater than 10%, an elongation at break greater than 20%, an elongation at break greater than 30%, an elongation at break of 5% to 250%, an elongation at break of 20% to 250%, or an elongation at break value between 40% and 250% after 24 hours in a wet environment at 37° C. In some aspects, the polymeric material is characterized by a storage modulus of 0.1 MPa to 4000 MPa, a storage modulus of 300 MPa to 3000 MPa, or a storage modulus of 750 MPa to 3000 MPa after 24 hours in a wet environment at 37° C. In some aspects, wherein the polymeric material has a flexural stress remaining of 100 MPa or less, 80 MPa or less, 70 MPa or less, 60 MPa or less, or 50 MPa or less after 24 hours in a wet environment at 37° C. In some aspects, at least 40%, 50%, 60%, or 70% of visible light passes through the polymeric material after 24 hours in a wet environment at 37° C. In some aspects, the polymeric material is biocompatible, bioinert, or a combination thereof. In some aspects, the polymeric material is capable of being 3D printed.

Further provided herein is a polymeric film comprising a polymeric material of the present disclosure. In some aspects, the film has a thickness of at least 100 µm and not more than 3 mm.

Further provided herein is a device comprising a polymeric material of the present disclosure or a polymeric film of the present disclosure.

Further provided herein is a medical device comprising a polymeric material of the present disclosure or a polymeric film of the present disclosure. In some aspects, the medical device is an orthodontic appliance. In some aspects, the orthodontic appliance is a dental aligner, a dental expander or a dental spacer. In some aspects, the medical device is capable of being produced by 3D printing.

In various aspects, provided herein is a method of synthesizing a telechelic block copolymer, comprising (i) coupling a telechelic polymer (A) to a second telechelic polymer (B), thereby producing the telechelic block copolymer, wherein the telechelic block copolymer comprises photopolymerizable end groups at its termini, and wherein the telechelic block copolymer has a number-average molecular weight of at most about 50 kDa. In some aspects, the telechelic polymer and the second telechelic polymer are produced by Atom Transfer Radical Polymerization (ATRP), Reversible Addition Fragmentation chain transfer polymerization (RAFT), and/or anionic polymerization.

In various aspects, provided herein is a method of forming a polymeric material, the method comprising: (i) providing a photo-curable resin of the present disclosure; (ii) exposing the photo-curable resin to a light source; and (iii) curing the photo-curable resin to form the polymeric material. In some aspects, the method further comprises inducing phase separation along one or more lateral directions in the forming polymeric material during photo-curing. In some aspects, the polymeric material comprises one or more polymeric phases. In some aspects, at least one polymeric phase of the one or more polymeric phases has a glass transition temperature ($T_g$) of at least 60° C., 80° C., 90° C., 100° C., or at least 110° C. In some aspects, the telechelic polymer, in a polymerized form, is a component of the at least one polymeric phase that has the $T_g$ of at least 60° C., 80° C., 90° C., 100° C., or at least 110° C. In some aspects, at least one polymeric phase of the one or more polymeric phases comprises a crystalline polymeric material. In some aspects, the crystalline polymeric material has a melting point of at least 60° C., 80° C., 90° C., 100° C., or at least 110° C. In some aspects, the polymeric material comprises one or more amorphous phases having the $T_g$ of at least 60° C., 80° C., 90° C., 100° C., or at least 110° C. and one or more crystalline phases comprising the crystalline polymeric material having the melting point of at least 60° C., 80° C., 90° C., 100° C., or at least 110° C. In some aspects, the polymeric material is characterized by one or more of: (i) a tensile modulus greater than or equal to 200 MPa; (ii) a flexural stress of greater than or equal to 1.5 MPa remaining after 24 hours in a wet environment at 37° C.; and (iii) an elongation at break greater than or equal to 5%. In some aspects, the method further comprises fabricating a medical device with the polymeric material. In some aspects, the medical device is an orthodontic appliance. In some aspects, the orthodontic appliance is a dental aligner, a dental expander or a dental spacer.

Further provided herein is a method of repositioning a patient's teeth, the method comprising: (i) generating a treatment plan for the patient, the plan comprising a plurality of intermediate tooth arrangements for moving teeth along a treatment path from an initial tooth arrangement toward a final tooth arrangement; (ii) producing an orthodontic appliance comprising a polymeric material of the present disclosure; and (iii) moving on-track, with the orthodontic appliance, at least one of the patient's teeth toward an intermediate tooth arrangement or the final tooth arrangement. In some aspects, producing the orthodontic appliance comprises 3D printing of the orthodontic appliance. In some aspects, the method further comprises tracking progression of the patient's teeth along the treatment path after administration of the orthodontic appliance to the patient, the tracking comprising comparing a current arrangement of the patient's teeth to a planned arrangement of the patient's teeth. In some aspects, greater than 60% of the patient's teeth are on track with the treatment plan after 2 weeks of treatment. In some aspects, the orthodontic appliance has a retained repositioning force to the at least one of the patient's teeth after 2 days that is at least 10%, at least 20%, at least 30%, at least 40%, at least 50%, at least 60%, or at least 70% of repositioning force initially provided to the at least one of the patient's teeth.

DESCRIPTION OF THE FIGURES

The novel features of the invention are set forth with particularity in the appended claims. A better understanding of the features and advantages of the present disclosure will be obtained by reference to the following detailed description that sets forth illustrative embodiments, in which the principles of the invention are utilized, and the accompanying drawings of which:

DETAILED DESCRIPTION

I. Introduction

Figure 1A:
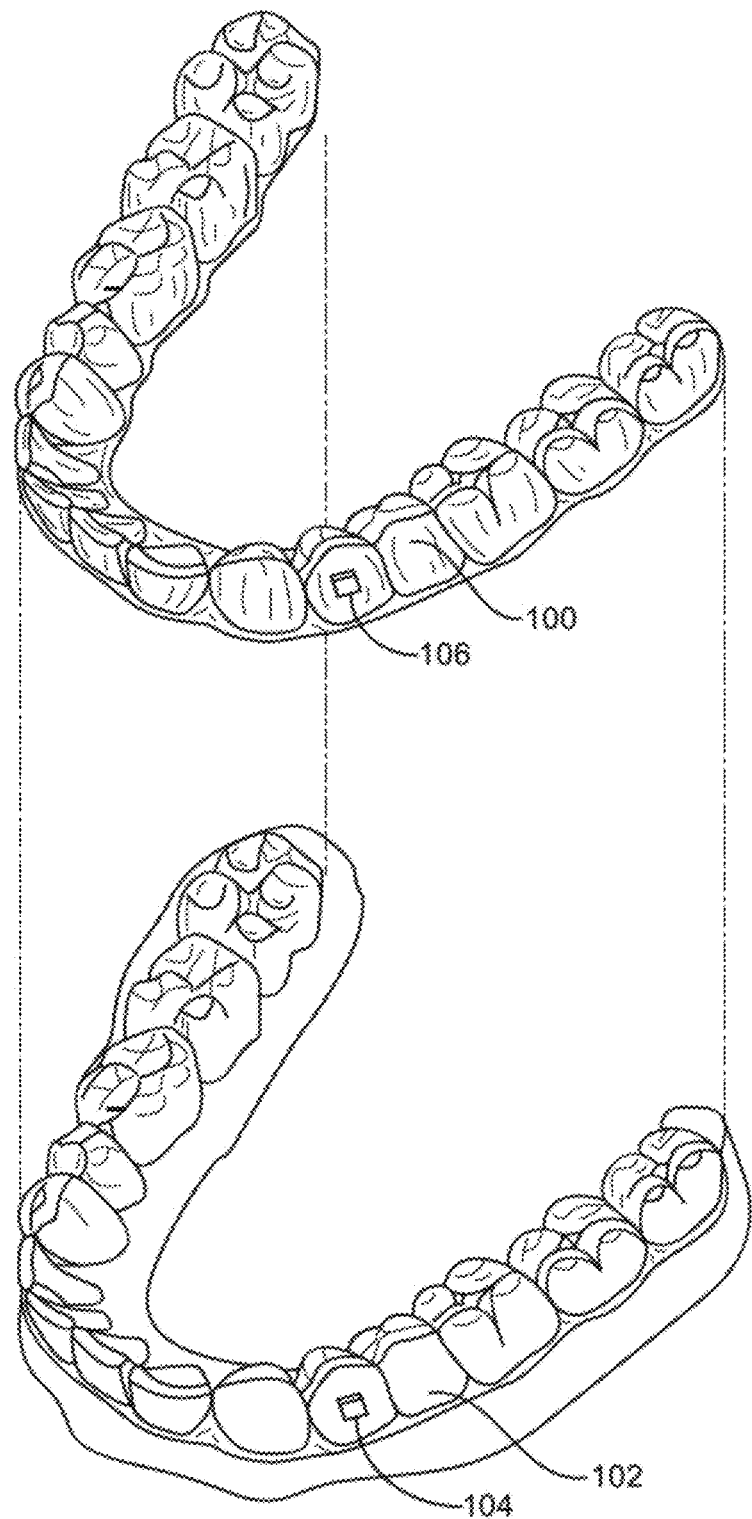
FIG. 1A illustrates a tooth repositioning appliance, in accordance with embodiments.

The present disclosure provides photopolymerizable polymers such as telechelic block copolymers, as well as compositions comprising such polymers and methods of using the same, e.g., in the production of medical devices such as orthodontic appliances. A telechelic polymer provided herein can comprise a monomer, wherein the monomer can comprise a reactive functional group, and wherein one, two, three or all of the following conditions are met: (i) the monomer has a vapor pressure of at most about 8000 Pa at 60° C. in its monomeric state; (ii) following 2 h heating at 90° C., the monomer has a mass loss rate of less than 0.25% per hour at 90° C. in its monomeric state; (iii) the molecular weight of the telechelic polymer is not more than about 50 kDa; and (iv) the reactive functional group comprises a photopolymerizable moiety. In various embodiments, the monomer is a terminal monomer. In various embodiments, the monomer is an internal monomer. In some embodiments, the monomer is an internal and a terminal monomer. In various embodiments, the telechelic polymer is a telechelic block copolymer comprising 2, 3, 4, 5 or more different monomer species. In such instances, a photopolymerizable telechelic block copolymer of the present disclosure can comprise (i) a monomer comprising a reactive functional group that comprises a photopolymerizable moiety, and (ii) can have a molecular weight of at most about 50 kDa, 40 kDa, 30 kDa, 25 kDa, 20 kDa, 15 kDa, 10 kDa, 5 kDa. Further provided herein are curable resins comprising one or more telechelic polymers, as well as polymeric materials that can be produced from such resins by curing (e.g., photo-curing) the same. Such polymeric materials can be used in the fabrications of medical devices, e.g., orthodontic appliances.

All terms, chemical names, expressions and designations have their usual meanings which are well-known to those skilled in the art. As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim.

It is noted that as used herein and in the appended claims, the singular forms "a", "an", and "the" include plural reference unless the context clearly dictates otherwise. Thus, for example, reference to "a polymer" includes a plurality of such polymers and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

The term "about", as used herein, and unless clearly indicated otherwise, generally refers to and encompasses plus or minus 10% of the indicated numerical value(s). For example, "about 10%" may indicate a range of 9% to 11%, and "about 1" may include the range 0.9-1.1. Number ranges are to be understood as inclusive, i.e. including the indicated lower and upper limits.

As used herein, the terms "telechelic polymer" and "telechelic oligomer" generally refer to a polymer or oligomer the molecules of which are capable of entering, through reactive groups, into further polymerization.

Oligomer and polymer mixtures can be characterized and differentiated from other mixtures of oligomers and polymers by measurements of molecular weight and molecular weight distributions.

Unless otherwise specified herein, the molecular weight of a telechelic polymer refers to the average molecular weight (M) of the telechelic polymer herein, which is the average number of repeating units n times the molecular weight or molar mass ($M_i$) of the repeating unit. The number-average molecular weight ($M_n$) is the arithmetic mean, representing the total weight of the molecules present divided by the total number of molecules.

As used herein, the term "polymer" generally refers to a molecule composed of repeating structural units connected by covalent chemical bonds and characterized by a substantial number of repeating units (e.g., equal to or greater than 20 repeating units and often equal to or greater than 100 repeating units and often equal to or greater than 200 repeating units) and a molecular weight greater than or equal to 5,000 Daltons (Da) or 5 kDa, such as greater than or equal to 10 kDa, 15 kDa, 20 kDa, 30 kDa, 40 kDa, 50 kDa, or 100 kDa. Polymers are commonly the polymerization product of one or more monomer precursors. The term polymer includes homopolymers, i.e., polymers consisting essentially of a single repeating monomer species. The term polymer also includes copolymers which are formed when two or more different types of monomers are linked in the same polymer. Copolymers may comprise two or more monomer subunits, and include random, block, alternating, segmented, grafted, tapered and other copolymers. "Cross-linked polymers" refers to polymers having one or multiple links between at least two polymer chains, which can result from multivalent monomers forming cross-linking sites upon polymerization.

As used herein, the term "oligomer" generally refers to a molecule composed of repeating structural units connected by covalent chemical bonds and characterized by a number of repeating units less than that of a polymer (e.g., equal to or less than 10 repeating units) and a lower molecular weight than polymers (e.g., less than 5,000 Da or 2,000 Da). In some case, oligomers may be the polymerization product of one or more monomer precursors. In an embodiment, an oligomer or a monomer cannot be considered a polymer in its own right.

Photoinitiators described in the present disclosure can include those that can be activated with light and initiate polymerization of the polymerizable components of the formulation. A "photoinitiator", as used herein, may generally refer to a compound that can produce radical species and/or promote radical reactions upon exposure to radiation (e.g., UV or visible light).

The term "biocompatible," as used herein, refers to a material that does not elicit an immunological rejection or detrimental effect, referred herein as an adverse immune response, when it is disposed within an in-vivo biological environment. For example, in embodiments a biological marker indicative of an immune response changes less than 10%, or less than 20%, or less than 25%, or less than 40%, or less than 50% from a baseline value when a human or animal is exposed to or in contact with the biocompatible material. Alternatively, immune response may be determined histologically, wherein localized immune response is assessed by visually assessing markers, including immune cells or markers that are involved in the immune response pathway, in and adjacent to the material. In an aspect, a biocompatible material or device does not observably change immune response as determined histologically. In some embodiments, the disclosure provides biocompatible devices configured for long-term use, such as on the order of weeks to months, without invoking an adverse immune response. Biological effects may be initially evaluated by measurement of cytotoxicity, sensitization, irritation and intracutaneous reactivity, acute systemic toxicity, pyrogenicity, subacute/subchronic toxicity and/or implantation. Biological tests for supplemental evaluation include testing for chronic toxicity.

"Bioinert" refers to a material that does not elicit an immune response from a human or animal when it is disposed within an in-vivo biological environment. For example, a biological marker indicative of an immune response remains substantially constant (plus or minus 5% of a baseline value) when a human or animal is exposed to or in contact with the bioinert material. In some embodiments, the disclosure provides bioinert devices.

"Crosslinked polymers," as used herein, generally refers to polymers having one or multiple links between at least two polymer chains, which preferably result from multivalent monomers forming crosslinking sites upon polymerization. In various instances herein, a polymer (e.g., a crosslinked polymer) may be synthesized by polymerizing 2, 3, 4, 5, 10, 15, 20, or more prepolymers or telechelic polymers.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. Specific names of compounds are intended to be exemplary, as it is known that one of ordinary skill in the art can name the same compounds differently.

As used herein, the term "group" may refer to a functional group of a chemical compound. Groups of the present compounds refer to an atom or a collection of atoms that are a part of the compound. Groups of the present disclosure may be attached to other atoms of the compound via one or more covalent bonds. Groups may also be characterized with respect to their valence state. The present disclosure includes groups characterized as monovalent, divalent, trivalent, etc. valence states.

As used herein, the term "substituted" refers to a compound (e.g., an alkyl chain) wherein a hydrogen is replaced by another functional group or atom, as described herein.

As used herein, a broken line in a chemical structure can be used to indicate a bond to the rest of the molecule. For example, 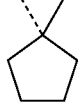 in

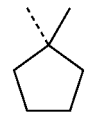

is used to designate the 1-position as the point of attachment of 1-methylcyclopentate to the rest of the molecule. Alternatively,

in, e.g.,

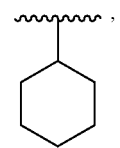

can be used to indicate that the given moiety, the cyclohexyl moiety in this example, is attached to a molecule via the bond that is "capped" with the wavy line.

Alkyl groups include straight-chain, branched and cyclic alkyl groups, unless otherwise defined for a compound or genus of compounds. Alkyl groups include those having from 1 to 30 carbon atoms, unless otherwise defined. Thus, alkyl groups can include small alkyl groups having 1 to 3 carbon atoms, can include medium length alkyl groups having from 4-10 carbon atoms, as well as long alkyl groups having more than 10 carbon atoms, particularly those having 10-30 carbon atoms. The term cycloalkyl specifically refers to an alky group having a ring structure such as ring structure comprising 3-30 carbon atoms, optionally 3-20 carbon atoms and optionally 3-10 carbon atoms, including an alkyl group having one or more rings. Cycloalkyl groups include those having a 3-, 4-, 5-, 6-, 7-, 8-, 9- or 10-member carbon ring(s) and particularly those having a 3-, 4-, 5-, 6-, 7- or 8-member ring(s). The carbon rings in cycloalkyl groups can also carry alkyl groups. Cycloalkyl groups can include bicyclic and tricyclic alkyl groups. Alkyl groups are optionally substituted, as described herein. Substituted alkyl groups can include among others those which are substituted with aryl groups, which in turn can be optionally substituted. Specific alkyl groups include methyl, ethyl, n-propyl, isopropyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Unless otherwise defined herein, substituted alkyl groups include fully halogenated or semihalogenated alkyl groups, such as alkyl groups having one or more hydrogens replaced with one or more fluorine atoms, chlorine atoms, bromine atoms and/or iodine atoms. Thus, substituted alkyl groups can include fully fluorinated or semifluorinated alkyl groups, such as alkyl groups having one or more hydrogens replaced with one or more fluorine atoms. An alkoxy group is an alkyl group that has been modified by linkage to oxygen and can be represented by the formula R—O and can also be referred to as an alkyl ether group. Examples of alkoxy groups include, but are not limited to, methoxy, ethoxy, propoxy, butoxy and heptoxy. Alkoxy groups include substituted alkoxy groups wherein the alky portion of the groups is substituted as provided herein in connection with the description of alkyl groups. As used herein MeO— refers to $CH_3O$—.

Alkenyl groups include straight-chain, branched and cyclic alkenyl groups. Alkenyl groups include those having 1, 2 or more double bonds and those in which two or more of the double bonds are conjugated double bonds. Unless otherwise defined herein, alkenyl groups include those having from 2 to 20 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cycloalkenyl groups include those in which a double bond is in the ring or in an alkenyl group attached to a ring. The term cycloalkenyl specifically refers to an alkenyl group having a ring structure, including an alkenyl group having a 3-, 4-, 5-, 6-, 7-, 8-, 9- or 10-member carbon ring(s) and particularly those having a 3-, 4-, 5-, 6-, 7- or 8-member ring(s). The carbon rings in cycloalkenyl groups can also carry alkyl groups. Cycloalkenyl groups can include bicyclic and tricyclic alkenyl groups. Alkenyl groups are optionally substituted. Unless otherwise defined herein, substituted alkenyl groups include among others those that are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups can include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogen atoms replaced with one or more fluorine atoms.

Aryl groups include groups having one or more 5-, 6-, 7- or 8-membered aromatic rings, including heterocyclic aromatic rings. The term heteroaryl specifically refers to aryl groups having at least one 5-, 6-, 7- or 8-member heterocyclic aromatic rings. Aryl groups can contain one or more fused aromatic rings, including one or more fused heteroaromatic rings, and/or a combination of one or more aromatic rings and one or more nonaromatic rings that may be fused or linked via covalent bonds. Heterocyclic aromatic rings can include one or more N, O, or S atoms in the ring. Heterocyclic aromatic rings can include those with one, two or three N atoms, those with one or two O atoms, and those with one or two S atoms, or combinations of one or two or three N, O or S atoms. Aryl groups are optionally substituted. Substituted aryl groups include among others those that are substituted with alkyl or alkenyl groups, which groups in turn can be optionally substituted. Specific aryl groups include phenyl, biphenyl groups, pyrrolidinyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Aryl groups include, but are not limited to, aromatic group-containing or heterocylic aromatic group-containing groups corresponding to any one of the following: benzene, naphthalene, naphthoquinone, diphenylmethane, fluorene, anthracene, anthraquinone, phenanthrene, tetracene, tetracenedione, pyridine, quinoline, isoquinoline, indoles, isoindole, pyrrole, imidazole, oxazole, thiazole, pyrazole, pyrazine, pyrimidine, purine, benzimidazole, furans, benzofuran, dibenzofuran, carbazole, acridine, acridone, phenanthridine, thiophene, benzothiophene, dibenzothiophene, xanthene, xanthone, flavone, coumarin, azulene or anthracycline. As used herein, a group corresponding to the groups listed above expressly includes an aromatic or heterocyclic aromatic group, including monovalent, divalent and polyvalent groups, of the aromatic and heterocyclic aromatic groups listed herein provided in a covalently bonded configuration in the compounds of the disclosure at any suitable point of attachment. In some embodiments, aryl groups contain between 5 and 30 carbon atoms. In some embodiments, aryl groups contain one aromatic or heteroaromatic six-member ring and one or more additional five- or six-member aromatic or heteroaromatic ring. In embodiments, aryl groups contain between five and eighteen carbon atoms in the rings. Aryl groups optionally have one or more aromatic rings or heterocyclic aromatic rings having one or more electron donating groups, electron withdrawing groups and/or targeting ligands provided as substituents.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl groups having one or more hydrogens replaced with one or more fluorine atoms, chlorine atoms, bromine atoms and/or iodine atoms.

As used herein, the terms "alkylene" and "alkylene group" are used synonymously and refer to a divalent group "—$CH_2$—" derived from an alkyl group as defined herein. The disclosure includes compounds having one or more alkylene groups. Alkylene groups in some compounds function as attaching and/or spacer groups. Compounds of the disclosure may have substituted and/or unsubstituted $C_1$-$C_{20}$ alkylene, $C_1$-$C_{10}$ alkylene and $C_1$-$C_6$ alkylene groups.

As used herein, the terms "cycloalkylene" and "cycloalkylene group" are used synonymously and refer to a divalent group derived from a cycloalkyl group as defined herein. The disclosure includes compounds having one or more cycloalkylene groups. Cycloalkyl groups in some compounds function as attaching and/or spacer groups. Compounds of the disclosure may have substituted and/or unsubstituted $C_3$-$C_{20}$ cycloalkylene, $C_3$-$C_{10}$ cycloalkylene and $C_3$-$C_5$ cycloalkylene groups.

As used herein, the terms "arylene" and "arylene group" are used synonymously and refer to a divalent group derived from an aryl group as defined herein. The disclosure includes compounds having one or more arylene groups. In some embodiments, an arylene is a divalent group derived from an aryl group by removal of hydrogen atoms from two intra-ring carbon atoms of an aromatic ring of the aryl group. Arylene groups in some compounds function as attaching and/or spacer groups. Arylene groups in some compounds function as chromophore, fluorophore, aromatic antenna, dye and/or imaging groups. Compounds of the disclosure include substituted and/or unsubstituted $C_3$-$C_{30}$ arylene, $C_3$-$C_{20}$ arylene, $C_3$-$C_{10}$ arylene and $C_1$-$C_5$ arylene groups.

As used herein, the terms "heteroarylene" and "heteroarylene group" are used synonymously and refer to a divalent group derived from a heteroaryl group as defined herein. The disclosure includes compounds having one or more heteroarylene groups. In some embodiments, a heteroarylene is a divalent group derived from a heteroaryl group by removal of hydrogen atoms from two intra-ring carbon atoms or intra-ring nitrogen atoms of a heteroaromatic or aromatic ring of the heteroaryl group. Heteroarylene groups in some compounds function as attaching and/or spacer groups. Heteroarylene groups in some compounds function as chromophore, aromatic antenna, fluorophore, dye and/or imaging groups. Compounds of the disclosure include substituted and/or unsubstituted $C_3$-$C_{30}$ heteroarylene, $C_3$-$C_{20}$ heteroarylene, $C_1$-$C_{10}$ heteroarylene and $C_3$-$C_5$ heteroarylene groups.

As used herein, the terms "alkenylene" and "alkenylene group" are used synonymously and refer to a divalent group derived from an alkenyl group as defined herein. The invention includes compounds having one or more alkenylene groups. Alkenylene groups in some compounds function as attaching and/or spacer groups. Compounds of the disclosure include substituted and/or unsubstituted $C_2$-$C_{20}$ alkenylene, $C_2$-$C_{10}$ alkenylene and $C_2$-$C_5$ alkenylene groups.

As used herein, the terms "cycloalkenylene" and "cycloalkenylene group" are used synonymously and refer to a divalent group derived from a cycloalkenyl group as defined herein. The disclosure includes compounds having one or more cycloalkenylene groups. Cycloalkenylene groups in some compounds function as attaching and/or spacer groups. Compounds of the disclosure include substituted and/or unsubstituted $C_3$-$C_{20}$ cycloalkenylene, $C_3$-$C_{10}$ cycloalkenylene and $C_3$-$C_5$ cycloalkenylene groups.

As used herein, the terms "alkynylene" and "alkynylene group" are used synonymously and refer to a divalent group derived from an alkynyl group as defined herein. The disclosure includes compounds having one or more alkynylene groups. Alkynylene groups in some compounds function as attaching and/or spacer groups. Compounds of the disclosure include substituted and/or unsubstituted $C_2$-$C_{20}$ alkynylene, $C_2$-$C_{10}$ alkynylene and $C_2$-$C_5$ alkynylene groups.

As used herein, the terms "halo" and "halogen" can be used interchangeably and refer to a halogen group such as a fluoro (—F), chloro (—Cl), bromo (—Br) or iodo (—I)

The term "heterocyclic" refers to ring structures containing at least one other kind of atom, in addition to carbon, in the ring. Examples of such heteroatoms include nitrogen, oxygen and sulfur. Heterocyclic rings include heterocyclic alicyclic rings and heterocyclic aromatic rings. Examples of heterocyclic rings include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups. Atoms of heterocyclic rings can be bonded to a wide range of other atoms and functional groups, for example, provided as substituents.

The term "carbocyclic" refers to ring structures containing only carbon atoms in the ring. Carbon atoms of carbocyclic rings can be bonded to a wide range of other atoms and functional groups, for example, provided as substituents.

The term "alicyclic ring" refers to a ring, or plurality of fused rings, that is not an aromatic ring. Alicyclic rings include both carbocyclic and heterocyclic rings.

The term "aromatic ring" refers to a ring, or a plurality of fused rings, that includes at least one aromatic ring group. The term aromatic ring includes aromatic rings comprising carbon, hydrogen and heteroatoms. Aromatic ring includes carbocyclic and heterocyclic aromatic rings. Aromatic rings are components of aryl groups.

The term "fused ring" or "fused ring structure" refers to a plurality of alicyclic and/or aromatic rings provided in a fused ring configuration, such as fused rings that share at least two intra ring carbon atoms and/or heteroatoms.

As used herein, the term "alkoxyalkyl" refers to a substituent of the formula alkyl-O-alkyl.

As used herein, the term "polyhydroxyalkyl" refers to a substituent having from 2 to 12 carbon atoms and from 2 to 5 hydroxyl groups, such as the 2,3-dihydroxypropyl, 2,3,4-trihydroxybutyl or 2,3,4,5-tetrahydroxypentyl residue.

As used herein, the term "polyalkoxyalkyl" refers to a substituent of the formula alkyl-(alkoxy)$_n$-alkoxy wherein n is an integer from 1 to 10, e.g., 1 to 4, and in some embodiments 1 to 3.

The term "heteroalkyl", as used herein, generally refers to an alkyl, alkenyl or alkynyl group as defined herein, wherein at least one carbon atom of the alkyl group is replaced with a heteroatom. In some instances, heteroalkyl groups may contain from 1 to 18 non-hydrogen atoms (carbon and heteroatoms) in the chain, or from 1 to 12 non-hydrogen atoms, or from 1 to 6 non-hydrogen atoms, or from 1 to 4 non-hydrogen atoms. Heteroalkyl groups may be straight or branched, and saturated or unsaturated. Unsaturated heteroalkyl groups have one or more double bonds and/or one or more triple bonds. Heteroalkyl groups may be unsubstituted or substituted. Exemplary heteroalkyl groups include, but are not limited to, alkoxyalkyl (e.g., methoxymethyl), and aminoalkyl (e.g., alkylaminoalkyl and dialkylaminoalkyl). Heteroalkyl groups may be optionally substituted with one or more substituents.

As to any of the groups described herein that contain one or more substituents, it is understood that such groups do not contain any substitution or substitution patterns which are sterically impractical and/or synthetically non-feasible. In addition, the compounds of this disclosure include all stereochemical isomers arising from the substitution of these compounds.

Unless otherwise defined herein, optional substituents for any alkyl, alkenyl and aryl group includes substitution with one or more of the following substituents, among others:

halogen, including fluorine, chlorine, bromine or iodine;
pseudohalides, including —CN, —OCN (cyanate), —NCO (isocyanate), —SCN (thiocyanate) and —NCS (isothiocyanate);
—COOR, where R is a hydrogen or an alkyl group or an aryl group and more specifically where R is a methyl, ethyl, propyl, butyl, or phenyl group all of which groups are optionally substituted;
—COR, where R is a hydrogen or an alkyl group or an aryl group and more specifically where R is a methyl, ethyl, propyl, butyl, or phenyl group all of which groups are optionally substituted;
—CON(R)$_2$, where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;
—OCON(R)$_2$, where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;
—N(R)$_2$, where each R, independently of each other R, is a hydrogen, or an alkyl group, or an acyl group or an aryl group and more specifically where R is a methyl, ethyl, propyl, butyl, phenyl or acetyl group, all of which are optionally substituted; and where R and R can form a ring that can contain one or more double bonds and can contain one or more additional carbon atoms;
—SR, where R is hydrogen or an alkyl group or an aryl group and more specifically where R is hydrogen, methyl, ethyl, propyl, butyl, or a phenyl group, which are optionally substituted;
—SO$_2$R, or —SOR, where R is an alkyl group or an aryl group and more specifically where R is a methyl, ethyl, propyl, butyl, or phenyl group, all of which are optionally substituted;
—OCOOR, where R is an alkyl group or an aryl group;
—SO$_2$N(R)$_2$, where each R, independently of each other R, is a hydrogen, or an alkyl group, or an aryl group all of which are optionally substituted and wherein R and R can form a ring that can contain one or more double bonds and can contain one or more additional carbon atoms; and —OR, where R is H, an alkyl group, an aryl group, or an acyl group all of which are optionally substituted. In a particular example R can be an acyl yielding —OCOR", wherein R" is a hydrogen or an alkyl group or an aryl group and more specifically where R" is methyl, ethyl, propyl, butyl, or phenyl groups all of which groups are optionally substituted.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups; and methoxyphenyl groups, particularly 4-methoxyphenyl groups.

As to any of the above groups that contain one or more substituents, it is understood that such groups do not contain any substitution or substitution patterns which are sterically impractical and/or synthetically non-feasible. In addition, the compounds of this disclosure include all stereochemical isomers arising from the substitution of these compounds.

II. Telechelic Block Copolymers

The present disclosure provides telechelic polymers and compositions (e.g., resins) comprising such telechelic polymers. In various instances, provided herein are telechelic polymers (i.e., polymers consisting of a single monomer species A) and telechelic copolymers (i.e., polymers comprising 2, 3, 4, 5, or more different monomer species). In various cases, the telechelic copolymers described herein are telechelic block copolymers in which each monomer species is present in a "block" configuration within the copolymer structure. As further described herein, such block configuration can yield various polymer configurations, e.g., in cases where a telechelic block copolymer comprises 2 different monomer species A and B, block configurations such as AB, ABA, ABAB, AABB, etc. are possible.

Thus, throughout the present disclosure, the term "telechelic polymer" is further defined to include polymers consisting of (i) only one monomer species, and (ii) copolymers comprising 2, 3, 4, 5 or more different species of monomers. Such copolymers can be block copolymers as described herein. Furthermore, the term "telechelic," as used herein in the context of polymers and block copolymers, generally refers to a polymer or oligomer capable of undergoing further polymerization through its reactive functional groups at its termini. As used herein, a telechelic polymer is generally characterized by a number-average molecular weight of at most about 50 kDa, 40 kDa, 30 kDa, 25 kDa, 20 kDa, or 15 kDa. Thus, in various instances, a telechelic block copolymer of this disclosure is capable of undergoing photopolymerization with one or more other telechelic polymers, telechelic block copolymers, telechelic oligomers, or monomers (e.g., a reactive diluents) via its monomers. In various cases, the monomers comprise a photo-reactive moiety enabling further photo-polymerization reactions. Such photo-polymerization reaction of a telechelic block copolymer with other polymers, oligomers and/or monomers can occur during photo-curing, e.g., in instances where these components are part of a photo-curable resin as further described herein.

As further described herein, a telechelic polymer (e.g., a telechelic block copolymer) of the present disclosure can enhance polymerization-induced phase separation (e.g., into one or more crystalline and/or amorphous phases) in a polymeric material into which the telechelic polymer is incorporated during, e.g., photo-curing. Hence, in some instances, a telechelic polymer herein can be used to control, at least in part, the number and/or sizes of the phase domains formed in a polymeric material upon photo-curing, and thereby provide materials with certain advantageous properties as described herein. Such phase control can be used to modify the transparency or clarity as well as the physical and mechanical properties of the resulting polymeric material. Furthermore, the chemical structure, monomer block configuration (e.g., AB, ABA, ABAB, etc.), and molecular weight of a telechelic polymer comprising 2 monomer species A and B can allow for controlling the morphology and properties of the resulting polymeric material into which the telechelic polymer in integrated.

The present disclosure provides telechelic polymers comprising a monomer, wherein the monomer comprises a reactive functional group (e.g., when at a terminal position of the telechelic polymer or in polymerized form when at an internal position of the telechelic polymer), and wherein one, two, three or all of the following conditions are met: (i) the monomer has a vapor pressure of at most about 8000 Pa at 60° C. in its monomeric state; (ii) following 2 h heating at 90° C., the monomer has a mass loss rate of less than 0.25% per hour at 90° C. in its monomeric state; (iii) the molecular weight of the telechelic polymer is not more than about 50 kDa; and (iv) the reactive functional group comprises a photopolymerizable moiety. In some cases, (i) the monomer has a vapor pressure of at most about 8000 Pa at 60° C. in its monomeric state and (ii) following 2 h heating at 90° C., the monomer has a mass loss rate of less than 0.25% per hour at 90° C. in its monomeric state. In some cases, (i) the monomer has a vapor pressure of at most about 8000 Pa at 60° C. in its monomeric state and (iii) the molecular weight of the telechelic polymer is not more than about 50 kDa. In some cases, (i) the monomer has a vapor pressure of at most about 8000 Pa at 60° C. in its monomeric state and (iv) the reactive functional group comprises a photopolymerizable moiety. In some cases, (ii) following 2 h heating at 90° C., the monomer has a mass loss rate of less than 0.25% per hour at 90° C. in its monomeric state; (iii) the molecular weight of the telechelic polymer is not more than about 50 kDa. In some cases, (ii) following 2 h heating at 90° C., the monomer has a mass loss rate of less than 0.25% per hour at 90° C. in its monomeric state; and (iv) the reactive functional group comprises a photopolymerizable moiety. In some cases, (iii) the molecular weight of the telechelic polymer is not more than about 50 kDa and (iv) the reactive functional group comprises a photopolymerizable moiety. In some cases, (i) the monomer has a vapor pressure of at most about 8000 Pa at 60° C. in its monomeric state; (ii) following 2 h heating at 90° C., the monomer has a mass loss rate of less than 0.25% per hour at 90° C. in its monomeric state; and (iii) the molecular weight of the telechelic polymer is not more than about 50 kDa. In some cases, (i) the monomer has a vapor pressure of at most about 8000 Pa at 60° C. in its monomeric state; (ii) following 2 h heating at 90° C., the monomer has a mass loss rate of less than 0.25% per hour at 90° C. in its monomeric state; and (iv) the reactive functional group comprises a photopolymerizable moiety. In some cases, (i) the monomer has a vapor pressure of at most about 8000 Pa at 60° C. in its monomeric state; (iii) the molecular weight of the telechelic polymer is not more than about 50 kDa; and (iv) the reactive functional group comprises a photopolymerizable moiety. In some cases, (ii) following 2 h heating at 90° C., the monomer has a mass loss rate of less than 0.25% per hour at 90° C. in its monomeric state; (iii) the molecular weight of the telechelic polymer is not more than about 50 kDa; and (iv) the reactive functional group comprises a photopolymerizable moiety. In some cases, (i) the monomer has a vapor pressure of at most about 8000 Pa at 60° C. in its monomeric state; (ii) following 2 h heating at 90° C., the monomer has a mass loss rate of less than 0.25% per hour at 90° C. in its monomeric state; (iii) the molecular weight of the telechelic polymer is not more than about 50 kDa; and (iv) the reactive functional group comprises a photopolymerizable moiety.

In some embodiments, a monomer that can be part of a telechelic polymer, can, in its monomeric state, have a vapor pressure from about 0.1 Pa to about 20 Pa at 60° C. (e.g., when the monomer is in at least 98% pure form). In some instances, a monomer can have a vapor pressure, at about 60° C., from 0.1 Pa to 1 Pa, from about 0.5 Pa to about 5, from about 1 Pa to about 5 Pa, from about 2 Pa to about 5 Pa, from about 2 Pa to about 5 Pa, from about 10 Pa to about 200 Pa, from about 50 Pa to about 300 Pa, from about 100 Pa to about 500 Pa, from about 200 Pa to about 800 Pa, from about 500 Pa to about 3000 Pa, from about 1000 to about 5000 Pa, or from about 2000 to about 8000 Pa. In some instances, a monomer that can be part of a telechelic polymer, can, following 2 h heating at 90° C., have a mass loss rate from about 0.005% to about 0.5% per hour at 90° C. in its monomeric state. In some cases, a monomer can have a mass loss rate from about 0.0-5% to about 0.05%, from about 0.025% to about 0.075%, from about 0.025% to about 0.125%, or from about 0.05% to about 0.225% at 90° C. in its monomeric state following 2 h heating at 90° C. for 2 h. In some embodiments of this disclosure, a monomer can, in its monomeric state, have a melting point of at least about 25° C., 30° C., 35° C., 40° C., 45° C., or 50° C. In some cases, a monomer has a melting point of at least 25° C. in its monomeric state.

A telechelic polymer of the present disclosure can comprise a range of degrees of terminal functionalization. In some cases, a population of telechelic polymers has complete or close to complete terminal substitution (e.g., by an acrylate or methacrylate moiety). For example, the population of telechelic polymers can have greater than 95%, greater than 97.5%, or greater than 99% terminal substitution. In some cases, the population of telechelic polymers has partial terminal substitution, for example between 60% and 95%, between 70% and 90%, between 80% and 95%, between 75% and 85%, or between 60% and 80%. In some cases, the terminal substitution of the population of telechelic polymers is greater than 95%, greater than 90%, greater than 80%, greater than 70%, greater than 60%, or greater than 50%. In some cases in which partial terminal substitution is optimal, the terminal substitution of the population of telechelic polymers is at most 90%, at most 85%, at most 80%, at most 70%, or at most 60%.

A telechelic polymer described herein can comprise a monomer comprising a photo-reactive moiety. Such photo-reactive moiety located at a terminus (or both termini) of the telechelic polymer can enable any photoreaction with other polymers or monomers known in art, including but not limited to, free-radical photopolymerization, photo-induced Diels-Alder click reaction or a photodimerization reaction. In some instances, the photopolymerizable moiety that is part of the monomer can comprise an acrylate, methacrylate, vinyl acrylate, vinyl methacrylate, allyl ether, silene, alkyne, alkene, vinyl ether, maleimide, fumarate, maleate, itoconate, epoxide, oxetane, thiol, or styrenyl moiety. In various instances, the photopolymerizable moiety comprises an acrylate, methacrylate, vinyl acrylate, vinyl methacrylate, allyl ether, alkyne, alkene, vinyl ether, or styrenyl moiety. In various instances, the photopolymerizable moiety comprises an acrylate, methacrylate, vinyl acrylate, vinyl methacrylate, allyl ether, vinyl ether, or alkene moiety. In various instances, the photopolymerizable moiety comprises an acrylate or methacrylate moiety. In some embodiments, a photo-reactive Diels-Alder functional moiety can include furans, maleimides, conjugated alkylenes, pentadienes, carbonyls, anthracenes, etc. In further embodiments, the monomer can be photodimerizable. A photodimerizable functional moiety can include an uracil, a thymine, a maleimide, a coumarin, an anthracene, an acenaphtalenes, or a maleate moiety. In other instances, other photoreactive moieties can be comtemplated such as carnenes and nitrenes.

In various embodiments, a monomer of the present disclosure, in its monomeric form, can be a compound according to Formula (I):

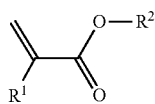

(I)

wherein,
R$^1$ is H, substituted or unsubstituted C$_{1-3}$ alkyl, or halogen; and
R$^2$ is substituted or unsubstituted C$_{1-6}$ alkyl, substituted or unsubstituted C$_{1-6}$ heteroalkyl, substituted or unsubstituted C$_{1-6}$ carbonyl, substituted or unsubstituted C$_{1-6}$ carboxy, substituted or unsubstituted aryl, substituted or unsubstituted heteroaryl, substituted or unsubstituted cyclo(C$_{3-8}$) alkyl, or substituted or unsubstituted cyclo (C$_{3-8}$) heteroalkyl.

In some instances, le is H or C$_1$-C$_3$ alkyl. In some instances, le is H or methyl. In some instances, R$^2$ is substituted or unsubstituted C$_{1-6}$ alkyl, substituted or unsubstituted C$_{1-6}$ carbonyl, substituted or unsubstituted aryl, substituted or unsubstituted heteroaryl, substituted or unsubstituted cyclo(C$_{3-8}$) alkyl, or substituted or unsubstituted cyclo(C$_{3-8}$) heteroalkyl. In some instances, R$^2$ is substituted or unsubstituted C$_{1-6}$ alkyl, substituted or unsubstituted C$_{1-6}$ carbonyl, or substituted or unsubstituted aryl. In some instances, R$^2$ is unsubstituted C$_{1-6}$ alkyl, unsubstituted C$_{1-6}$ carbonyl, or unsubstituted aryl. In some instances, R$^2$ is C$_{1-6}$ alkyl, C$_{1-6}$ heteroalkyl, substituted or unsubstituted aryl, or substituted or unsubstituted heteroaryl. In some cases, R$^2$ is substituted with one or more instances of halogen, —OH, —NH$_2$, —NH(C$_1$-C$_3$ alkyl), —N(C$_1$-C$_3$ alkyl)(C$_1$-C$_3$ alkyl), C$_1$-C$_3$ alkyl, or a combination thereof. In some cases, R$^2$ is substituted with one or more instances of halogen, —OH, —NH$_2$, or a combination thereof. In some cases, R$^2$ is substituted with one instance of halogen, —OH, or —NH$_2$.

In some embodiments, a second telechelic polymer can comprise a second monomer that is different from the monomer according to Formula (I) of a (first) telechelic polymer. In such instances, the second monomer can be a compound according to Formula (II):

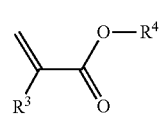

(II)

wherein,
R$^3$ is H, substituted or unsubstituted C$_{1-3}$ alkyl or halogen; and
R$^4$ is substituted or unsubstituted C$_{1-6}$ alkyl, substituted or unsubstituted C$_{1-6}$ heteroalkyl, substituted or unsubstituted C$_{1-6}$ carbonyl, substituted or unsubstituted C$_{1-6}$ carboxy, substituted or unsubstituted aryl, substituted or unsubstituted heteroaryl, substituted or unsubstituted cyclo(C$_{3-8}$) alkyl, or substituted or unsubstituted cyclo (C$_{3-8}$) heteroalkyl.

In some instances, R$^3$ is H or C$_1$-C$_3$ alkyl. In some instances, R$^3$ is H or methyl. In some instances, R$^3$ is H. In some instances, R$^3$ is methyl.

In some instances, R$^4$ is substituted or unsubstituted C$_{1-6}$ alkyl, substituted or unsubstituted C$_{1-6}$ carbonyl, substituted or unsubstituted aryl, substituted or unsubstituted heteroaryl, substituted or unsubstituted cyclo(C$_{3-8}$) alkyl, or substituted or unsubstituted cyclo(C$_{3-8}$) heteroalkyl. In some instances, R$^4$ is substituted or unsubstituted C$_{1-6}$ alkyl, substituted or unsubstituted C$_{1-6}$ carbonyl, or substituted or unsubstituted aryl. In some instances, R$^4$ is unsubstituted C$_{1-6}$ alkyl, unsubstituted C$_{1-6}$ carbonyl, or unsubstituted aryl. In some instances, R$^4$ is C$_{1-6}$ alkyl, C$_{1-6}$ heteroalkyl, substituted or unsubstituted aryl, or substituted or unsubstituted heteroaryl. In some cases, R$^4$ is substituted with one or more instances of halogen, —OH, —NH$_2$, —NH(C$_1$-C$_3$ alkyl), —N(C$_1$-C$_3$ alkyl)(C$_1$-C$_3$ alkyl), C$_1$-C$_3$ alkyl, or a combination thereof. In some cases, R$^4$ is substituted with one or more instances of halogen, —OH, —NH$_2$, or a combination thereof. In some cases, R$^4$ is substituted with one instance of halogen, —OH, or —NH$_2$.

In some cases, an internal monomer of a telechelic polymer can be a compound according to Formula (I), Formula (II), or a combination thereof. For example, a telechelic polymer of the present disclosure can comprise, in polymerized form, 50 repeating units of a compound according to Formula (I), as well as reactive terminal monomers, such as acrylate or methacrylate moieties.

In other instances, and as an alternative to monomers according to Formulas (I) and (II), a telechelic polymer or block copolymer described herein can comprise or consist of structurally modified or unmodified styrene monomers, structurally modified or unmodified vinyl monomers, structurally modified or unmodified epoxy monomers, structurally modified or unmodified urethane monomers, structurally modified or unmodified urea monomers, structurally modified or unmodified amide monomers, structurally modified or unmodified imide monomers, structurally modified or unmodified carbonate monomers, structurally modified or unmodified olefin monomers, structurally modified or unmodified acetal monomers, structurally modified or unmodified diene monomers, structurally modified or unmodified ester monomers, structurally modified or unmodified ether monomers, or a combination thereof. In some cases, the telechelic polymer or block copolymer described herein can comprise or consist of structurally modified or unmodified styrene monomers, structurally modified or unmodified vinyl monomers, or a combination thereof.

In various embodiments, a telechelic polymer herein is a telechelic block copolymer comprising 2 species of different monomers A and B and hence 2 different monomers, e.g., in a AB or ABAB block configuration. In other instances, a composition (e.g., a photo-curable composition) herein comprises a first telechelic polymer consisting of a single monomer species A, and thus comprising a first monomer A, and a second telechelic polymer consisting of a single monomer species B and comprising a second monomer B. In each of the above embodiments, the different monomers can be compounds according to Formula (I).

In various instances, a telechelic polymer such as a telechelic block copolymer provided herein can have a molecular weight greater than about 5 kDa, 6 kDa, 7 kDa, 8 kDa, 9 kDa, 10 kDa, 11 kDa, 12 kDa, 13 kDa, 14 kDa, 15 kDa, 16 kDa, 17 kDa, 18 kDa, 19 kDa, 20 kDa, 21 kDa, 22 kDa, 23 kDa, 24 kDa, 25 kDa, 30 kDa, 35 kDa, 40 kDa or greater than about 45 kDa but no greater than about 50 kDa. In such instances, a telechelic polymer provided herein can have a molecular weight from about 5 kDa to about 40 kDa, from about 5 kDa to about 30 kDa, from about 5 kDa to about 20 kDa, or from about 5 kDa to about 15 kDa. In various instances, a telechelic polymer such as a telechelic block copolymer has a molecular weight from about 5 kDa to about 25 kDa or from about 5 kDa to about 15 kDa. As further described herein, the telechelic polymers provided herein include photopolymerizable telechelic polymers and photopolymerizable telechelic block copolymers. A telechelic polymer can comprise or consist of a single monomer species. A telechelic block copolymer herein can comprise or consist of 2, 3, 4, 5 or more different (e.g., chemically different) monomer species.

In such instances, a telechelic polymer described herein can comprise a monomer A. Such telechelic polymer can be described as $A_x$, wherein x denotes a number of copies of monomer A in the telechelic polymer, and is a positive integer of 1-10, 1-20, 1-50, 1-100, 1-200, 1-500 or 1-1000, or a positive integer of at least about 5, 10, 15, 20, 25, 30, 40, 50, 75, or at least about 100. In instances where the telechelic polymer is a block copolymer comprising 2 different monomer species A and B, such block copolymer can consist of or comprise a block configuration of $A_xB_y$ or $A_xB_yA_z$, and multiples thereof, wherein x, y, and z denote numbers of the monomers A, B, and A, respectively, and are independently positive integers of 1-10, 1-20, 1-50, 1-100, 1-200, 1-500 or 1-1000, or positive integer of at least about 5, 10, 15, 20, 25, 30, 40, 50, 75, or at least about 100. In instances where a telechelic block copolymer comprises 3 different monomers A, B and C, such block copolymer can consist of or comprise a block configuration of $A_xB_yC_z$, wherein x, y, and z denote copy numbers of the monomers A, B, and C, respectively, and are independently positive integers of 1-10, 1-20, 1-50, 1-100, 1-200, 1-500 or 1-1000, or positive integer of at least about 5, 10, 15, 20, 25, 30, 40, 50, 75, or at least about 100. Generally, a telechelic block copolymer of the present disclosure can comprise a plurality (e.g., 2, 3, 4, 5, 6, 7, 8, 9, 10 or more) of different monomer species, wherein such different monomer species can form monomer blocks within the polymer chain, and wherein the telechelic block copolymer can comprise one or more blocks of a specific monomer species.

In instances where the telechelic polymer $A_x$ consists of a single species of monomer A, and x is a positive integer of >1, the monomers (at both termini) of such polymer are identical to all other monomers present in the polymer. In instances where the telechelic polymer is a telechelic block copolymer that consists of 2 different monomer species A and B and a block configuration of $A_xB_y$, and wherein x and y are independently positive integers of 1-50, such telechelic polymer comprises two monomers A and B that are different, one at each terminus. In some instances, such different monomers A and B can comprise the same or different photo-reactive moieties. In some cases, such photo-reactive moieties can be acrylate or methacrylate moieties, or derivatives thereof. In yet other instances where the telechelic polymer is a telechelic block copolymer that consists of a block configuration of $A_xB_yA_z$, and wherein x, y, and z are independently positive integers of 1-50, such telechelic polymer comprises two identical monomers A when the photo-reactive moieties of such monomers are also identical. In some cases, such photo-reactive moieties can be acrylate or methacrylate moieties, or derivatives thereof.

In some embodiments, a telechelic polymer is a telechelic block copolymer having a block configuration of $A_nB_m$. Such telechelic block copolymer can be a compound according to Formula (III):

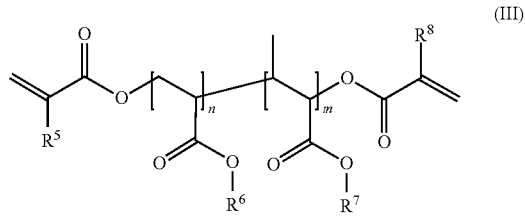

(III)

wherein,
$R^5$ and $R^8$ are independently H, substituted or unsubstituted $C_{1-3}$ alkyl, or halogen;
$R^6$ and $R^7$ are independently substituted or unsubstituted $C_{1-6}$ alkyl, substituted or unsubstituted $C_{1-6}$ heteroalkyl, substituted or unsubstituted $C_{1-6}$ carbonyl, substituted or unsubstituted $C_{1-6}$ carboxy, substituted or unsubstituted aryl, substituted or unsubstituted heteroaryl, substituted or unsubstituted cyclo($C_{3-8}$) alkyl, or substituted or unsubstituted cyclo($C_{3-8}$) heteroalkyl, and $R^6 \neq R^7$; and
n and m are independently positive integers from 1 to 300. In some cases, n and m are independently positive integers from 1 to 100.

In some embodiments, $R^5$ and $R^8$ are independently H or $C_1$-$C_3$ alkyl. In some embodiments, $R^5$ and $R^8$ can independently be H or methyl. In some instances, $R^5$ and $R^8$ are identical. In other cases, $R^5$ and $R^8$ are different. In some aspects, $R^6$ and $R^7$ are independently selected from the group consisting of substituted or unsubstituted $C_{1-6}$ alkyl, substituted or unsubstituted $C_{1-6}$ heteroalkyl, substituted or unsubstituted aryl, and substituted or unsubstituted heteroaryl, and n and m are independently positive integers from about 10 to about 50. In some cases, $R^6$ and $R^7$ are independently substituted or unsubstituted $C_{1-6}$ alkyl or substituted or unsubstituted aryl. In some cases, $R^6$ and $R^7$ are independently unsubstituted $C_{1-6}$ alkyl or unsubstituted aryl. In some cases, $R^6$, $R^7$, or a combination thereof are independently substituted with one or more instances of halogen, —OH, —NH$_2$, —NH($C_1$-$C_3$ alkyl), —N($C_1$-$C_3$ alkyl)($C_1$-$C_3$ alkyl), $C_1$-$C_3$ alkyl, or a combination thereof. In some cases, $R^6$, $R^7$, or a combination thereof are independently substituted with one or more instances of halogen, —OH, —NH$_2$, or a combination thereof. In some cases, $R^6$, $R^7$, or a combination thereof are independently substituted with one instance of halogen, —OH, or —NH$_2$.

In some embodiments, a telechelic polymer herein can further comprise a macro-initiator. Such macro-initiator can be used to initiate a polymerization reaction, e.g., to produce the telechelic polymer or telechelic block copolymer. In some instances, the macro-initiator is a polycaprolactone (e.g., having a molecular weight of about 2000-10000 g/mol), a polytetra-hydrofuran (e.g., having a molecular weight of about 2000-10000 g/mol), a hydrogenated polyethylene, a hydroxy terminated polystyrene, a polyester diol, a polycarbonate diol, or a polystyrene dihalide. Three telechelic block copolymer macro-initiators consistent with the present disclosure are outlined in SCHEME 3:

In some embodiments, a telechelic polymer can be a compound according to Formula (IV):

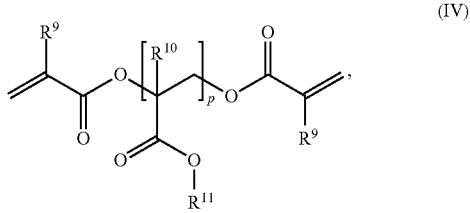

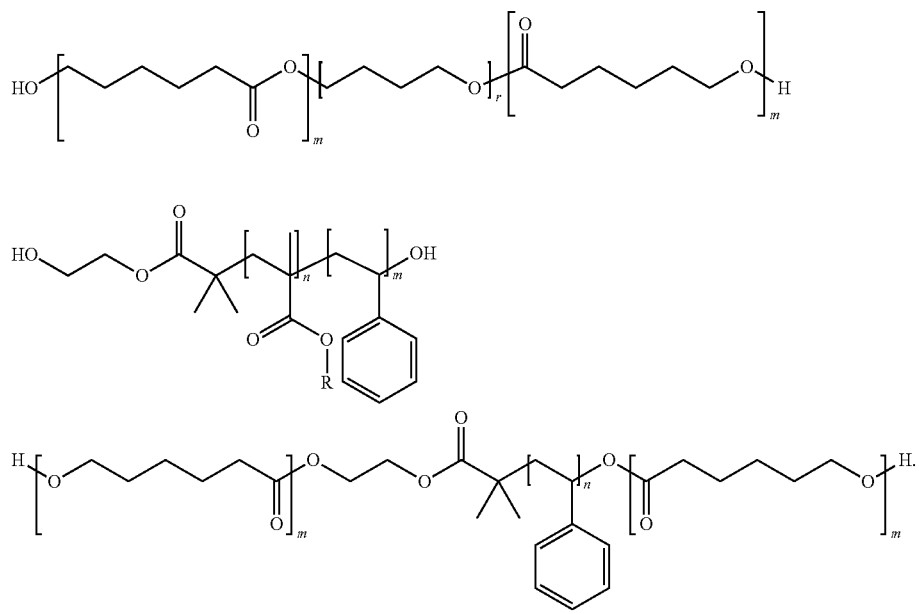

A polymer diol, such as polytetrahydrofuran, can be used to initiate ring-opening polymerization of lactones, such as caprolactone, to synthesize polyester-polyether-polyester BAB triblock copolymers. Polystyrene synthesized by atom transfer radical polymerization can be end-functionalized to have a hydroxy group, which can also further initiate polymerization to synthesize block copolymers from vinyl monomers and from lactones.

In some instances, a telechelic polymer described herein can be characterized by a polydispersity index (PDI). In some cases, a telechelic polymer described herein can have a PDI of from about 0.05 to about 0.3, from about 0.1 to about 0.5, from about 0.25 to about 0.75, from about 0.5 to about 5, from about 0.5 to about 3, from about 1 to about 3, or from about 1 to about 2.

A telechelic polymer such as a telechelic block copolymer of the present disclosure can, when integrated into the polymeric structure of a polymeric material during photocuring, modify the physical and/or mechanical properties (e.g., toughness, stress remaining, etc.) of such polymeric material compared to a material that does not comprise such polymer. Hence, in some cases herein, a telechelic polymer of this disclosure can be characterized as a toughness modifier, a glass transition temperature ($T_g$) modifier, or a combination thereof, among other characteristics.

wherein,
each instance of $R^9$ is H, substituted or unsubstituted $C_{1-3}$ alkyl, or halogen;
each instance of $R^{10}$ is H, substituted or unsubstituted $C_{1-3}$ alkyl, or halogen; $R^{11}$ is substituted or unsubstituted $C_{1-6}$ alkyl, substituted or unsubstituted $C_{1-6}$ heteroalkyl, substituted or unsubstituted $C_{1-6}$ carbonyl, substituted or unsubstituted $C_{1-6}$ carboxy, substituted or unsubstituted aryl, substituted or unsubstituted heteroaryl, substituted or unsubstituted cyclo($C_{3-12}$) alkyl, or substituted or unsubstituted cyclo($C_{3-12}$) heteroalkyl; and
p is a positive integer from 1 to 200.

In some cases, each instance of $R^9$ is H or unsubstituted $C_{1-3}$ alkyl. In some cases, each instance of $R^9$ is H or methyl. In some cases, each instance of $R^{10}$ is H or unsubstituted $C_{1-3}$ alkyl. In some cases, each instance of $R^{10}$ is H or methyl.

In some cases, $R^{11}$ is substituted or unsubstituted $C_{1-6}$ alkyl, substituted or unsubstituted aryl, substituted or unsubstituted heteroaryl, substituted or unsubstituted cyclo($C_{3-12}$) alkyl, or substituted or unsubstituted cyclo($C_{3-12}$) heteroalkyl. In some cases, $R^{11}$ is substituted or unsubstituted $C_{1-6}$ alkyl, substituted or unsubstituted cyclo($C_{3-12}$) alkyl, or substituted or unsubstituted cyclo($C_{3-12}$) heteroalkyl. In some cases, $R^{11}$ is substituted or unsubstituted cyclo($C_{3-12}$) alkyl or substituted or unsubstituted cyclo($C_{3-12}$) heteroalkyl. In some cases, $R^{11}$ is substituted or unsubstituted cyclo($C_{3-12}$) alkyl. In some cases, the cyclo($C_{3-12}$) alkyl is bicyclic. In some cases, $R^{11}$ is substituted or unsubstituted and selected from the group consisting of

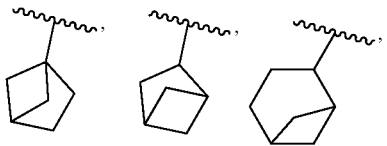

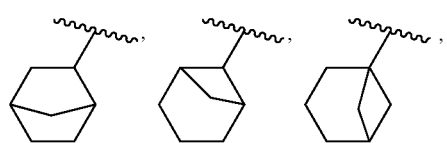

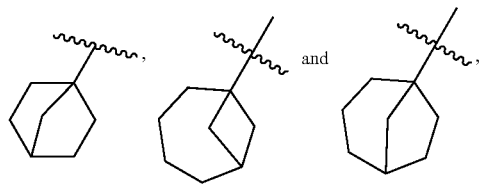

wherein ~~ denotes attachment to the remainder of Formula (IV).

In some cases, $R^{11}$ is substituted or unsubstituted and selected from the group consisting of

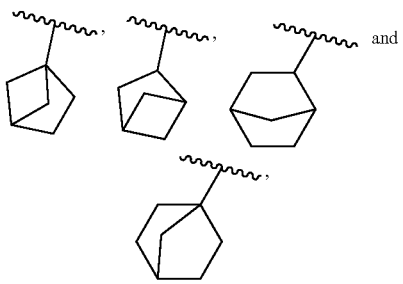

In some cases, $R^{11}$ is substituted or unsubstituted and selected from the group consisting of

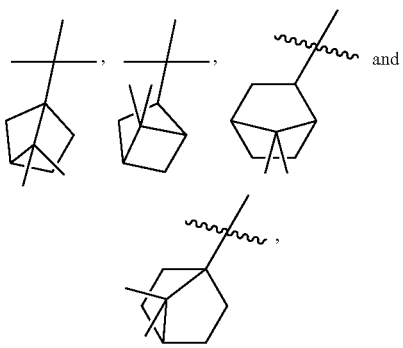

In some cases, $R^{11}$ is substituted or unsubstituted and selected from the group consisting of

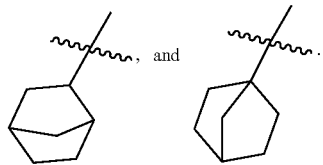 [SMILES: *C1CC2CCC1C2 ; *C12CCC(CC1)C2]

In some cases, $R^{11}$ is substituted or unsubstituted and selected from the group consisting of

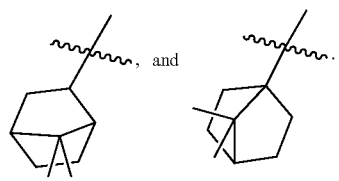

In some cases, $R^{11}$ is selected from the group consisting of

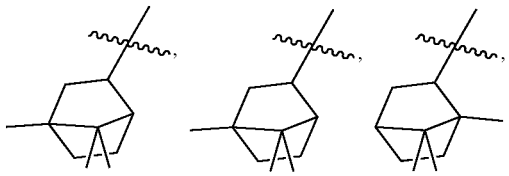

In some cases, $R^{11}$ is

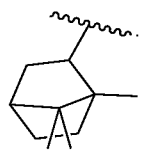 [SMILES: *C1CC2CCC1(C)C2(C)C]

In some cases, $R^{11}$ is substituted with one or more instances of halogen, —OH, —$NH_2$, —NH($C_1$-$C_3$ alkyl), —N($C_1$-$C_3$ alkyl)($C_1$-$C_3$ alkyl), $C_1$-$C_3$ alkyl, or a combination thereof. In some cases, $R^{11}$ is substituted with one or more instances of halogen, —OH, —$NH_2$, $C_1$-$C_3$ alkyl, or a combination thereof. In some cases, $R^{11}$ is substituted with one or more instances of $C_1$-$C_3$ alkyl. In some cases, $R^{11}$ is substituted with one instance of $C_1$-$C_3$ alkyl.

In some cases, p is 10 to 200. In some cases, p is 50 to 200. In some cases, p is 100 to 200. In some cases, p is 5 to 25. In some cases, p is 10 to 50. In some cases, p is 20 to 60. In some cases, p is 30 to 80.

In some embodiments, a telechelic polymer is a telechelic block copolymer having a block configuration of $A_nB_m$. Such telechelic block copolymer can be a compound according to Formula (V):

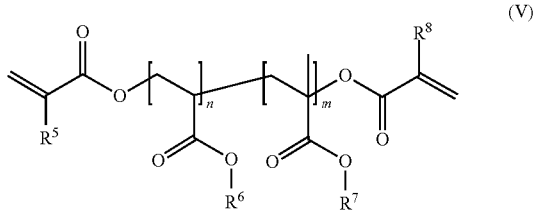

wherein, $R^5$, $R^6$, $R^7$, $R^8$, n, and m are as defined above.

III. Photo-Curable Resins

The present disclosure provides photo-curable resin compositions that can comprise one or more telechelic polymers described herein, e.g., those comprising, in a polymerized form, one or more monomers according to Formulas (I) and (II). Such photo-curable resins can comprise a photopolymerizable (e.g., photo-curable) composition. Such photopolymerizable composition can comprise a photo-polymerizable telechelic polymer (or a plurality of telechelic polymers) as described herein. As further described herein, the telechelic polymer can be a telechelic block copolymer comprising 2, 3, 4, 5, or more different monomer species, e.g., one according to Formula (III). In various instances herein, a photo-curable resin can comprise 1, 2, 3, 4, 5 or more different telechelic polymers and/or telechelic oligomers. One or more of such telechelic polymers can be telechelic block copolymers.

Resin Components

A photo-curable resin of the present disclosure can comprise one or more photo-polymerizable components. Such one or more photo-polymerizable components can include one or more telechelic polymers, e.g., telechelic block copolymers, one or more telechelic oligomers, one or more polymerizable monomers (e.g., reactive diluent(s)), and combinations thereof.

In various cases, a photo-curable resin of the present disclosure can comprise a first telechelic polymer. The first telechelic polymer can comprise a first monomer, wherein the first monomer comprises a first reactive functional group that comprises a first photopolymerizable moiety, and wherein one or more of the following conditions are met: (i) the first monomer has a vapor pressure of at most about 8000 Pa at 60° C. in its monomeric state; (ii) following 2 h heating at 90° C., the first monomer has a mass loss rate of less than about 0.25% per hour at 90° C. in its monomeric state; (iii) the molecular weight of the first telechelic polymer is not more than about 50 kDa; and (iv) the first reactive functional group comprises a first photopolymerizable moiety.

In some instances, a photo-curable resin herein can comprise a second telechelic polymer. The second telechelic polymer can comprise a second monomer, wherein the second monomer comprises a second reactive functional group that comprises a second photopolymerizable moiety, and wherein one or more of the following conditions are met: (v) the second monomer has a vapor pressure of at most about 8000 Pa at 60° C. in its monomeric state; (vi) following 2 h heating at 90° C., the second monomer has a mass loss rate of less than 0.25% per hour at 90° C. in its monomeric state; (vii) the molecular weight of the second telechelic polymer is not more than about 50 kDa; and (viii) the second reactive functional group comprises a second photopolymerizable moiety.

In some embodiments, provided herein is a photo-curable resin wherein 2, 3, 4, 5, 6, 7, or all of the conditions for the first and/or second telechelic polymers are met.

In some instances, the first photopolymerizable moiety of a first telechelic polymer and the second photopolymerizable moiety of a second telechelic polymer are selected from an acrylate and a methacrylate. In some cases, the first photopolymerizable moiety and the second photopolymerizable moiety are different. In other cases, the first photopolymerizable moiety and the second photopolymerizable moiety are identical.

In some instances, the first telechelic polymer consists of a single monomer species A, and hence the terminal monomers of such telechelic polymer are identical to all other monomers present in the polymer. In other embodiments, the first telechelic polymer is a telechelic block copolymer that comprises at least 2 blocks of different monomer species, wherein one of such 2 different monomers is identical to the first terminal monomer. Depending on the block configuration of the telechelic block copolymer, both terminal monomers can either be identical or different. For example, a first telechelic block copolymer consists of a block configuration of $A_xB_y$, wherein x and y are independently positive integers of 1-50, such first telechelic polymer comprises two terminal monomers A and B that are different. In another example, a first telechelic block copolymer consists of a block configuration of $A_xB_yA_z$, and wherein x, y, and z are independently positive integers of 1-50, such telechelic polymer comprises two identical terminal monomers A. In some embodiments, the second telechelic polymer present in a photo-curable can consists of a single monomer species B, and hence the terminal monomers (including the second monomer) of such telechelic polymer are identical to all other monomers present in the polymer. In other embodiments, the second telechelic polymer is a telechelic block copolymer that comprises at least 2 blocks of different monomer species, wherein one of such 2 different monomers is identical to the second monomer. Depending on the block configuration of the telechelic block copolymer, both terminal monomers can either be identical or different. For example, a second telechelic block copolymer consists of a block configuration of $A_xB_y$, wherein x and y are independently positive integers of 1-50, such second telechelic polymer comprises two terminal monomers A and B that are different. In another example, a second telechelic block copolymer consists of a block configuration of $A_xB_yA_z$, and wherein x, y, and z are independently positive integers of 1-50, such second telechelic polymer comprises two identical terminal monomers A. However, 2 chemically different terminal monomers A and B can still have the same photopolymerizable moiety. Such photopolymerizable moiety can be an acrylate or a methacrylate.

In some instances, the terminal monomers of a telechelic polymer herein can be further modified following synthesis of the polymer as described herein, e.g., to introduce a specific photopolymerizable moiety. For example, a telechelic polymer can comprise terminal functional groups (e.g., hydroxy groups, amines, etc.) that can be used to couple a photopolymerizable moiety to the terminal monomers of the polymer. Any coupling chemistry can be utilized to conduct such terminal modification, including nucleophilic substitution reactions and click chemistry. Following such modifications, the terminal monomers are chemically different to the inner monomers of the telechelic polymer. EXAMPLE 3 herein shows such terminal modification to introduce photoreactive moieties at the termini of a telechelic polymer.

In some aspects, a photo-curable resin provided herein comprises 0.5-99.5 wt % of a telechelic polymer, 1-99 wt % of a telechelic polymer, 10-95 wt % of a telechelic polymer, 20-90 wt % of a telechelic polymer, 25-60 wt % of a telechelic polymer, or 35-50 wt % of a telechelic polymer. In some aspects, the photo-curable resin comprises 25-60 wt % of a telechelic polymer. In some aspects, the photo-curable resin comprises 99.5 wt % or less of a telechelic polymer.

A photo-curable resin described herein can further comprise one or more photoinitiators. Such photoinitiator, when activated with light of an appropriate wavelength (e.g., UV/VIS) can initiate a polymerization reaction (e.g., during photo-curing) between the telechelic polymers, monomers, and other potentially polymerizable components that may be present in the photo-curable resin, to form a polymeric material as further described herein. Generally, photoinitiators described in the present disclosure can include those that can be activated with light and initiate polymerization of the polymerizable components of the formulation. A "photoinitiator", as used herein, may generally refer to a compound that can produce radical species and/or promote radical reactions upon exposure to radiation (e.g., UV or visible light).

In some embodiments, a photo-curable composition further comprises 0.05 to 1 wt %, 0.05 to 2 wt %, 0.05 to 3 wt %, 0.05 to 4 wt %, 0.05 to 5 wt %, 0.1 to 1 wt %, 0.1 to 2 wt %, 0.1 to 3 wt %, 0.1 to 4 wt %, 0.1 to 5 wt %, 0.1 to 6 wt %, 0.1 to 7 wt %, 0.1 to 8 wt %, 0.1 to 9 wt %, or 0.1 to 10 wt %, based on the total weight of the composition, of a photoinitiator. In some embodiments, the photoinitiator is a free radical photoinitiator. In certain embodiments, the free radical photoinitiator comprises an alpha hydroxy ketone moiety (e.g., 2-hydroxy-2-methylpropiophenone or 1-hydroxycyclohexyl phenyl ketone), an alpha-amino ketone (e.g., 2-benzyl-2-(dimethylamino)-4'-morpholinobutyrophenone or 2-methyl-1-[4-(methylthio)phenyl]-2-morpholinopropan-1-one), 4-methyl benzophenone, an azo compound (e.g., 4,4'-Azobis(4-cyanovaleric acid), 1,1'-Azobis(cyclohexanecarbonitrile, Azobisisobutyronitrile, 2,2'-Azobis(2-methylpropionitrile), or 2,2'-Azobis(2-methylpropionitrile)), an inorganic peroxide, an organic peroxide, or any combination thereof. In some embodiments, the composition comprises a photoinitiator comprising SpeedCure TPO-L (ethyl(2,4,6-trimethylbenzoyl)phenyl phosphinate). In some embodiments, a photo-curable composition comprises a photoinitiator selected from a benzophenone, a mixture of benzophenone and a tertiary amine containing a carbonyl group which is directly bonded to at least one aromatic ring, and an Irgacure (e.g., Irgacure 907 (2-methyl-1-[4-(methylthio)phenyl]-2-morpholino-propanone-1) or Irgacure 651 (2,2-dimethoxy-1,2-diphenylethan-1-one). In some embodiments, the photoinitiator comprises an acetophenone photoinitiator (e.g., 4'-hydroxyacetophenone, 4'0phenoxyacetophenone, 4'-ethoxyaceto-phenone), a benzoin, a benzoin derivative, a benzil, a benzil derivative, a benzophenone (e.g., 4-benzoylbiphenyl, 3,4-(dimethylamino)benzophenone, 2-methylbenzophenone), a cationic photoinitiator (e.g., diphenyliodonium nitrate, (4-iodophenyl)diphenylsulfonium triflate, triphenylsulfonium triflate), an anthraquinone, a quinone (e.g., camphorquinone), a phosphine oxide, a phosphinate, 9,10-phenanthrenequinone, a thioxanthone, any combination thereof, or any derivative thereof.

In some embodiments, the photoinitiator can have a maximum wavelength absorbance between 200 and 300 nm, between 300 and 400 nm, between 400 and 500 nm, between 500 and 600 nm, between 600 and 700 nm, between 700 and 800 nm, between 800 and 900 nm, between 150 and 200 nm, between 200 and 250 nm, between 250 and 300 nm, between 300 and 350 nm, between 350 and 400 nm, between 400 and 450 nm, between 450 and 500 nm, between 500 and 550 nm, between 550 and 600 nm, between 600 and 650 nm, between 650 and 700 nm, or between 700 and 750 nm. In some embodiments, the photoinitiator has a maximum wavelength absorbance between 300 to 500 nm.

A photocurable resin described herein can further comprise one or more reactive diluents. As used herein, the term "reactive diluent" generally refers to a substance which reduces the viscosity of another substance. In various cases, a reactive diluent herein is a monomeric species, e.g., a compound according to Formulas (I) or (II) herein. A reactive diluent may become part of another substance, such as a polymer, through, e.g., a polymerization (e.g., photopolymerization) reaction. In some embodiments, a reactive diluent is a curable monomer which, when mixed with a curable resin, reduces the viscosity of the resultant formulation and is incorporated into the polymer that results from polymerization of the formulation. In some instances, a monomer of a telechelic polymer herein can be a reactive diluent. In such instances, the monomer comprising reactive diluent properties can be coupled to a terminus of a telechelic polymer chain such that the monomer becomes a terminal monomer. In some instances, the coupling of such monomer to a telechelic polymer can occur prior to curing, e.g., photo-polymerization, such that the telechelic polymer comprising such terminal monomer is a photo-polymerizable component of a curable resin. In other instances, a monomer comprising reactive diluent properties can be coupled to a terminus of a telechelic polymer chain during curing, e.g., photo-polymerization, such that the monomer comprising reactive diluent properties is incorporated into a forming polymeric structure during a curing process.

In various aspects, the present disclosure provides a curable resin comprising a telechelic polymer and a reactive diluent, wherein the reactive diluent comprises a reactive functional group, and wherein one, two, three or all of the following conditions are met: (i) the reactive diluent has a vapor pressure of at most about 8000 Pa at 60° C. in its monomeric state; (ii) following 2 h heating at 90° C., the reactive diluent has a mass loss rate of less than 0.25% per hour at 90° C. in its monomeric state; (iii) the molecular weight of the telechelic polymer is not more than about 50 kDa; and (iv) the reactive functional group comprises a photopolymerizable moiety. In some cases, two of (i), (ii), (iii), and (iv) are met. In some cases, three of (i), (ii), (iii), and (iv) are met. In some cases, all four of (i), (ii), (iii), and (iv) are met A reactive diluent provided herein can reduce the viscosity of a photo-curable composition, e.g., to a viscosity less than the viscosity of the composition in the absence of the reactive diluent. The reactive diluent(s) may reduce the viscosity of the photo-curable composition by at least 10%, such as by at least 20%, at least 30%, at least 40%, at least 50%, at least 60%, at least 70%, at least 80%, or at least 90%. The curable composition can comprise 5 to 80 wt %, 5 to 70 wt %, 5 to 60 wt %, 5 to 50 wt %, 5 to 40 wt %, 5 to 30 wt %, 5 to 25 wt %, 5 to 20 wt %, 10 to 70 wt %, 10 to 60 wt %, 10 to 50 wt %, 10 to 40 wt %, 10 to 30 wt %, 10 to 25 wt %, 20 to 70 wt %, 20 to 60 wt %, 20 to 50 wt %, 20 to 40 wt %, 20 to 35 wt %, or 20 to 30 wt %, based on the total weight of the composition, of the reactive diluent. In certain embodiments, the curable composition may comprise 5 to 80 wt %, based on the total weight of the composition, of the reactive diluent. In certain embodiments, the curable composition may comprise 5 to 50 wt %, based on the total weight of the composition, of the reactive diluent. The reactive diluent of the curable composition may be monofunctional. In some embodiments, the reactive diluent comprises a methacrylate moiety. In some embodiments, the reactive diluent comprises a dimethacrylate moiety. In some cases, the reactive diluent may be selected from the group consisting of dimethacrylates of polyglycols, hydroxybenzoic acid ester (meth)acrylates, and mixtures thereof. Optionally, the reactive diluent is a cycloalkyl 2-, 3- or 4-((meth)acryloxy)-benzoate.

In some embodiments, a photo-curable resin of the present disclosure can comprise a crosslinking modifier, a light blocker, a solvent, a glass transition temperature modifier, or a combination thereof. In some aspects, the photo-curable resin comprises 0-25 wt % of the crosslinking modifier, the crosslinking modifier having a number-average molecular weight equal to or less than 1,500 Da. In some aspects, the photo-curable resin comprises from 0 to 10 wt %, from 0 to 9 wt %, from 0 to 8 wt %, from 0 to 7 wt %, from 0 to 6 wt %, from 0 to 5 wt %, from 0 to 4 wt %, from 0 to 3 wt %, from 0 to 2 wt %, from 0 to 1 wt %, or from 0 to 0.5 wt % of the light blocker. In some embodiments, the photo-curable resin comprises a solvent. In some embodiments, the solvent comprises a nonpolar solvent. In certain embodiments, the nonpolar solvent comprises pentane, cyclopentane, hexane, cyclohexane, benzene, toluene, 1,4-dioxane, chloroform, diethyl ether, dichloromethane, a derivative thereof, or a combination thereof. In some embodiments, the solvent comprises a polar aprotic solvent. In certain embodiments, the polar aprotic solvent comprises tetrahydrofuran, ethyl acetate, acetone, dimethylformamide, acetonitrile, DMSO, propylene carbonate, a derivative thereof, or a combination thereof. In some embodiments, the solvent comprises a polar protic solvent. In certain embodiments, the polar protic solvent comprises formic acid, n-butanol, isopropyl alcohol, n-propanol, t-butanol, ethanol, methanol, acetic acid, water, a derivative thereof, or a combination thereof. In preferred embodiments, the photo-curable resin comprises less than 90% of the solvent by weight.

In some embodiments, the added component (e.g., a crosslinking modifier, a polymerization catalyst, a polymerization inhibitor, a glass transition temperature modifier, a light blocker, a plasticizer, a solvent, a surface energy modifier, a pigment, a dye, a filler, or a biologically significant chemical) is functionalized so that it can be incorporated into the polymeric material so that it cannot readily be extracted from the final cured material. In certain embodiments, the polymerization catalyst, polymerization inhibitor, light blocker, plasticizer, surface energy modifier, pigment, dye, and/or filler, are functionalized to facilitate their incorporation into the cured polymeric material.

In some embodiments, the glass transition temperature modifier (also referred to herein as a $T_g$ modifier, a glass transition modifier, a crosslinker, and a cross-linker) can be present in a photo-curable composition from about 0 to 50 wt %, based on the total weight of the composition. The $T_g$ modifier can have a high glass transition temperature, which leads to a high heat deflection temperature, which can be necessary to use a material at elevated temperatures. In some embodiments, the curable composition comprises 0 to 80 wt %, 0 to 75 wt %, 0 to 70 wt %, 0 to 65 wt %, 0 to 60 wt %, 0 to 55 wt %, 0 to 50 wt %, 1 to 50 wt %, 2 to 50 wt %, 3 to 50 wt %, 4 to 50 wt %, 5 to 50 wt %, 10 to 50 wt %, 15 to 50 wt %, 20 to 50 wt %, 25 to 50 wt %, 30 to 50 wt %, 35 to 50 wt %, 0 to 40 wt %, 1 to 40 wt %, 2 to 40 wt %, 3 to 40 wt %, 4 to 40 wt %, 5 to 40 wt %, 10 to 40 wt %, 15 to 40 wt %, or 20 to 40 wt % of a $T_g$ modifier. In certain embodiments, the curable composition comprises 0-50 wt % of a glass transition modifier. The $T_g$ modifier typically has a higher $T_g$ than a toughness modifier or a telechelic polymer. Optionally, the number average molecular weight of the $T_g$ modifier is 0.4 to 5 kDa. In some embodiments, the number average molecular weight of the $T_g$ modifier is from 0.1 to 5 kDa, from 0.2 to 5 kDa, from 0.3 to 5 kDa, from 0.4 to 5 kDa, from 0.5 to 5 kDa, from 0.6 to 5 kDa, from 0.7 to 5 kDa, from 0.8 to 5 kDa, from 0.9 to 5 kDa, from 1.0 to 5 kDa, from 0.1 to 4 kDa, from 0.2 to 4 kDa, from 0.3 to 4 kDa, from 0.4 to 4 kDa, from 0.5 to 4 kDa, from 0.6 to 4 kDa, from 0.7 to 4 kDa, from 0.8 to 4 kDa, from 0.9 to 4 kDa, from 1 to 4 kDa, from 0.1 to 3 kDa, from 0.2 to 3 kDa, from 0.3 to 3 kDa, from 0.4 to 3 kDa, from 0.5 to 3 kDa, from 0.6 to 3 kDa, from 0.7 to 3 kDa, from 0.8 to 3 kDa, from 0.9 to 3 kDa, or from 1 to 3 kDa. The toughness modifier, the reactive diluent and the $T_g$ modifier are typically miscible and compatible in the methods described herein. When used in the subject compositions, the $T_g$ modifier may provide for high $T_g$ and strength values, sometimes at the expense of elongation at break. The toughness modifier may provide for high elongation at break and toughness via strengthening effects, and the reactive diluent may improve the processability of the formulations, particularly of those comprising high amounts of toughness modifiers, while maintaining high values for strength and $T_g$.

The photo-curable resin can comprise a filler material which does not participate in polymerization, but which, upon curing, becomes fixed within the cured resin, affecting its material properties. For example, addition of a filler material to a photo-curable resin can decrease vapor pressure and increase viscosity prior to curing and enhance the strength, storage modulus, and stiffness of polymeric materials printed therefrom. Furthermore, in some cases, filler material can inhibit crack or deformation propagation, shielding small breaks from spreading throughout a printed material. For practical applications such as dental appliances, filler material can lower overall mass and thickness requirements and increase lifespan. Such enhancements can be particularly important for orthodontic appliances, such as tooth attachments, which may require continuous or repeated use over extended timeframes. For example, a tooth alignment program may rely on a single set of tooth attachments retaining shape, strength, and integrity over multiple years of treatment.

The filler material can be heterogeneously distributed throughout the photo-curable resin or a material printed therefrom. In some cases, the filler material is homogeneously dispersed throughout the photo-curable resin. Such homogeneous dispersal can be achieved, for example, by agitation or mixing of the curable photo-curable resin prior to or during curing. In some cases, the filler material is homogeneously distributed along a first dimension or set of dimensions, and unevenly distributed along a second dimension or set of dimensions. For example, the filler material can be randomly dispersed throughout a length and width of a photo-curable resin, and unevenly distributed along a height of the photo-curable resin. The filler material can be patterned, for example along a transverse or longitudinal wave, or along a concentration gradient. The filler material can also be concentrated within an interior space or along a surface of the photo-curable resin or material printed therefrom. In some cases, the filler material is patterned within the photo-curable resin. In such cases, the filler material may be concentrated along a longitudinal or transverse wave, a complex pattern, a gradient, or a combination thereof. In some cases, the filler material can be provided as a weave (e.g., overlapping, non-parallel fibers), clusters, sheets, or combinations thereof.

The photo-curable resin can comprise filler material over a range of weight percentages. A filler material can be a minor constituent of a photo-curable resin, for example accounting for less than 5 weight percent (wt %), or can account for a majority of the weight of the photo-curable resin. In some cases, the filler material is present between 0.05 and 60 wt %, between 1 and 5 wt %, between 1 and 10 wt %, between 1 and 20 wt %, between 2 and 5 wt %, between 2 and 10 wt %, between 2 and 20 wt %, between 3 and 6 wt %, between 3 and 10 wt %, between 3 and 20 wt %, between 5 and 10 wt %, between 5 and 25 wt %, between 8 and 20 wt %, between 10 and 60 wt %, between 12 and 25 wt %, between 15 and 30 wt %, between 15 and 40 wt %, between 20 and 35 wt %, between 25 and 50 wt %, between 30 and 50 wt %, between 35 and 65 wt %, between 40 and 65 wt %, between 40 and 80 wt %, between 50 and 75 wt %, or between 60 and 80 wt % of the photo-curable resin.

In some cases, the photo-curable resin comprises a wetting agent. As wetting agents can modify printed material surface properties, inclusion of a wetting agent can enhance suitability for 3D printing. In some cases, a wetting agent can affect resin surface properties to improve its printability. The wetting agent can comprise a hydrophilic material, such as a siloxane, a polyamide, a polylactone, a phosphate ester, a polylactam, or a combination thereof. In particular cases, the wetting agent comprises a siloxane. In some cases, the siloxane is a polyether-modified polydimethylsiloxane.

In some cases, the photo-curable resin comprises from between about 0.01 to about 3 wt % of the wetting agent. In some cases, the photo-curable resin comprises from about 0.05 to about 1.5 wt %, from about 0.1 to about 1.5 wt %, from about 0.3 to about 1.5 wt %, from about 0.1 to about 1 wt %, from about 0.1 to about 0.5 wt %, from about 0.2 to about 1 wt %, from about 0.3 to about 0.7 wt %, or from about 0.4 to about 1 wt % of the wetting agent.

Resin Properties

A photo-curable resin herein can be characterized by having one or more properties.

A photo-curable resin of the present disclosure can have a viscosity from 30 cP to 50,000 cP at a printing temperature. In some instances, the printing temperature is from about 20° C. to about 150° C. In some embodiments, the photo-curable resins have a low viscosity at ambient temperatures. In some embodiments, the photo-curable resin has a viscosity less than or equal to 30,000 cP, less than or equal to 25,000 cP, less than or equal to 20,000 cP, less than or equal to 19,000 cP, less than or equal to 18,000 cP, less than or equal to 17,000 cP, less than or equal to 16,000 cP, less than or equal to 15,000 cP, less than or equal to 14,000 cP, less than or equal to 13,000 cP, less than or equal to 12,000 cP, less than or equal to 11,000 cP, less than or equal to 10,000 cP, less than or equal to 9,000 cP, less than or equal to 8,000 cP, less than or equal to 7,000 cP, less than or equal to 6,000 cP, or less than or equal to 5,000 cP at 25° C. In preferred embodiments, the resin has a viscosity less than 15,000 cP at 25° C.

In some embodiments, the photo-curable resin has a viscosity less than or equal to 100,000 cP, less than or equal to 90,000 cP, less than or equal to 80,000 cP, less than or equal to 70,000 cP, less than or equal to 60,000 cP, less than or equal to 50,000 cP, less than or equal to 40,000 cP, less than or equal to 35,000 cP, less than or equal to 30,000 cP, less than or equal to 25,000 cP, less than or equal to 20,000 cP, less than or equal to 15,000 cP, less than or equal to 10,000 cP, less than or equal to 5,000 cP, less than or equal to 4,000 cP, less than or equal to 3,000 cP, less than or equal to 2,000 cP, less than or equal to 1,000 cP, less than or equal to 750 cP, less than or equal to 500 cP, less than or equal to 250 cP, less than or equal to 100 cP, less than or equal to 90 cP, less than or equal to 80 cP, less than or equal to 70 cP, less than or equal to 60 cP, less than or equal to 50 cP, less than or equal to 40 cP, less than or equal to 30 cP, less than or equal to 20 cP, or less than or equal to 10 cP at a printing temperature. In some embodiments, the photo-curable resin has a viscosity from 50,000 cP to 30 cP, from 40,000 cP to 30 cP, from 30,000 cP to 30 cP, from 20,000 cP to 30 cP, from 10,000 cP to 30 cP, or from 5,000 cP to 30 cP at a printing temperature. In some embodiments, the printing temperature is from 0° C. to 25° C., from 25° C. to 40° C., from 40° C. to 100° C., or from 20° C. to 150° C. In preferred embodiments, the photo-curable resin has a viscosity from 30 cP to 50,000 cP at a printing temperature, wherein the printing temperature is from 20° C. to 150° C.

In preferred embodiments, the photo-curable resin has a viscosity less than 20,000 cP at a print temperature. In some embodiments, the print temperature is from 10° C. to 200° C., from 15° C. to 175° C., from 20° C. to 150° C., from 25° C. to 125° C., or from 30° C. to 100° C. In preferred embodiments, the print temperature is from 20° C. to 150° C.

In certain embodiments, the photo-curable resin has a viscosity less than 1,000 cP at 110° C. In some embodiments, the photo-curable resin has a viscosity less than 1,000 cP at 90° C. In some embodiments, the photo-curable resin has a viscosity less than 500 cP at 70° C. In some embodiments, the photo-curable resin has a viscosity less than 200 cP at 90° C. In some embodiments, the photo-curable resin has a viscosity less than 10,000 cP at 25° C.

A photo-curable resin of the present disclosure can comprise less than 20 wt % hydrogen bonding units. In some aspects, the photo-curable resin comprises less than 15 wt %, less than 10 wt %, less than 9 wt %, less than 8 wt %, less than 7 wt %, less than 6 wt %, less than 5 wt %, less than 4 wt %, less than 3 wt %, less than 2 wt %, or less than 1 wt % hydrogen bonding units, wherein wt % is the weight percent of species, including monomeric units in polymerized, oligomerized, and monomeric form, capable of forming at least one hydrogen bond.

In some embodiments, the photo-curable composition has a melting temperature greater than room temperature. In some embodiments, the photo-curable composition has a melting temperature greater than 20° C., greater than 25° C., greater than 30° C., greater than 35° C., greater than 40° C., greater than 45° C. greater than 50° C., greater than 55° C., greater than 60° C., greater than 65° C., greater than 70° C., greater than 75° C., or greater than 80° C. In some embodiments, the photo-curable composition has a melting temperature from 20° C. to 250° C., from 30° C. to 180° C., from 40° C. to 160° C., or from 50° C. to 140° C. In some embodiments, the photo-curable composition has a melting temperature greater than 60° C. In other embodiments, the photo-curable composition has a melting temperature from 80° C. to 110° C. In some instances, a photo-curable composition can have a melting temperature of about 80° C. before polymerization, and after polymerization, the resulting polymeric material can have a melting temperature of about 100° C.

In certain instances, it may be favorable that a photo-curable composition (e.g., resin), or the polymeric material that such composition can form upon exposure to electromagnetic radiation of appropriate wavelength, is in a liquid phase at an elevated temperature. As an example, a conventional photo-curable resin can comprise polymers and/or polymer crystals that may be viscous, and thus can be difficult to use in the fabrication of objects (e.g., using 3D printing). As a solution for that technical problem, the present disclosure provides photo-curable resins comprising polymers and/or polymer crystals that can melt at an elevated temperature, e.g., at a temperature of fabrication (e.g., during 3D printing), and can have a decreased viscosity at the elevated temperature, which can make such resin more applicable and usable for uses such as 3D printing. Hence, in some embodiments, provided herein are photo-curable resins that are a liquid at an elevated temperature. In some embodiments, the elevated temperature is at or above the melting temperature ($T_m$) of the photo-curable resins. In certain embodiments, the elevated temperature is a temperature in the range from 40° C. to 100° C., from 60° C. to 100° C., from 80° C. to 100° C., from 40° C. to 150° C., or from 150° C. to 350° C. In some embodiments, the elevated temperature is a temperature above 40° C., above 60° C., above 80° C., or above 100° C. In some embodiments, a photo-curable resin herein is a liquid at an elevated temperature with a viscosity less than 50 PaS, less than 20 PaS, less than 10 PaS, less than 5 PaS, or less than 1 PaS. In some embodiments, a photo-curable resin herein is a liquid at an elevated temperature with a viscosity less than 20 PaS. In yet other embodiments, a photo-curable resin herein is a liquid at an elevated temperature with a viscosity less than 1 PaS.

In some embodiments, at least a portion of a photo-curable resin herein has a melting temperature below 100° C., below 90° C., below 80° C., below 70° C., or below 60° C. In some embodiments, at least a portion of a photo-curable resin herein melts at an elevated temperature between 100° C. and 20° C., between 90° C. and 20° C., between 80° C. and 20° C., between 70° C. and 20° C., between 60° C. and 20° C., between 60° C. and 10° C., or between 60° C. and 0° C. In some embodiments, a photo-curable resin herein is a liquid at an elevated temperature with a viscosity less than 50 PaS, less than 20 PaS, less than 10 PaS, less than 5 PaS, or less than 1 PaS.

In some embodiments, a photo-curable resin of the present disclosure can comprise a plurality of crystallizable polymeric materials, at least some of which melt at different temperatures. Such crystallizable polymeric materials can comprise a block copolymer as described herein. In certain embodiments, at least one of the crystallizable polymeric materials melts at a temperature below 100° C., below 90° C., below 80° C., below 70° C., or below 60° C. In some embodiments, at least one of the crystallizable polymeric materials melts at an elevated temperature between 100° C. and 20° C., between 90° C. and 20° C., between 80° C. and 20° C., between 70° C. and 20° C., between 60° C. and 20° C., between 60° C. and 10° C., or between 60° C. and 0° C. In some embodiments, a crystalline domain of a photo-curable resin can melt at a temperature greater than 60° C., greater than 80° C., greater than 100° C., greater than 120° C., or greater than 140° C. In some embodiments, a crystallizable polymeric material of a photo-curable resin herein can be a liquid at an elevated temperature and can have a viscosity of less than 50 PaS, less than 20 PaS, less than 10 PaS, less than 5 PaS, or less than 1 PaS. In certain embodiments, a crystallizable polymeric material of a photo-curable resin herein can be liquid in character as a whole, but can comprise at least one unmelted polymer crystal or a plurality of unmelted polymer crystals (e.g., in some instances, a crystallizable polymeric material can comprise a domain that melts above the melting temperature, and can also comprise a domain that remains crystalline at the same temperature). In some embodiments, the unmelted polymer crystals can have a melting temperature greater than 60° C., greater than 70° C., greater than 80° C., greater than 90° C., greater than 100° C., or greater than 110° C. In some embodiments, the at least one crystallizable polymeric material of a photo-curable resin melts at a temperature greater than the use temperature. As a non-limiting example, a material having a use temperature of about 37° C. can comprise at least one crystallizable polymeric material that is crystalline at 37° C., and melts when warmed to a temperature greater than 37° C. (e.g., 60° C.). As used herein, the use temperature can be a temperature less than or equal to 20° C., from 20° C. to 40° C., or greater than or equal to 40° C. In preferred embodiments, the use temperature comprises a temperature from 20° C. to 40° C. In other preferred embodiments, the use temperature is between 50° C. and 100° C. In still other embodiments, the use temperature is between 100° C. and 150° C. In still other embodiments, the use temperature is above 150° C. In some embodiments, the resin has a melt temperature wherein at least a portion of the resin melts, and the melt temperature is less than 100° C., less than 90° C., less than 80° C., less than 70° C., less than 60° C., less than 50° C., or less than 40° C. In some embodiments, the resin has a melt temperature greater than 60° C., greater than 80° C., greater than 100° C., greater than 120° C., or greater than 140° C.

In certain embodiments, a photo-curable resin herein can comprise, at an elevated temperature, at least 50%, at least 60%, at least 70%, at least 80%, at least 90%, at least 95%, or at least 99% of the photo-crystallizable polymeric material in a liquid phase (i.e., has a melting point below said elevated temperature). In some embodiments, a photo-curable resin at 60° C. comprises at least 50%, at least 60%, at least 70%, at least 80%, at least 90%, at least 95%, or at least 99% of the photo-crystallizable polymeric material in a liquid phase. In some embodiments, a photo-curable resin at 70° C. comprises at least 50%, at least 60%, at least 70%, at least 80%, at least 90%, at least 95%, or at least 99% of the crystallizable photo-polymeric material in a liquid phase. In some embodiments, a photo-curable resin at 80° C. comprises at least 50%, at least 60%, at least 70%, at least 80%, at least 90%, at least 95%, or at least 99% of the photo-crystallizable polymeric material in a liquid phase. In some embodiments, the crystallizable resin at 90° C. comprises at least 50%, at least 60%, at least 70%, at least 80%, at least 90%, at least 95%, or at least 99% of the crystallizable polymeric material in a liquid phase. In some embodiments, the crystallizable resin at 100° C. comprises at least 50%, at least 60%, at least 70%, at least 80%, at least 90%, at least 95%, or at least 99% of the crystallizable polymeric material in a liquid phase.

A photo-curable resin of the present disclosure can be capable of being 3D printed at a temperature greater than 25° C. In some cases, the printing temperature is at least about 30° C., 40° C., 50° C., 60° C., 80° C., or 100° C. As described herein, a photo-polymerizable monomer of this disclosure that can be part of the photo-curable resin, can have a low vapor pressure and/or mass loss at the printing temperature, thereby providing improved printing conditions compared to conventional resins used in additive manufacturing. The vapor pressure of the monomer can be a vapor pressure of the pure (e.g., at least 98% pure) photo-polymerizable monomer as measured by a manometer or by gravimetric analysis.

In some embodiments, provided herein are photo-curable compositions comprising a telechelic polymer as described herein having a molecular weight from about 5 kDa to about 25 kDa, a photo-initiator, and wherein the photo-curable resin comprises less than 20 wt % hydrogen bonding units and has a viscosity less than or equal to 15,000 cP at 25° C. In some aspects, the photo-curable resin comprises 15-55 wt % of the telechelic polymer, 10-75 wt % of the reactive diluent, 15-60 wt % of the reactive diluent, 20-50 wt % of the reactive diluent, 25-45 wt % of the reactive diluent, or 30-40 wt % of the reactive diluent. In some aspects, the photo-curable resin comprises 20-50 wt % of the reactive diluent. In some aspects, the crosslinking modifier is a reactive diluent. In some instances, a photo-curable resin comprises 0.5-99.5 wt %, 1-99 wt %, 10-95 wt %, 20-90 wt %, 25-60 wt %, or 35-50 wt % of the telechelic polymer, the second telechelic polymer, the telechelic block copolymer, or a combination thereof.

In some embodiments, a photo-curable resin composition that can be used in a photopolymerization process can comprise: (i) 1 to 70 wt %, based on the total weight of the composition, of a photopolymerizable telechelic polymer, wherein the telechelic polymer is a telechelic block copolymer having a number average molecular weight of greater than 5 kDa but no more than 50 kDa; (ii) 5 to 80 wt %, based on the total weight of the composition, of a reactive diluent, wherein the reactive diluent is a photopolymerizable compound having a molecular weight of 0.1 to 1.0 kDa; and (iii) 0.1 to 5 wt %, based on the total weight of the composition, of a photoinitiator, wherein the resin has a viscosity of 1 to 70 Pas at 110° C.

IV. Polymeric Materials

A photo-curable resin described herein can form, e.g., upon exposure to electromagnetic radiation of appropriate wavelength, a polymeric material. In various cases, the polymeric material that is formed from the photo-curable resin can have various characteristics and properties that can make it particularly useful in the use and manufacturing of medical devices, e.g., orthodontic appliances. A photo-curable resin used to produce a polymeric material herein can comprise one or more telechelic polymers of the present disclosure, e.g., those comprising, in a polymerized form, monomers according to Formulas (I) and (II), as well as telechelic block copolymers, e.g., one according to Formula (III) herein. A polymeric material provided herein can be biocompatible, bioinert, or a combination thereof. Moreover, the characteristics and properties can be modified by changing the amount and/or types of components present in the initial photo-curable composition. In various instances, a polymeric material of the present disclosure can be produced using additive manufacturing.

Phase Separation in Polymeric Materials

Figure 6:
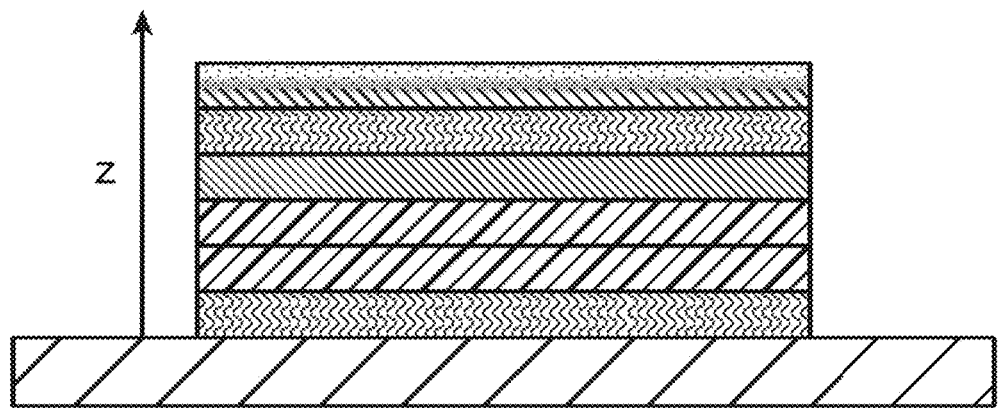
FIG. 6 illustrates the lateral dimensions and vertical dimension as used herein.
Figure 6:
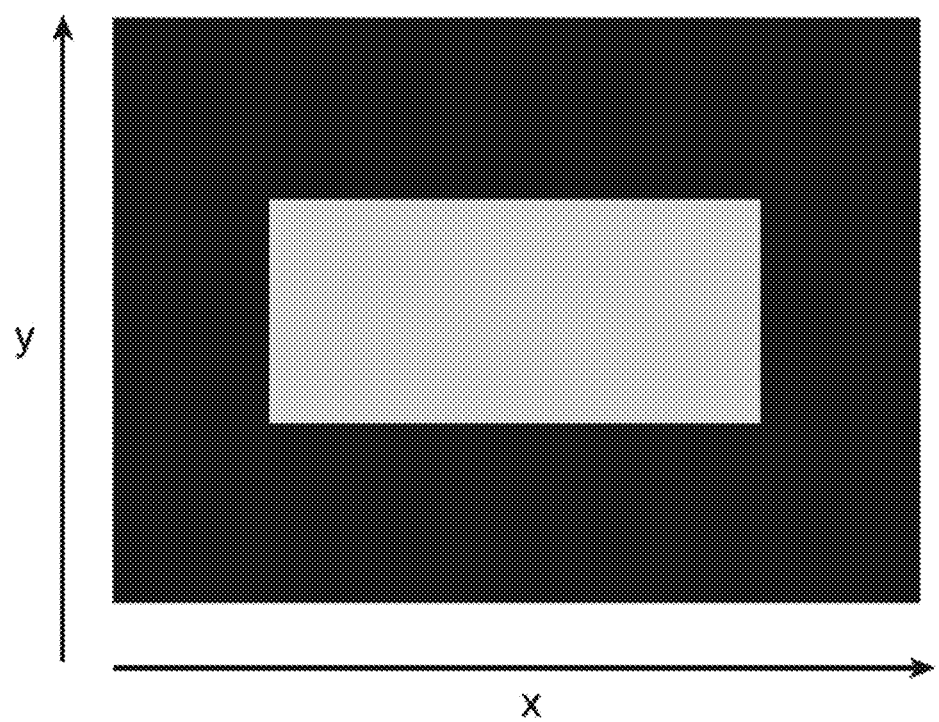

In some aspects herein, a photo-curable composition or resin herein can be cured by exposing such composition or resin to electromagnetic radiation of appropriate wavelength to produce a polymeric material. Such curing or polymerization can induce phase separation in the photo-curable composition and/or in the forming polymeric material. Such polymerization-induced phase separation can occur along one or more lateral and vertical direction(s) (see, e.g., FIG. 6). Polymerization-induced phase separation can generate one or more polymeric phases in the resulting polymeric material. A photo-curable composition undergoing polymerization and polymerization-induced phase separation can comprise one or more telechelic polymers (e.g., telechelic block copolymers) of the present disclosure. Thus, in some cases, at least one polymeric phase of the one or more polymeric phases generated during curing and present in the resulting polymeric material can comprise, in a polymerized form, at least one of the one or more of such telechelic polymers. In an example, a photo-curable resin comprising one telechelic polymer (e.g., telechelic block copolymer) is cured by exposure to electromagnetic radiation of appropriate wavelength. The cured polymeric material comprises 2 polymeric phases A and B. In some cases, at least one of the phases A or B can comprise the telechelic polymer as a component in its polymeric structure. In some cases, both phases A and B can comprise the telechelic polymer as a component in their polymeric structure. The phases A and B can comprise the telechelic polymer in different amounts or concentrations. Thus, in some cases herein, two or more phase that comprise a telechelic polymer herein can be separated by a concentration gradient of such telechelic polymer.

A polymeric phase of a polymeric material of the present disclosure can have a certain size or volume. In some embodiments, a polymeric phase is 3-dimensional, and can have at least one dimension with less than 1000 µm, less than 500 µm, less than 250 µm, less than 200 µm, less than 150 µm, less than 100 µm, less than 90 µm, less than 80 µm, less than 70 µm, less than 60 µm, less than 50 µm, less than 40 µm, less than 30 µm, less than 20 µm, or less than 10 µm. In certain embodiments, the polymeric phase can have at least two dimensions with less than 1000 µm, less than 500 µm, less than 250 µm, less than 200 µm, less than 150 µm, less than 100 µm, less than 90 µm, less than 80 µm, less than 70 µm, less than 60 µm, less than 50 µm, less than 40 µm, less than 30 µm, less than 20 µm, or less than 10 µm. In certain embodiments, the polymeric phase can have three dimensions with less than 1000 µm, less than 500 µm, less than 250 µm, less than 200 µm, less than 150 µm, less than 100 µm, less than 90 µm, less than 80 µm, less than 70 µm, less than 60 µm, less than 50 µm, less than 40 µm, less than 30 µm, less than 20 µm, or less than 10 µm. In some aspects, a polymeric material comprises an average polymeric phase size of less than about 5 µm in at least one spatial dimension.

In various aspects, the present disclosure provides a polymeric material that can comprise one or more polymeric phases, wherein at least one polymeric phase of the one or more polymeric phases is a crystalline phase. In various aspects, the present disclosure provides a polymeric material that can comprise one or more polymeric phases, wherein at least one polymeric phase of the one or more polymeric phases is an amorphous phase. In some instances, provided herein is a polymeric material that can comprise two or more polymeric phases, wherein at least one polymeric phase of the one or more polymeric phases is a crystalline phase, and at least one polymeric phase of the one or more polymeric phases an amorphous phase.

Hence, in some instance, provided herein is a polymeric material comprising: (i) at least one crystalline phase comprising at least one polymer crystal having a melting temperature above 20° C.; and (ii) at least one amorphous phase comprising at least one amorphous polymer having a glass transition temperature greater than 40° C. In some cases, the at least one crystalline phase can comprise, in a polymerized form, one or more telechelic polymers of the present disclosure. In some cases, the at least one amorphous phase can comprise, in a polymerized form, one or more telechelic polymers of the present disclosure. In some aspects, such amorphous phase has a glass transition temperature greater than 50° C., 60° C., 70° C., 80° C., 90° C., 100° C. or greater than 110° C. In some instances, such amorphous phase can comprise, in a polymerized form, one or more telechelic polymers of the present disclosure. In some aspects, the at least one polymer crystal has a melting temperature above 30° C., 40° C., 50° C., 60° C., or above 70° C. In some instances, such crystalline phase can comprise, in a polymerized form, a one or more telechelic polymers of the present disclosure.

Amorphous Polymeric Phases

The present disclosure provides polymeric materials comprising one or more amorphous phases, e.g., generated by polymerization-induced phase separation. Such polymeric materials, or regions of such material that contain polymeric phases, can provide fast response times to external stimuli, which can confer favorable properties to the polymeric material comprising the crystalline phase and/or the amorphous phase, e.g., for using the polymeric material in a medical device (e.g., an orthodontic appliance). In some cases, a polymeric material comprising one or more amorphous polymeric phases can, for example, provide flexibility to the cured polymeric material, which can increase its durability (e.g., the material can be stretched or bent while retaining its structure, while a similar material without amorphous phases can crack). In certain embodiments, amorphous phases can be characterized by randomly oriented polymer chains (e.g., not stacked in parallel or in crystalline structures). In some embodiments, such amorphous polymeric phase of a polymeric material can have a glass transition temperature of greater than about 10° C., 20° C., 30° C., 40° C., 50° C., 60° C., 70° C., 80° C., 90° C., 100° C., or greater than about 110° C. In some embodiments, an amorphous polymeric phase can have a glass transition temperature from about 40° C. to about 60° C., from about 50° C. to about 70° C., from about 60° C. to about 80° C., or from about 80° C. to about 110° C. In some aspects, an amorphous phase has a glass transition temperature less than 10° C., 0° C., –10° C., –20° C., –30° C., –40° C., –50° C., –60° C., or –70° C. In some aspects, one or more amorphous phases will have multiple glass transition temperatures. In some preferred aspects, one or more phases will have a glass transition temperature less than 0° C.

In some embodiments, an amorphous phase herein (also referred to herein as an amorphous domain) can comprise at least about 5%, 10%, 20%, 30%, 40%, 50%, 60%, 70%, 80% or at least about 90% amorphous polymeric material in an amorphous state. The percentage of amorphous polymeric material in an amorphous phase generally refers to total volume percent.

In some embodiments, an amorphous polymeric phase herein can comprise one or more polymer types that may have formed, during curing, from the polymerizable telechelic polymers, telechelic oligomers, polymerizable monomers, and any other polymerizable component that may have been present in the curable composition used to produce the polymeric material that contains such amorphous polymeric phase. In some instances, such one or more polymer types can include one or more of a homopolymer, a linear copolymer, a block copolymer, an alternating copolymer, a periodic copolymer, a statistical copolymer, a random copolymer, a gradient copolymer, a branched copolymer, a brush copolymer, a comb copolymer, a dendrimer, or any combination thereof. In some cases, the amorphous polymeric material comprises a random copolymer. In some embodiments, the amorphous polymeric material can comprise poly-(ethylene) glycol (PEG), poly(ethylene) glycol diacrylate, PEG-THF, polytetrahydrofuran, poly-(tert-butyl acrylate), poly(ethylene-co-maleic anhydride), any derivative thereof, or any combination thereof.

In some instances, polymerizable components of a resin that can form a crystalline material, can form an amorphous phase instead when exposed to conditions that prevent their crystallization. Hence, in some cases, materials that may conventionally be considered crystalline can be used as amorphous material. As a non-limiting example, polycaprolactone can be a crystalline polymer, but when mixed with other polymerizable monomers and telechelic polymers, crystal formation may be prevented and an amorphous phase can form.

An amorphous phase herein can comprise, in a polymerized form, and in addition to one or more telechelic polymers, one or more of the following moieties: an acrylic monomer, an acrylamide, a methacrylamide, an acrylonitrile, a bisphenol acrylic, a carbohydrate, a fluorinated acrylic, a maleimide, an acrylate, 4-acetoxyphenethyl acrylate, acryloyl chloride, 4-acryloylmorpholine, 2-(acryloyloxy)ethyl]-trimethylammonium chloride, 2-(4-benzoyl-3-hydroxyphenoxy)ethyl acrylate, benzyl 2-propylacrylate, butyl acrylate, tert-butyl acrylate, 2[[(butylamino)carbonyl]-oxy]ethyl acrylate, tert-butyl 2-bromoacrylate, 2-carboxyethyl acrylate, 2-chloroethyl acrylate, 2-(diethylamino)-ethyl acrylate, di(ethylene glycol) ethyl ether acrylate, 2-(dimethylamino)ethyl acrylate, 3-(dimethylamino)propyl acrylate, dipentaerythriol penta-/hexa-acrylate, ethyl acrylate, 2-ethylacryloyl chloride, ethyl 2-(bromomethyl)acrylate, ethyl cis-(beta-cyano)acrylate, ethylene glycol dicyclopentenyl ether acrylate, ethylene glycol methyl ether acrylate, ethylene glycol phenyl ether acrylate, ethyl 2-ethylacrylate, 2-ethylexyl acrylate, ethyl 2-propylacrylate, ethyl 2-(trimethylsilylmethyl)acrylate, hexyl acrylate, 4-hydroxybutyl acrylate, 2-hydroxyethyl acrylate, 2-hydroxy-3-phenoxypropyl acrylate, hydroxypropyl acrylate, isobornyl acrylate, isobutyl acrylate, isodecyl acrylate, isooctyl acrylate, lauryl acrylate, methyl 2-acetamidoacrylate, methyl acrylate, a methylene malonate (e.g., dibutyl methylene malonate, dihexyl methylene malonate, or dicyclohexyl methylene malonate), a methylene malonate macromerer (e.g, a polyester of 2-methylenemalonate such as Forza B3000 XP), methyl α-bromoacrylate, methyl 2-(bromomethyl)acrylate, methyl 2-(chloromethyl)-acrylate, methyl 3-hydroxy-2-methylenebutyrate, methyl 2-(trifluoromethyl) acrylate, octadecyl acrylate, pentabromobenzyl acrylate, penta-bromophenyl acrylate, pentafluorophenyl acrylate, poly(ethylene glycol) diacrylate, poly-(ethylene glycol) methyl ether acrylate, poly(propylene glycol) acrylate, epoxidized soybean oil acrylate, 3-sulfopropyl acrylate, tetrahydrofuryl acrylate, 2-tetrahydropyranyl acrylate, 3-(trimethoxysilyl)propyl acrylate, 3,5,5-trimethylhexyl acrylate, 10-undecenyl acrylate, urethane acrylate, urethane acrylate methacrylate, tricylcodecane diacrylate, isobornyl acrylate, a methacrylate, allyl methacrylate, benzyl methacrylate, (2-boc-amino)ethyl methacrylate, tert-butyl methacrylate, 9H-carbazole-9-ethylmethacrylate, 3-chloro-2-hydroxypropyl methacrylate, cyclohexyl methacrylate, 1,10-decamethylene glycol dimethacrylate, ethylene glycol dicyclopentenyl ether methacrylate, ethylene glycol methyl ether methacrylate, 2-ethylhexyl methacrylate, furfuryl methacrylate, glycidyl methacrylate, glycosyloxyethyl methacrylate, hexyl methacrylate, hydroxybutyl methacrylate, 2-hydroxy-5-N-methacrylamidobenzoic acid, isobutyl methacrylate, methacryloyl chloride, methyl methacrylate, mono-2-methacryloyloxy)ethyl succinate, 2-N-morpholinoethyl methacrylate, 1-naphthyl methacrylate, pentabromphenyl methacrylate, phenyl methacrylate, pentabromophenyl methacrylate, TEMPO methacrylate, 3-sulfopropyl methacrylate, triethylene glycol methyl ether methacrylate, 2-[(1',1',1'-trifluoro-2'-(trifluoromethyl)-2'0hydroxy)propyl]-3-norbornyl methacrylate, 3,3,5-trimethylcyclohexyl methacrylate, (trimethylsilyl)methacrylate, vinyl methacrylate, isobornyl methacrylate, bisphenol A dimethacrylate, an Omnilane OC, tert-butyl acrylate, isodecyl acrylate, tricylcodecane diacrylate, a polyfunctional acrylate, N,N'-methylenebisacrylamide, 3-(acryloyloxy)-2-hydroxypropyl) methacrylate, bis[2-(methacryloyloxy)ethyl] phosphate, 1,3-butanediol diacrylate, 1,4-butanediol diacrylate, diurethane dimethacrylate, N,N'-ethylenebis(acrylamide), glycerol 1,3-diglycerolate diacrylate, 1,6-hexanediol diacrylate, hydroxypivalyl hydroxypivalate bis[6-(acryloyloxy)hexanoate], neopentyl glycol diacrylate, pentaerythritol diacrylate, 1,3,6-triacryloyl hexahydro-1,3,5-triazine, trimethylolpropane ethoxylate, tris[2-(acryloyloxy)ethyl] isocyanurate, any derivative thereof, or a combination thereof.

In some embodiments, an amorphous phase of a polymeric material herein can comprise one or more reactive functional groups that can allow for further modification of the polymeric material, such as additional polymerization (e.g., post-curing). In some embodiments, an amorphous polymeric material comprises a plurality of reactive functional groups, and the reactive functional groups can be located at one or both terminal ends of the amorphous material, in-chain, at a pendant (e.g., a side group attached to the polymer backbone), or any combination thereof. Non-limiting examples of reactive functional groups include free radically polymerizable functionalities, photoactive groups, groups facilitating step growth polymerization, thermally reactive groups, and/or groups that facilitate bond formation (e.g., covalent bond formation). In some embodiments, the functional groups comprise an acrylate, a methacrylate, an acrylamide, a vinyl group, a vinyl ether, a thiol, an allyl ether, a norbornene, a vinyl acetate, a maleate, a fumarate, a maleimide, an epoxide, a ring-strained cyclic ether, a ring-strained thioether, a cyclic ester, a cyclic carbonate, a cyclic silane, a cyclic siloxane, a hydroxyl, an amine, an isocyanate, a blocked isocyanate, an acid chloride, an activated ester, a Diels-Alder reactive group, a furan, a cyclopentadiene, an anhydride, a group favorable toward photodimerization (e.g., an anthracene, an acenaphthalene, or a coumarin), a group that photodegrades into a reactive species (e.g., Norrish Type 1 and 2 materials), an azide, a derivative thereof, or a combination thereof.

Crystalline Polymeric Phases

As further described herein, a polymeric material of the present disclosure can comprise one or more crystalline phases, e.g., generated by polymerization-induced phase separation during curing. As described herein, a crystalline phase is a polymeric phase of a cured polymeric material that comprises at least one polymer crystal. As disclosed herein, a crystalline phase may consist of a single polymeric crystal, or may comprise a plurality of polymeric crystals.

In some embodiments, a crystalline polymeric phase can have a melting temperature equal to or greater than about 20° C., 30° C., 40° C., 50° C., 60° C., 70° C., 80° C., 90° C., 100° C., 120° C., or equal to or greater than about 150° C. In some cases, at least two crystalline phases of a plurality of crystalline phases can have a different melting temperature due to, e.g., differences in crystalline phase sizes, impurities, degree of cross-linking, chain lengths, thermal history, rates at which polymerization occurred, degree of phase separation, or any combination thereof. In some aspects, at least two crystalline phases of a polymeric material can each have a polymer crystal melting temperature within about 5° C. of each other. In some instances, such melting temperature difference can be less than about 5° C. In other instances, such melting temperature difference can be greater than about 5° C. In some aspects, each of the polymer crystal melting temperatures of a polymeric material can be from about 40° C. to about 100° C. In some aspects, at least about 80% of the crystalline domains of a polymeric material can comprise a polymer crystal having a melting temperature between about 40° C. and about 100° C.

In some embodiments, at least 80% of the crystalline phases have a crystal melting point at a temperature between 0° C. and 100° C. In some embodiments, at least 80% of the crystalline phases have a crystal melting point at a temperature between 40° C. and 60° C., between 40° C. and 80° C., between 40° C. and 100° C., between 60° C. and 80° C., between 60° C. and 100° C., between 80° C. and 100° C., or greater than 100° C. In some embodiments, at least 90% of the crystalline phases have a crystal melting point at a temperature between 0° C. and 100° C. In some embodiments, at least 90% of the crystalline phases have a crystal melting point at a temperature between 40° C. and 60° C., between 40° C. and 80° C., between 40° C. and 100° C., between 60° C. and 80° C., between 60° C. and 100° C., between 80° C. and 100° C., or greater than 100° C. In some embodiments, at least 95% of the crystalline phases have a crystal melting point at a temperature between 0° C. and 100° C. In some embodiments, at least 95% of the crystalline phases have a crystal melting point at a temperature between 40° C. and 60° C., between 40° C. and 80° C., between 40° C. and 100° C., between 60° C. and 80° C., between 60° C. and 100° C., between 80° C. and 100° C., or greater than 100° C.

In certain embodiments, the temperature at which a crystalline phase of a cured polymeric material melts can be controlled, e.g., by using different amounts and types of polymerizable components in the curable resin, e.g., different amounts and types of telechelic polymers, e.g., block copolymers with various block configurations and/or different species of monomers comprising certain types of substituents (e.g., bulky groups with molecular radii greater then hydrogen, methyl, etc.), different amounts and types of telechelic polymer(s) and/or oligomer(s), and/or by using blocks of polymers (e.g., in telechelic block copolymers) that have different crystal melting points.

In some embodiments, the curing of a resin can occur at an elevated temperature (e.g., at about 90° C.), and as the cured polymeric material cools to room temperature (e.g., 25° C.), the cooling can trigger the formation and/or growth of polymeric crystals in the polymeric material. In some instances, a polymeric material can be a solid at room temperature and can be crystalline-free, but can form crystalline phase over time. In such cases, a crystalline phase can form within 1 hour, within 2 hours, within 4 hours, within 8 hours, within 12 hours, within 18 hours, within 1 day, within 2 days, within 3 days, within 4 days, within 5 days, within 6 days, or within 7 days after cooling. In some embodiments, a crystalline phase can form while the cured polymeric material is in a cooled environment, e.g., an environment having a temperature from about 40° C. to about 30° C., from about 30° C. to about 20° C., from about 20° C. to about 10° C., from about 10° C. to about 0° C., from about 0° C. to about −10° C., from about −10° C. to about −20° C., from about −20° C. to about −30° C., or below about −30° C. In some instances, a polymeric material can be heated to an elevated temperature in order to induce crystallization or formation of crystalline phases. As a non-limiting example, a polymeric material that is near its glass transition temperature can comprise polymer chains that may not be mobile enough to organize into crystals, and thus further heating the material can increase chain mobility and induce formation of crystals.

In some embodiments, the generation, formation, and/or growth of a polymeric phase is spontaneous. In some embodiments, the generation, formation, and/or growth of a polymer crystal is facilitated by a trigger. In some embodiments, the trigger comprises the addition of a seeding particle (also referred to herein as a "seed"), which can induce crystallization. Such seeds can include, for example, finely ground solid material that has at least some properties similar to the forming crystals. In some embodiments, the trigger comprises a reduction of temperature. In certain embodiments, the reduction of temperature can include cooling the cured material to a temperature from 40° C. to 30° C., from 30° C. to 20° C., from 20° C. to 10° C., from 10° C. to 0° C., from 0° C. to –10° C., from –10° C. to –20° C., from –20° C. to –30° C., or below –30° C. In some embodiments, the trigger can comprise an increase in temperature. In certain embodiments, the increase of temperature can include heating the polymeric cured material to a temperature from 20° C. to 40° C., from 40° C. to 60° C., from 60° C. to 80° C., from 80° C. to 100° C., or above 100° C. In some embodiments, the trigger comprises a force placed on the cured polymeric material. In certain embodiments, the force includes squeezing, compacting, pulling, twisting, or providing any other physical force to the material. In some embodiments, the trigger comprises an electrical charge and/or electrical field applied to the material. In some embodiments, formation of one or more crystalline phases may be induced by more than one trigger (i.e., more than one type of trigger can facilitate the generation, formation, and/or growth of crystals). In some embodiments, the polymeric material comprises a plurality of crystalline phases, and at least two of the crystalline phase may be induced by different triggers.

In some embodiments, a polymeric material herein comprises a crystalline phase that has discontinuous phase transitions (e.g., first-order phase transitions). In some cases, a polymeric material has discontinuous phase transitions, due at least in part to the presence of one or more crystalline domains. As a non-limiting example, a cured polymeric material comprising one or more crystalline domains can, when heated to an elevated temperature, have one or more portions that melt at such elevated temperature, as well as one or more portions that remain solid.

In some embodiments, a cured polymeric material comprises crystalline phases that are continuous and/or discontinuous phases. A continuous phase can be a phase that can be traced or is connected from one side of a polymeric material to another side of the material; for instance, a closed-cell foam has material comprising the foam that can be traced across the sample, whereas the closed cells (bubbles) represent a discontinuous phase of air pockets. In some embodiments, the at least one crystalline phase forms a continuous phase while the at least one amorphous phase is discontinuous across the material. In another embodiment, the at least one crystalline phase is discontinuous and the at least one amorphous phase is continuous across the material. In another embodiment, both the at least one crystalline and the at least one amorphous phases are continuous across the material. In some embodiments, a polymeric material comprises a plurality of crystalline phases, wherein one or more crystalline phases of the plurality of crystalline phases have a high melting point (e.g., at least about 50° C., 70° C., or 90° C.) and are in a discontinuous phase, while another one or more crystalline phases of the plurality of crystalline phases have a low melting point (e.g., at less than about 50° C., 70° C., or 90° C.) and are in a continuous phase.

In some aspects, a polymeric material comprises an average crystalline phase size of less than about 100 μm, 50 μm, 20 μm, 10 μm, or less then about 5 μm in at least one spatial dimension.

In some aspects, a polymer crystal of a crystalline phase can comprise greater than about 40 wt %, greater than about 50 wt %, greater than about 60 wt %, greater than about 70 wt %, greater than about 80 wt %, or greater than about 90 wt % of linear polymers and/or linear oligomers, wherein such linear polymers and/or linear oligomers can comprise, in a polymerized form, one or more telechelic polymers and/or telechelic oligomers, respectively.

In some aspects, a polymeric material described herein can have a crystalline phase content from about 10% to about 90%, from about 20% to about 80%, from about 30% to about 70%, from about 40% to about 95%, or from about 50% to about 95%, as measured by X-ray diffraction. In some aspects, a polymeric material herein can comprise a weight ratio of crystalline phases to amorphous phases from about 1:99 to about 99:1.

In various aspects, the present disclosure provides a polymeric material—produced from a photo-curable resin—comprising: an amorphous phase; and a crystalline phase comprising a polymer having a tactic property. In some aspects, the tactic property comprises being isotactic, being syndiotactic, having a plurality of meso diads, having a plurality of racemo diads, having a plurality of isotactic triads, having a plurality of syndiotactic triads, or having a plurality of heterotactic triads. In some aspects, the polymeric material comprising the crystalline phase comprising the polymer having the tactic property has increased crystallinity compared to a comparable polymeric material comprising a comparable atactic polymer. In some aspects, greater than 50%, greater than 60%, greater than 70%, greater than 80%, greater than 90%, greater than 95%, or greater than 99% of the crystalline phase comprises the tactic property. In some aspects, greater than 50%, greater than 60%, greater than 70%, greater than 80%, greater than 90%, greater than 95%, or greater than 99% of the polymeric material comprises the tactic property. In some aspects, the polymeric material comprising the polymer having the tactic property is characterized by at least one of: an elongation at break greater than or equal to 5%; a storage modulus greater than or equal to 500 MPa; a tensile modulus greater than or equal to 500 MPa; and a stress remaining greater than or equal to 0.01 MPa. In some aspects, a comparable polymeric material comprising an atactic polymer comparable to the polymer having the tactic property is characterized by at least one of: an elongation at break less than 5%; a storage modulus less than 500 MPa; a tensile modulus less than 500 MPa; and a stress remaining less than 0.01 MPa. In some aspects, the polymeric material is at least partially cross-linked. In some aspects, the polymeric material is a thermoset or a thermoplastic. In some aspects, the polymeric material comprises semi-crystalline segments.

In some embodiments, a cured polymer such as a cross-linked polymer, can be characterized by a tensile stress-strain curve that displays a yield point after which the test specimen continues to elongate, but there is no (detectable) or only a very low increase in stress. Such yield point behavior typically occurs "near" the glass transition temperature, where the material is between the glassy and rubbery regimes and may be characterized as having viscoelastic behavior. In some embodiments, viscoelastic behavior is observed in the temperature range from about 20° C. to about 40° C. The yield stress is determined at the yield point. In some embodiments, the modulus is determined from the initial slope of the stress-strain curve or as the secant modulus at 1% strain (e.g. when there is no linear portion of the stress-strain curve). The elongation at yield is determined from the strain at the yield point. When the yield point occurs at a maximum in the stress, the ultimate tensile strength is less than the yield strength. For a tensile test specimen, the strain is defined by $\ln(l/l_0)$, which may be approximated by $(l-l_0)/l_0$ at small strains (e.g. less than approximately 10%) and the elongation is $l/l_0$, where l is the gauge length after some deformation has occurred and $l_0$ is the initial gauge length. The mechanical properties can depend on the temperature at which they are measured. The test temperature may be below the expected use temperature for a dental appliance such as 35° C. to 40° C. In embodiments, the test temperature is 23±2° C.

As provided further herein, the polymeric material comprising a crystalline phase (can also referred to herein as a crystalline domain) and an amorphous phase (can also referred to herein as an amorphous domain) can have improved characteristics, such as the ability to act quickly (e.g., vibrate quickly and react upon application of strain, from the elastic characteristics of the amorphous domain) and also provide strong modulus (e.g., are stiff and provide strength, from the crystalline domain). The polymer crystals disclosed herein can comprise closely stacked and/or packed polymer chains. In some embodiments, the polymer crystals comprise long oligomer or long polymer chains that are stacked in an organized fashion, overlapping in parallel. The polymer crystals can in some cases be pulled out of a crystalline phase, resulting in an elongation as the polymer chains of the polymer crystal are pulled (e.g., application of a force can pull the long polymer chain of the polymer crystal, thus introducing disorder to the stacked chains, pulling at least a portion out of its crystalline state without breaking the polymer chain). This is in contrast with fillers that are traditionally used in the formation of resins for materials with high flexural modulus, which can simply slip through the amorphous phase as forces are applied to the polymeric material or when the fillers are covalently bonded to the polymers causing a reduction in the elongation to break for the material. The use of polymer crystals in the resulting polymeric material can thus provide a less brittle product that can retain more of the original physical properties following use (i.e., are more durable), and retains elastic characteristics through the combination of amorphous and crystalline phases.

In some embodiments, a polymeric material herein comprises a ratio of crystalline polymeric phases to amorphous polymeric phases (wt/wt) of greater than about 1:10, greater than about 1:9, greater than about 1:8, greater than about 1:7, greater than about 1:6, greater than about 1:5, greater than about 1:4, greater than about 1:3, greater than about 1:2, greater than about 1:1, greater than about 2:1, greater than about 3:1, greater than about 4:1, greater than about 5:1, greater than about 6:1, greater than about 7:1, greater than about 8:1, greater than about 9:1, greater than about 10:1, greater than about 20:1, greater than about 30:1, greater than about 40:1, greater than about 50:1, or greater than about 99:1. In some embodiments, the polymeric material comprises a ratio of the crystallizable polymeric material to the amorphous polymeric material (wt/wt) of at least 1:10, at least 1:9, at least 1:8, at least 1:7, at least 1:6, at least 1:5, at least 1:4, at least 1:3, at least 1:2, at least 1:1, at least 2:1, at least 3:1, at least 4:1, at least 5:1, at least 6:1, at least 7:1, at least 8:1, at least 9:1, at least 10:1, at least 20:1, at least 30:1, at least 40:1, at least 50:1, or at least 99:1. In certain embodiments, the polymeric material comprises a ratio of crystalline polymeric phases to amorphous polymeric phases (wt/wt) of between 1:9 and 99:1, between 1:9 and 9:1, between 1:4 and 4:1, between 1:4 and 1:1, between 3:5 and 1:1, between 1:1 and 5:3, or between 1:1 and 4:1.

In some embodiments, a polymeric material of this disclosure comprises a ratio of crystalline polymeric phases to amorphous polymeric phases (vol/vol) of greater than about 1:10, greater than about 1:9, greater than about 1:8, greater than about 1:7, greater than about 1:6, greater than about 1:5, greater than about 1:4, greater than about 1:3, greater than about 1:2, greater than about 1:1, greater than about 2:1, greater than about 3:1, greater than about 4:1, greater than about 5:1, greater than about 6:1, greater than about 7:1, greater than about 8:1, greater than about 9:1, greater than about 10:1, greater than about 20:1, greater than about 30:1, greater than about 40:1, greater than about 50:1, or greater than about 99:1. In some embodiments, the polymeric material comprises a ratio of crystalline polymeric phases to amorphous polymeric phases (vol/vol) of at least 1:10, at least 1:9, at least 1:8, at least 1:7, at least 1:6, at least 1:5, at least 1:4, at least 1:3, at least 1:2, at least 1:1, at least 2:1, at least 3:1, at least 4:1, at least 5:1, at least 6:1, at least 7:1, at least 8:1, at least 9:1, at least 10:1, at least 20:1, at least 30:1, at least 40:1, at least 50:1, or at least 99:1. In certain embodiments, the polymeric material comprises a ratio of crystalline polymeric phases to amorphous polymeric phases (vol/vol) of between 1:9 and 99:1, between 1:9 and 9:1, between 1:4 and 4:1, between 1:4 and 1:1, between 3:5 and 1:1, between 1:1 and 5:3, or between 1:1 and 4:1.

Properties of Polymeric Materials

A polymeric material of this disclosure formed from the polymerization of a curable resin disclosed herein can provide advantageous characteristics compared to conventional polymeric materials. In some instances, and as described herein, a polymeric material can contain some percentage of crystallinity, which can impart an increased toughness and high modulus to the polymeric material, while in some circumstances being a 3D printable material. Furthermore, a polymeric material herein can further comprise one or more amorphous phases that can provide increased durability, prevention of crack formation, as well as the prevention of crack propagation. In some instances, a polymeric material can also have low amounts of water uptake, and can be solvent resistant. In some cases, a polymeric material can be characterized by one or more of the properties selected from the group consisting of elongation at break, storage modulus, tensile modulus, stress remaining, glass transition temperature, water uptake, hardness, color, transparency, hydrophobicity, lubricity, surface texture, percent crystallinity, phase composition ratio, phase domain size, and phase domain size and morphology. Further, as described herein, the polymeric materials provided herein can be used for a multitude of applications, including 3D printing, to form materials having favorable properties of both elasticity and stiffness.

In some instances, a polymeric material of the present disclosure can have one or more of the following characteristics and properties: (A) a tensile modulus greater than or equal to 200 MPa; (B) a flexural stress and/or flexural modulus of greater than or equal to 1.5 MPa remaining after 24 hours in a wet environment at 37° C.; (C) an elongation at break greater than or equal to 5%; (D) a water uptake of less than 25 wt % when measured after 24 hours in a wet environment at 37° C.; and (E) transmission of at least 30% of visible light through the polymeric material after 24 hours in a wet environment at 37° C. In some instances, 2, 3, 4, or all of these characteristics are present in a polymeric material of the present disclosure.

In some embodiments, the polymeric material is characterized by a water uptake of less than 20 wt %, less than 15 wt %, less than 10 wt %, less than 5 wt %, less than 4 wt %, less than 3 wt %, less than 2 wt %, less than 1 wt %, less than 0.5 wt %, less than 0.25 wt %, or less than 0.1 wt % when measured after 24 hours in a wet environment at 37° C.

In some embodiments, the polymeric material has an ultimate tensile strength from 10 MPa to 100 MPa, from 15 MPa to 80 MPa, from 20 MPa to 60 MPa, from 10 MPa to 50 MPa, from 10 MPa to 45 MPa, from 25 MPa to 40 MPa, from 30 MPa to 45 MPa, or from 30 MPa to 40 MPa after 24 hours in a wet environment at 37° C.

In some embodiments, the polymeric material is characterized by an elongation at break greater than 10%, an elongation at break greater than 20%, an elongation at break greater than 30%, an elongation at break of 5% to 250%, an elongation at break of 20% to 250%, or an elongation at break value between 40% and 250% after 24 hours in a wet environment at 37° C.

In some embodiments, the polymeric material is characterized by a storage modulus of 0.1 MPa to 4000 MPa, a storage modulus of 300 MPa to 3000 MPa, or a storage modulus of 750 MPa to 3000 MPa after 24 hours in a wet environment at 37° C.

In some embodiments, the polymeric material has a flexural stress and/or flexural modulus remaining of 100 MPa or more, 80 MPa or more, 70 MPa or more, 60 MPa or more, or 50 MPa or more after 24 hours in a wet environment at 37° C. In some embodiments, the polymeric material has a flexural stress remaining of 100 MPa or more, 80 MPa or more, 70 MPa or more, 60 MPa or more, or 50 MPa or more after 24 hours in a wet environment at 37° C.

In some embodiments, the polymeric material has greater than 60% conversion of double bonds to single bonds compared to the photo-curable resin, as measured by FTIR. Furthermore, in some instances, at least about 40%, 50%, 60%, or 70% of visible light passes through the polymeric material after storage of the materials for 24 hours in a wet environment at 37° C.

In some instances, a polymeric material can have a low amount of hydrogen bonding which can facilitate a decreased uptake of water in comparison with conventional polymeric materials having greater amounts of hydrogen bonding. Thus, in some instances, a polymeric material herein can comprise less than about 10 wt %, less than about 9 wt %, less than about 8 wt %, less than about 7 wt %, less than about 6 wt %, less than about 5 wt %, less than about 4 wt %, less than about 3 wt %, less than about 2 wt %, less than about 1 wt %, or less than about 0.5 wt % water when fully saturated at use temperature (e.g., about 20° C., 25° C., 30° C., or 35° C.). In some instances, the use temperature can include the temperature of a human mouth (e.g., approximately 35-40° C.). The use temperature can be a temperature selected from −100-250° C., 0-90° C., 0-80° C., 0-70° C., 0-60° C., 0-50° C., 0-40° C., 0-30° C., 0-20° C., 0-10° C., 20-90° C., 20-80° C., 20-70° C., 20-60° C., 20-50° C., 20-40° C., 20-30° C., or below 0° C.

In some embodiments, a polymeric material generated from a photo-curable composition described herein can have a melting temperature greater than room temperature. In some embodiments, the polymeric material has a melting temperature greater than the temperature of a human oral cavity. As a non-limiting example, it can be favorable that each polymer crystals of the plurality of polymer crystals present in a polymeric material can have a melting temperature above the temperature of a human oral cavity, such that the polymer crystals remain solid in such a setting. In some embodiments, the polymeric material has a melting temperature greater than 20° C., greater than 25° C., greater than 30° C., greater than 35° C., greater than 40° C., greater than 45° C., greater than 50° C., greater than 55° C., greater than 60° C., greater than 65° C., greater than 70° C., greater than 75° C., or greater than 80° C. In some embodiments, the polymeric material has a melting temperature from 20° C. to 250° C., from 30° C. to 180° C., from 40° C. to 160° C., or from 50° C. to 140° C. In some embodiments, the polymeric material has a melting temperature greater than 60° C. In some embodiments, the polymeric material has a melting temperature from 80° C. to 110° C.

In various instances herein, a polymeric material of the present disclosure can be biocompatible, bioinert, or a combination thereof. In such instances, no or only very limited amounts of monomeric material that may be present in the photo-curable resin leaches out of the polymeric material formed from such photo-curable resin. This may be of particular importance for use in orthodontic appliances that are used in the intraoral environment.

In various embodiments herein, polymer chains of a polymeric material can form linear sections in which linear chain portions of a plurality of polymer molecules are aligned to form a crystal. In some instances, polymer chains of a polymeric material can form a crystal in which different portions of the same polymer chain are linearly aligned such that a polymer chain folds on itself. As described elsewhere herein In some embodiments, a polymeric material herein comprises at least one crystalline phase and at least one amorphous phase, wherein the at least one crystalline phase, the at least one amorphous phase, or both, contain one or more telechelic polymers of the present disclosure. In some instance, a combination of these two types of phases or domains can create a polymeric material that has a high modulus phase (e.g., the crystalline polymeric material can provide a high modulus) and a low modulus phase (e.g., provided by the presence of the amorphous polymeric material). By having these two phases, the polymeric material can have a high modulus and a high elongation, as well as high stress remaining following stress relaxation.

In various instances, the one or more amorphous phases of the polymeric material can have a glass transition temperature of at least about 30° C., 40° C., 50° C., 60° C., 70° C., 80° C., 90° C., 100° C., or at least about 110° C. In such cases, at least one amorphous phase of the one or more amorphous phases having a glass transition temperature of at least about 50° C. comprises, integrated in its polymeric structure, one or more telechelic polymers of the present disclosure, such as one or more telechelic block copolymers as described herein.

In some cases, a polymeric material can comprise a polymer crystal attached to the amorphous polymer. As non-limiting examples, the polymer crystal can be covalently bonded to, entangled with, cross-linked to, and/or otherwise associated with (e.g., through hydrophobic interactions, pi-stacking, or hydrogen bonding interactions) the amorphous polymeric material.

In some embodiments, a polymeric material herein can comprise crystalline and/or amorphous phases having a smaller size (e.g., less than about 1 μm). Smaller polymeric phases in a polymeric material can facilitate light passage and provide a polymeric material that appears clear. In contrast, larger polymeric phases (e.g., those larger than about 1 μm) can scatter light, for example when the refractive index of the polymer crystal is different from the refractive index of the amorphous phase adjacent to the polymer crystal (e.g., the amorphous material). In some cases, at least 40%, 50%, 60%, or 70% of visible light passes through the polymeric material after 24 hours in a wet environment at 37° C.

Thus, in some cases, it may be advantageous to have a polymeric material that comprises small polymeric phases such as crystalline or amorphous phases, e.g., as measured by the longest length of the phases. In some embodiments, such polymeric material comprises an average polymeric phase size that is less than 5 μm. In some embodiments, such polymeric material comprises an average polymeric phase size that is less than 1 μm. In some cases, the maximum polymeric phase size of the polymeric materials can be about 5 μm. In some embodiments, at least about 50%, at least about 60%, at least about 70%, at least about 80%, at least about 90%, at least about 95%, or at least about 99% of the polymeric phases of the polymeric material have a size of less than about 5 μm. In yet other embodiments, a polymeric material comprises an average polymeric phase size that is less than about 1 μm. In some embodiments, the maximum polymer polymeric phase size of the cured polymeric materials is 1 μm. In some embodiments, at least about 50%, at least about 60%, at least about 70%, at least about 80%, at least about 90%, at least about 95%, or at least about 99% of the polymeric phases of the polymeric material have a size less than about 1 μm. In yet other embodiments, the polymeric material comprises an average polymeric phase size that is less than about 500 nm. In some embodiments, the maximum polymeric phase size of the cured polymeric materials is about 500 nm. In some embodiments, at least about 50%, at least about 60%, at least about 70%, at least about 80%, at least about 90%, at least about 95%, or at least about 99% of the polymeric phases of the polymeric material have a size less than 500 nm.

In some embodiments, the size of at least one or more of the polymeric phases (e.g., crystalline phases and amorphous phases) of a polymeric material can be controlled. Non-limiting examples of ways in which the size of the polymeric phases can be controlled includes: rapidly cooling the cured polymeric material, annealing the cured polymeric material at an elevated temperature (i.e., above room temperature), annealing the cured polymeric material at a temperature below room temperature, controlling the rate of polymerization, controlling the intensity of light during the curing step using light, controlling and/or adjusting polymerization temperature, exposing the cured polymeric material to sonic vibrations, and/or controlling the presence and amounts of impurities, and in particular for crystalline phases, adding crystallization-inducing chemicals or particles (e.g., crystallization seeds).

In some embodiments, the refractive index of the one or more crystalline phases and/or one or more amorphous phases of a polymeric material herein can be controlled. A reduction in difference of refractive index between different phases (e.g., reduction in the difference of refractive index between the crystalline polymer and the amorphous polymer) can increase clarity of the cured polymeric material, providing a clear or nearly clear material. Light scatter can be decreased by minimizing polymer crystal size, as well as by reducing the difference of refractive index across an interface between an amorphous polymeric phase and a crystalline phase. In some embodiments, the difference of refractive index between a given polymeric phase and a neighboring phase (e.g., crystalline and a neighboring amorphous phase) can be less than about 0.1, less than about 0.01, or less than about 0.001.

In some instances, a polymeric material described herein can form a polymeric film. Such polymeric film can have a thickness of at least about 50 μm, 100 μm, 250 μm, 500 μm, 1 mm, 2 mm and not more than 3 mm.

Polymeric Materials in Medical Devices

The present disclosure further provides devices that comprise a polymeric material of the present disclosure. As described herein, such polymeric material can comprise, incorporated in its polymeric structure, one or more telechelic polymers of the present disclosure, such as one or more telechelic block copolymers as described herein. In various cases, the device can be a medical device. The medical device can be an orthodontic appliance. The orthodontic appliance can be a dental aligner, a dental expander or a dental spacer.

V. Methods of Making and Using Telechelic Polymers

The present disclosure provides methods for using the telechelic polymers, photo-curable resins comprising such telechelic polymers, and polymeric materials formed from the photo-curable resins, as well as methods for producing the same. The telechelic polymers of the present disclosure, e.g., those comprising, in a polymerized form, monomers according to Formulas (I) and (II), as well as telechelic block copolymers, e.g., one according to Formula (III) herein, can be used as components in materials used in many different industries such as transportation (e.g., planes, trains, boats, automobiles, etc.), hobbyist, prototyping, medical, art and design, microfluidics, molds, among others. In various embodiments, the telechelic polymers of the present disclosure can be used in the production of medical devices. Such medical devices include, in various embodiments herein, orthodontic appliances.

Synthesis of Monomers and Telechelic Polymers

The present disclosure provides synthetic methods for producing a monomer (e.g., a terminal monomer) described herein. In some embodiments, the monomer according to Formula (I) of the present disclosure can be prepared as shown below in exemplary SCHEME 1:

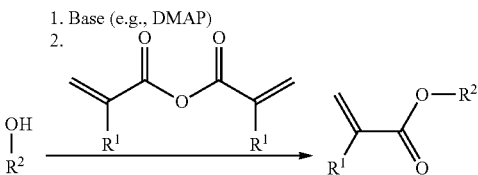

wherein,
$R^1$ is H, substituted or unsubstituted $C_{1-3}$ alkyl, or halogen; and
$R^2$ is substituted or unsubstituted $C_{1-6}$ alkyl, substituted or unsubstituted $C_{1-6}$ heteroalkyl, substituted or unsubstituted $C_{1-6}$ carbonyl, substituted or unsubstituted $C_{1-6}$ carboxy, substituted or unsubstituted aryl, substituted or unsubstituted heteroaryl, substituted or unsubstituted cyclo($C_{3-8}$) alkyl, or substituted or unsubstituted cyclo ($C_{3-8}$) heteroalkyl. In some instances, le is H or methyl. In some instances, $R^2$ is $C_{1-6}$ alkyl, $C_{1-6}$ heteroalkyl, substituted or unsubstituted aryl, or substituted or unsubstituted heteroaryl.

In some embodiments, any of such methods can comprise isolating a (e.g., terminal) monomer with a chemical yield of at least about 25%, 30%, 40%, 50%, 60%, 70%, 80%, 90%, or at least about 95%, and a purity of at least about 90%, 95%, or 99%.

One of skill in the art may appreciate that the substituents (e.g., $R^2$, etc.) can be altered before, during or after preparation of the phenyl acrylate scaffolding and that suitable adjustments in the exemplary conditions (e.g., temperatures, solvents, etc.) can be made. Additionally, one of skill in the art may recognize that protecting groups may be necessary for the preparation of certain compounds and may be aware of those conditions compatible with a selected protecting group.

In some embodiments, provided herein are methods for synthesizing a telechelic polymer. In some instances, a method of synthesizing a telechelic block copolymer, comprising coupling a telechelic polymer (A) to a second telechelic polymer (B), thereby producing the telechelic block copolymer, wherein the telechelic block copolymer comprises photopolymerizable end groups at its termini, and wherein the telechelic block copolymer has a number-average molecular weight of at most about 50 kDa. A telechelic polymer consisting of a single monomer species A or B can be synthesized using various polymerization techniques, such as any of the known controlled living polymerization methods such as Atom Transfer Radical Polymerization (ATRP), Reversible Addition Fragmentation chain transfer polymerization (RAFT), anionic polymerization.

A first telechelic polymer consisting of a single monomer species A can be coupled to a second telechelic polymer consisting of a single monomer species B to produce a telechelic block copolymer that may be used as a component in a photo-curable resin. Such coupling methods can comprise condensation reactions and substitution reactions, Diels-Alder reactions, and photodimerization reactions to couple preformed polymer blocks.

A method provided herein for producing a polymeric material of the present disclosure can comprise using a telechelic polymer as the only polymerization component in a photo-curable resin, or as a polymerization component in addition to various other polymerizable compounds present in such photo-curable resin. As described herein, methods of producing polymeric materials contemplate using only one species of telechelic polymer or a plurality of species of different telechelic polymers. Any one or more of such telechelic polymers can be telechelic block copolymers as described herein. Such telechelic block copolymer can comprise 2, 3, 4, 5 or more blocks of monomer species, wherein such monomer block are arranged in a specific configuration within the polymer. Any of such monomer block can also range in size, e.g., in the number of coupled monomers within a block. For example, telechelic block copolymers used herein can comprise 2, 3, 4, 5 or more blocks of monomer species, wherein each monomer block can comprise or consist of 5, 10, 15, 20, 25, 50, 75, 100, or more identical monomers that are linearly coupled to one another to form the monomer block.

In some embodiments, a telechelic polymer (e.g., di(meth)acryloyl-terminated poly(isobornyl acrylate), (4)) of the present disclosure can be prepared as shown below in exemplary SCHEME 2, using a monomer (1) according to Formula (I) of the present disclosure, and terminal endgroup modification to generate a telechelic polymer capable of undergoing further polymerization (e.g., photo-polymerization reactions) and comprising terminal monomers comprising a reactive moiety (e.g., a photo-reactive moiety):

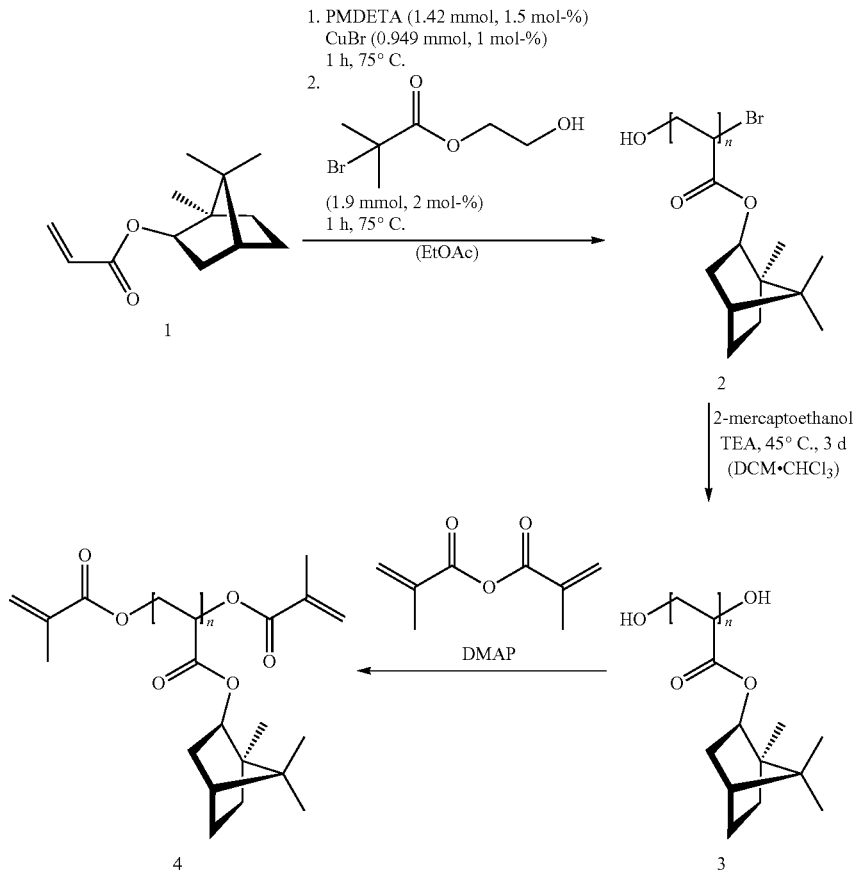

Methods of Forming Polymeric Materials

The present disclosure provides methods of forming a polymeric material, the method comprising: providing the photo-curable resin of the present disclosure comprising one or more telechelic polymers of the present disclosure; exposing the photo-curable resin to a light source; and curing the photo-curable resin to form the polymeric material. In some instances, a photo-curable resin herein can optionally comprise one or more further components selected from the group consisting of telechelic oligomers, polymerizable monomers (e.g., reactive diluents), polymerization initiators, polymerization inhibitors, solvents, fillers, antioxidants, pigments, colorants, surface modifiers, and mixtures thereof, to obtain an optionally cross-linked polymer, and thus a method herein can further comprise a step of mixing the curable composition, optionally after heating. As described herein, such method of forming a polymeric material can further comprise inducing through polymerization the generation of one or more polymeric phases. Thus, in some embodiments, a polymeric material of the present disclosure can comprise a one or more polymeric phases. In some instances, at least one polymeric phase of the one or more polymeric phases can comprise an amorphous polymeric material. In some instances, at least one polymeric phase of the one or more polymeric phases generated during photo-curing can comprise a crystalline polymeric material. In such instances, the crystalline polymeric material can have a melting point of at least about 50° C., 60° C., 80° C., 90° C., 100° C., or at least about 110° C. In some instances, at least one polymeric phase of the one or more polymeric phases can have a glass transition temperature ($T_g$) of at least about 50° C., 60° C., 80° C., 90° C., 100° C., or at least about 110° C. In some instances, at least one polymeric phase of the one or more polymeric phases can comprise a crystalline polymeric material and can have a melting point of at least about 50° C., 60° C., 80° C., 90° C., 100° C., or at least about 110° C., a glass transition temperature ($T_g$) of at least about 50° C., 60° C., 80° C., 90° C., 100° C., or at least about 110° C., or a combination thereof. In some aspects, a polymeric phase having a glass transition temperature ($T_g$) of at least about 50° C., 60° C., 80° C., 90° C., 100° C., or at least 110° C. can comprise a telechelic polymer of the present disclosure, in a polymerized from, e.g., a telechelic block copolymer. As described herein, the photopolymerizable composition present in the photo-curable resin can alter the degree of phase separation in the formed polymeric material during polymerization, as well as the number, sizes and/or physicochemical properties of such phases. For example, the block configuration of a telechelic block polymer used as part of a photo-curable resin can modify the intramolecular and intermolecular interactions within a polymer chain or between different polymer chains, respectively. In some instances, the design of a specific copolymer structure can be used to control the relative orientation and alignment of polymer chains within the polymeric material, and thereby control phase separation and downstream the mechanical properties of the resulting polymeric material. Furthermore, the chemical structure and molecular size of both the backbone and, in particular, the monomer side groups can impact and be rationally designed to control (e.g., through steric effects) the polymer chain arrangement and interactions, and thereby control phase separation and mechanical properties of the photo-cured polymeric material, such as tensile modulus, flexural stress, or elongation at break.

In some embodiments, the photo-curing comprises a single curing step. In some embodiments, the photo-curing comprises a plurality of curing steps. In yet other embodiments, the photo-curing comprises at least one curing step which exposes the curable resin to light. Exposing the curable resin to light can initiate and/or facilitate photopolymerization. In some instances, a photoinitiator can be used as part of the resin to accelerate and/or initiate photopolymerization. In some embodiments, the resin is exposed to UV (ultraviolet) light, visible light, IR (infrared) light, or any combination thereof. In some embodiments, the cured polymeric material is formed from the photo-curable resin using at least one step comprising exposure to a light source, wherein the light source comprises UV light, visible light, and/or IR light. In some embodiments, the light source comprises a wavelength from 10 nm to 200 nm, from 200 nm to 350 nm, from 350 nm to 450 nm, from 450 nm to 550 nm, from 550 nm to 650 nm, from 650 nm to 750 nm, from 750 nm to 850 nm, from 850 nm to 1000 nm, or from 1000 nm to 1500 nm.

The methods provided herein can be used to produce a polymeric material that can be characterized by one or more of the following properties as further described herein: (i) a tensile modulus greater than or equal to 200 MPa; (ii) a flexural stress and/or flexural modulus of greater than or equal to 1.5 MPa remaining after 24 hours in a wet environment at 37° C.; and (iii) an elongation at break greater than or equal to 5%. In various instances, such methods can further comprise fabricating a medical device with the polymeric material. In various instances, the produced medical device is an orthodontic appliance. Such orthodontic appliance can a dental aligner, a dental expander or a dental spacer. Such fabricating can comprise additive manufacturing.

Hence, in some embodiments, a method provided herein can be part of a high temperature lithography-based photopolymerization process, wherein a curable composition, e.g., those comprising a telechelic block copolymer described herein, can further comprise at least one photopolymerization initiator which, upon irradiation with light of a suitable wavelength to be absorbed, is cleaved, which results in cleavage products at least one of which is able to induce polymerization of the curable composition, which polymerization reaction preferably is part of an additive manufacturing process, more preferably a 3D printing process. Consequently, the photo-initiator should be compatible with the at least one polymerizable species and the reactive diluent, i.e., the polymerizable monomers of the disclosure. Being part of a high temperature photopolymerization process, some embodiments of such methods can comprise a step of heating the curable formulation containing the polymerizable monomer(s) of the disclosure as reactive diluent to a predefined elevated process temperature ranging from 50° C. to 120° C., such as from 90° C. to 120° C., before it is irradiated to induce polymerization resulting in optionally crosslinked polymers.

In certain aspects, a solid or highly viscous resin formulation comprising a photo-curable composition and at least one photoinitiator is heated to a predefined elevated process temperature and is subsequently irradiated with light of a suitable wavelength to be absorbed by the photoinitiator, thereby polymerizing and/or crosslinking the curable composition to obtain said crosslinked polymer or polymeric material. In some aspects, said elevated process temperature ranges from 50° C. to 120° C. In certain aspects, said elevated process temperature ranges from 90° C. to 120° C. In some aspects, said photopolymerization process is a direct or additive manufacturing process. In certain aspects, said photopolymerization process is a 3D printing process.

In further embodiments, a method herein can comprise polymerizing a curable composition which comprises at least one multivalent monomer and is polymerized to give a crosslinked polymer which comprises moieties originating from the polymerizable monomer(s) of the present disclosure as repeating units. In order to obtain crosslinked polymers which can be particularly suitable as orthodontic appliances, the at least one polymerizable species used in the method according to the present disclosure can be selected with regard to several thermomechanical properties of the resulting polymers. First, at least one, preferably, however, more than one, multivalent polymerizable species can be included. Second, the amounts of the polymerizable species and the reactive diluent, i.e. the polymerizable monomer(s) of the present disclosure, can be well balanced. And third, the polymerizable monomer(s) of the present disclosure used as reactive diluent(s) can be selected so as to contribute to the thermomechanical properties of the polymers.

In some embodiments, the crosslinked polymers can be characterized by a tensile stress-strain curve that displays a yield point after which the test specimen continues to elongate, but there is no (detectable) or only a very low increase in stress. Such yield point behavior typically occurs "near" the glass transition temperature, where the material is between the glassy and rubbery regimes and may be characterized as having viscoelastic behavior. In some embodiments, viscoelastic behavior is observed in the temperature range 20° C. to 40° C. The yield stress is determined at the yield point. In some embodiments, the modulus is determined from the initial slope of the stress-strain curve or as the secant modulus at 1% strain (e.g. when there is no linear portion of the stress-strain curve). The elongation at yield is determined from the strain at the yield point. When the yield point occurs at a maximum in the stress, the ultimate tensile strength is less than the yield strength. For a tensile test specimen, the strain is defined by $\ln(l/l_0)$, which may be approximated by $(l-l_0)/l_0$ at small strains (e.g. less than approximately 10%) and the elongation is $l/l_0$, where $l$ is the gauge length after some deformation has occurred and $l_0$ is the initial gauge length. The mechanical properties can depend on the temperature at which they are measured. The test temperature may be below the expected use temperature for an orthodontic appliance such as 35° C. to 40° C. In embodiments, the test temperature is 23±2° C.

Generally, as described herein, photopolymerization of the various components (e.g., polymers and monomers) present in a photo-curable resin can occur when suitable formulations are exposed to radiation (e.g., UV or visible light) of sufficient power and of a wavelength capable of initiating polymerization. The wavelengths and/or power of radiation useful to initiate polymerization may depend on the photoinitiator used. "Light", as used herein, generally includes any wavelength and power capable of initiating polymerization. Some wavelengths of light include ultraviolet (UV) or visible. UV light sources include UVA (wavelength about 400 nanometers (nm) to about 320 nm), UVB (about 320 nm to about 290 nm) or UVC (about 290 nm to about 100 nm). Any suitable source may be used, including laser sources. The source may be broadband or narrowband, or a combination thereof. The light source may provide continuous or pulsed light during the process. Both the length of time the system is exposed to UV light and the intensity of the UV light can be varied to determine the ideal reaction conditions.

Additive manufacturing, as used herein, includes a variety of technologies which can fabricate three-dimensional objects directly from digital models through an additive process. In some aspects, successive layers of material are deposited and "cured in place". A variety of techniques are known to the art for additive manufacturing, including selective laser sintering (SLS), fused deposition modeling (FDM) and jetting or extrusion. In many embodiments, selective laser sintering involves using a laser beam to selectively melt and fuse a layer of powdered material according to a desired cross-sectional shape in order to build up the object geometry. In many embodiments, fused deposition modeling involves melting and selectively depositing a thin filament of thermoplastic polymer in a layer-by-layer manner in order to form an object. In yet another example, 3D printing can be used to fabricate the appliances herein. In many embodiments, 3D printing involves jetting or extruding one or more materials onto a build surface in order to form successive layers of the object geometry. In some embodiments, the polymerizable monomers described herein can be used in inkjet or coating applications.

In some instances, photopolymers may be fabricated by "vat" processes in which light is used to selectively cure a vat or reservoir of the photopolymer. Each layer of photopolymer may be selectively exposed to light in a single exposure or by scanning a beam of light across the layer. Specific techniques include stereolithography (SLA), Digital Light Processing (DLP) and two photon-induced photopolymerization (TPIP).

A direct fabrication process can achieve continuous buildup of an object geometry by continuous movement of the build platform (e.g., along the vertical or Z-direction) during the irradiation phase, such that the hardening depth of the irradiated photopolymer is controlled by the movement speed. Accordingly, continuous polymerization of material on the build surface can be achieved. Such methods are described in U.S. Pat. No. 7,892,474, the disclosure of which is incorporated herein by reference in its entirety. In yet another example, a continuous direct fabrication method utilizes a "heliolithography" approach in which the liquid photopolymer is cured with focused radiation while the build platform is continuously rotated and raised. Accordingly, the object geometry can be continuously built up along a spiral build path. Such methods are described in U.S. Patent Publication No. 2014/0265034, the disclosure of which is incorporated herein by reference in its entirety. Continuous liquid interface production of 3D objects has also been reported (J. Tumbleston et al., Science, 2015, 347 (6228), pp 1349-1352) hereby incorporated by reference in its entirety for description of the process. Another example of continuous direct fabrication method can involve extruding a composite material composed of a curable liquid material surrounding a solid strand. The composite material can be extruded along a continuous three-dimensional path in order to form the object. Such methods are described in U.S. Patent Publication No. 2014/0061974, the disclosure of which is incorporated herein by reference in its entirety.

"High temperature lithography," as used herein, may refer to any lithography-based photo-polymerization processes that involve heating photopolymerizable material(s). The heating may lower the viscosity of the photopolymerizable material(s) before and/or during curing. Non-limiting examples of high-temperature lithography processes include those processes described in WO 2015/075094, WO 2016/078838 and WO 2018/032022. In some implementations, high-temperature lithography may involve applying heat to material to temperatures between 50° C.-120° C., such as 90° C.-120° C., 100° C.-120° C., 105° C.-115° C., 108° C.-110° C., etc. The material may be heated to temperatures greater than 120° C. It is noted other ranges may be used without departing from the scope and substance of the inventive concepts described herein.

Fabrication and Use of Orthodontic Appliances

Provided herein are methods for using the telechelic polymers, curable resins and compositions comprising such polymers, as well as polymeric materials produced from such resins and composition for the fabrication of a medical device, such as an orthodontic appliance (e.g., a dental aligner, a dental expander or a dental spacer).

Thus, in some embodiments, a method herein further comprises the step of fabricating a device or an object using an additive manufacturing device, wherein the additive manufacturing device facilitates the curing. In some embodiments, the curing of a polymerizable resin produces the cured polymeric material. In certain embodiments, a polymerizable resin is cured using an additive manufacturing device to produce the cured polymeric material. In some embodiments, the method further comprises the step of cleaning the cured polymeric material. In certain embodiments, the cleaning of the cured polymeric material includes washing and/or rinsing the cured polymeric material with a solvent, which can remove uncured resin and undesired impurities from the cured polymeric material. In some embodiments, a polymerizable resin herein can be curable and have melting points <100° C. in order to be liquid and, thus, processable at the temperatures usually employed in currently available additive manufacturing techniques as described herein.

Since, in some cases, the polymerizable monomers of the present disclosure can, as part of a photo-curable resin, become co-polymerized in the polymerization process of a method according to the present disclosure, the result can be an optionally cross-linked polymer comprising moieties of one or more species of polymerizable monomer(s) as repeating units. In some cases, such polymer is a cross-linked polymer which, typically, can be suitable and useful for applications in orthodontic appliances.

VI. Orthodontic Appliances

The photopolymerizable telechelic polymers (e.g., block copolymers) according to the present disclosure, e.g., those comprising, in a polymerized form, monomers according to Formulas (I) and (II), as well as telechelic block copolymers, e.g., one according to Formula (III) herein, can be used as part of photo-curable resins and can, in some instances, result in polymeric materials having favorable thermomechanical properties for use in medical devices, such as orthodontic appliances, for example, for moving one or more teeth. Hence, provided herein are medical devices comprising a polymeric material or a polymeric film of the present disclosure. In various instances, the medical device is an orthodontic appliance. Such orthodontic appliances can include dental aligners, a dental expanders and dental spacers. In various cases, such orthodontic appliance can be used for moving one or more teeth of a human subject. In various embodiments, a medical device (e.g., an orthodontic appliance) herein can be produced by additive manufacturing. In some aspects, fabricating the medical device (e.g., an orthodontic appliance) with the polymeric material comprises printing with a 3D printer. In some aspects, fabricating the device with the polymeric material comprises digital light projection. In some aspects, fabricating the device with the polymeric material comprises high temperature lithography.

As described herein, the present disclosure also provides a method of repositioning a patient's teeth, the method comprising: (i) generating a treatment plan for the patient, the plan comprising a plurality of intermediate tooth arrangements for moving teeth along a treatment path from an initial tooth arrangement toward a final tooth arrangement; (ii) producing a dental appliance comprising a polymeric material described herein, e.g., a polymeric material that comprises one or more telechelic polymers of the present disclosure; and moving on-track, with the dental appliance, at least one of the patient's teeth toward an intermediate tooth arrangement or the final tooth arrangement. Such dental appliance can be produced using processes that include 3D printing, as further described herein. The method of repositioning a patient's teeth can further comprise tracking progression of the patient's teeth along the treatment path after administration of the dental appliance to the patient, the tracking comprising comparing a current arrangement of the patient's teeth to a planned arrangement of the patient's teeth. In such instances, greater than 60% of the patient's teeth can be on track with the treatment plan after 2 weeks of treatment. In some instances, the dental appliance has a retained repositioning force to the at least one of the patient's teeth after 2 days that is at least 10%, at least 20%, at least 30%, at least 40%, at least 50%, at least 60%, or at least 70% of repositioning force initially provided to the at least one of the patient's teeth.

As used herein, the terms "rigidity" and "stiffness" can be used interchangeably, as are the corresponding terms "rigid" and "stiff."

As used herein a "plurality of teeth" encompasses two or more teeth.

In many embodiments, one or more posterior teeth comprises one or more of a molar, a premolar or a canine, and one or more anterior teeth comprising one or more of a central incisor, a lateral incisor, a cuspid, a first bicuspid or a second bicuspid.

In some embodiments, the compositions and methods described herein can be used to couple groups of one or more teeth to each other. The groups of one or more teeth may comprise a first group of one or more anterior teeth and a second group of one or more posterior teeth. The first group of teeth can be coupled to the second group of teeth with the polymeric shell appliances as disclosed herein.

The embodiments disclosed herein are well suited for moving one or more teeth of the first group of one or more teeth or moving one or more of the second group of one or more teeth, and combinations thereof.

The embodiments disclosed herein are well suited for combination with one or more known commercially available tooth moving components such as attachments and polymeric shell appliances. In many embodiments, the appliance and one or more attachments are configured to move one or more teeth along a tooth movement vector comprising six degrees of freedom, in which three degrees of freedom are rotational and three degrees of freedom are translation.

The present disclosure provides orthodontic systems and related methods for designing and providing improved or more effective tooth moving systems for eliciting a desired tooth movement and/or repositioning teeth into a desired arrangement.

Although reference is made to an appliance comprising a polymeric shell appliance, the embodiments disclosed herein are well suited for use with many appliances that receive teeth, for example appliances without one or more of polymers or shells. The appliance can be fabricated with one or more of many materials such as metal, glass, reinforced fibers, carbon fiber, composites, reinforced composites, aluminum, biological materials, and combinations thereof, for example. In some cases, the reinforced composites can comprise a polymer matrix reinforced with ceramic or metallic particles, for example. The appliance can be shaped in many ways, such as with thermoforming or direct fabrication as described herein, for example. Alternatively, or in combination, the appliance can be fabricated with machining such as an appliance fabricated from a block of material with computer numeric control machining. Preferably, the appliance is fabricated using a polymerizable monomer according to the present disclosure, for example, using the monomers as reactive diluents for curable resins.

Turning now to the drawings, in which like numbers designate like elements in the various figures, FIG. 1A illustrates an exemplary tooth repositioning appliance or aligner 100 that can be worn by a patient in order to achieve an incremental repositioning of individual teeth 102 in the jaw. The appliance can include a shell (e.g., a continuous polymeric shell or a segmented shell) having teeth-receiving cavities that receive and resiliently reposition the teeth. An appliance or portion(s) thereof may be indirectly fabricated using a physical model of teeth. For example, an appliance (e.g., polymeric appliance) can be formed using a physical model of teeth and a sheet of suitable layers of polymeric material. In some embodiments, a physical appliance is directly fabricated, e.g., using rapid prototyping fabrication techniques, from a digital model of an appliance. An appliance can fit over all teeth present in an upper or lower jaw, or less than all of the teeth. The appliance can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the appliance can be a generic appliance configured to receive the teeth, but not necessarily shaped to match the topography of the patient's teeth. In some cases, only certain teeth received by an appliance will be repositioned by the appliance while other teeth can provide a base or anchor region for holding the appliance in place as it applies force against the tooth or teeth targeted for repositioning. In some cases, some, most, or even all of the teeth will be repositioned at some point during treatment. Teeth that are moved can also serve as a base or anchor for holding the appliance as it is worn by the patient. Typically, no wires or other means will be provided for holding an appliance in place over the teeth. In some cases, however, it may be desirable or necessary to provide individual attachments or other anchoring elements 104 on teeth 102 with corresponding receptacles or apertures 106 in the appliance 100 so that the appliance can apply a selected force on the tooth. Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the url "invisalign.com"). Examples of tooth-mounted attachments suitable for use with orthodontic appliances are also described in patents and patent applications assigned to Align Technology, Inc., including, for example, U.S. Pat. Nos. 6,309,215 and 6,830,450.

Figure 1B:
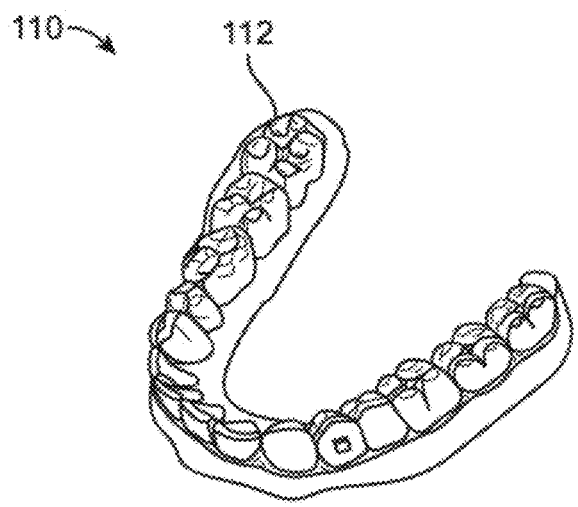
FIG. 1B illustrates a tooth repositioning system, in accordance with embodiments.
Figure 1B:
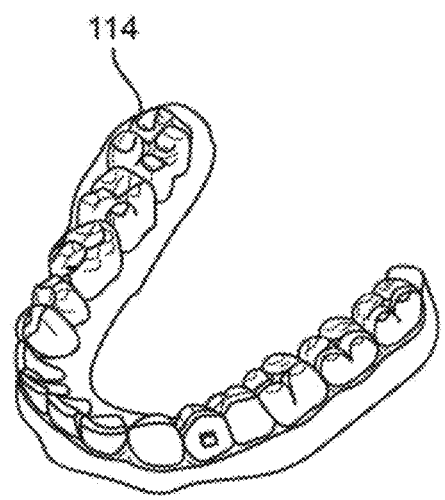
Figure 1B:
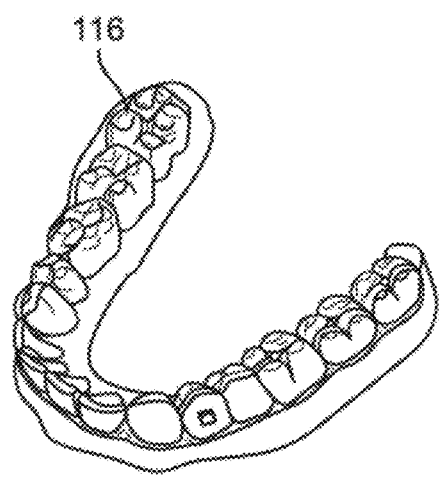

FIG. 1B illustrates a tooth repositioning system 110 including a plurality of appliances 112, 114, 116. Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. For example, the tooth repositioning system 110 can include a first appliance 112 corresponding to an initial tooth arrangement, one or more intermediate appliances 114 corresponding to one or more intermediate arrangements, and a final appliance 116 corresponding to a target arrangement. A target tooth arrangement can be a planned final tooth arrangement selected for the patient's teeth at the end of all planned orthodontic treatment. Alternatively, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

Figure 1C:
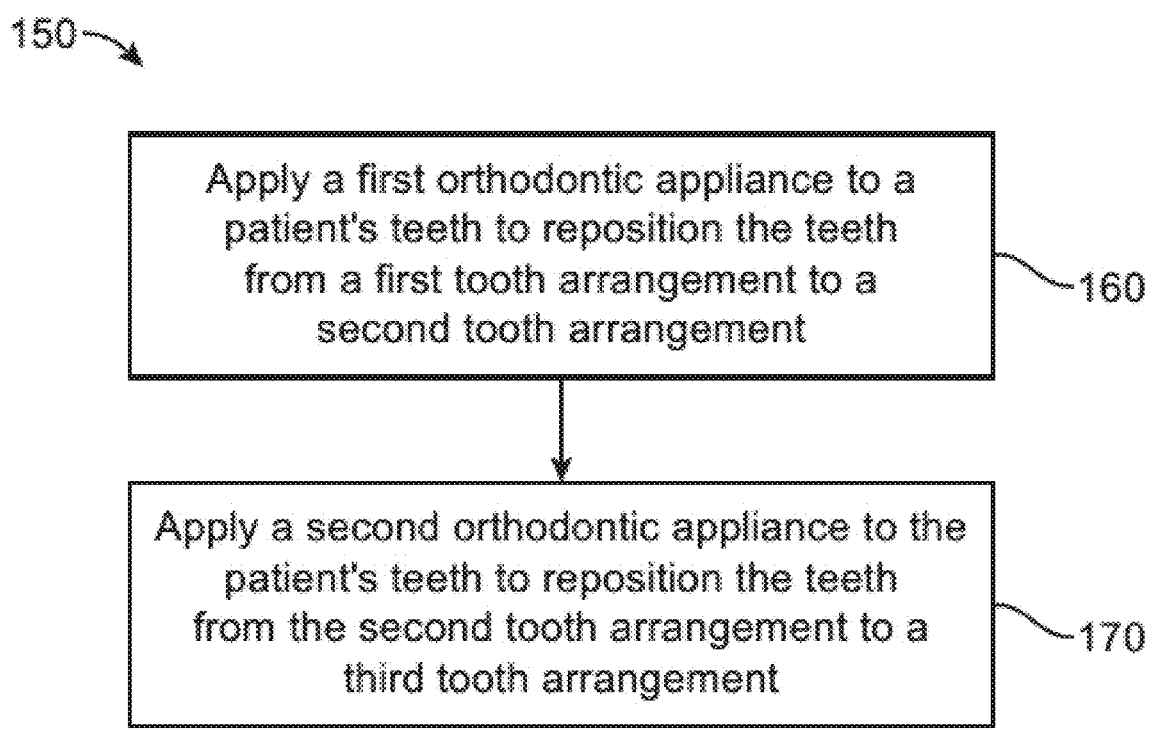
FIG. 1C illustrates a method of orthodontic treatment using a plurality of appliances, in accordance with embodiments.

FIG. 1C illustrates a method 150 of orthodontic treatment using a plurality of appliances, in accordance with embodiments. The method 150 can be practiced using any of the appliances or appliance sets described herein. In step 160, a first orthodontic appliance is applied to a patient's teeth in order to reposition the teeth from a first tooth arrangement to a second tooth arrangement. In step 170, a second orthodontic appliance is applied to the patient's teeth in order to reposition the teeth from the second tooth arrangement to a third tooth arrangement. The method 150 can be repeated as necessary using any suitable number and combination of sequential appliances in order to incrementally reposition the patient's teeth from an initial arrangement to a target arrangement. The appliances can be generated all at the same stage or in sets or batches (e.g., at the beginning of a stage of the treatment), or the appliances can be fabricated one at a time, and the patient can wear each appliance until the pressure of each appliance on the teeth can no longer be felt or until the maximum amount of expressed tooth movement for that given stage has been achieved. A plurality of different appliances (e.g., a set) can be designed and even fabricated prior to the patient wearing any appliance of the plurality. After wearing an appliance for an appropriate period of time, the patient can replace the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement. For instance, one or more appliances may have a geometry that would (if fully achieved) move individual teeth beyond the tooth arrangement that has been selected as the "final." Such over-correction may be desirable in order to offset potential relapse after the repositioning method has been terminated (e.g., permit movement of individual teeth back toward their pre-corrected positions). Over-correction may also be beneficial to speed the rate of correction (e.g., an appliance with a geometry that is positioned beyond a desired intermediate or final position may shift the individual teeth toward the position at a greater rate). In such cases, the use of an appliance can be terminated before the teeth reach the positions defined by the appliance. Furthermore, over-correction may be deliberately applied in order to compensate for any inaccuracies or limitations of the appliance.

The various embodiments of the orthodontic appliances presented herein can be fabricated in a wide variety of ways. In some embodiments, the orthodontic appliances herein (or portions thereof) can be produced using direct fabrication, such as additive manufacturing techniques (also referred to herein as "3D printing") or subtractive manufacturing techniques (e.g., milling). In some embodiments, direct fabrication involves forming an object (e.g., an orthodontic appliance or a portion thereof) without using a physical template (e.g., mold, mask etc.) to define the object geometry. Additive manufacturing techniques can be categorized as follows: (1) vat photopolymerization (e.g., stereolithography), in which an object is constructed layer by layer from a vat of liquid photopolymer resin; (2) material jetting, in which material is jetted onto a build platform using either a continuous or drop on demand (DOD) approach; (3) binder jetting, in which alternating layers of a build material (e.g., a powder-based material) and a binding material (e.g., a liquid binder) are deposited by a print head; (4) fused deposition modeling (FDM), in which material is drawn though a nozzle, heated, and deposited layer by layer; (5) powder bed fusion, including but not limited to direct metal laser sintering (DMLS), electron beam melting (EBM), selective heat sintering (SHS), selective laser melting (SLM), and selective laser sintering (SLS); (6) sheet lamination, including but not limited to laminated object manufacturing (LOM) and ultrasonic additive manufacturing (UAM); and (7) directed energy deposition, including but not limited to laser engineering net shaping, directed light fabrication, direct metal deposition, and 3D laser cladding. For example, stereolithography can be used to directly fabricate one or more of the appliances herein. In some embodiments, stereolithography involves selective polymerization of a photosensitive resin (e.g., a photopolymer) according to a desired cross-sectional shape using light (e.g., ultraviolet light). The object geometry can be built up in a layer-by-layer fashion by sequentially polymerizing a plurality of object cross-sections. As another example, the appliances herein can be directly fabricated using selective laser sintering. In some embodiments, selective laser sintering involves using a laser beam to selectively melt and fuse a layer of powdered material according to a desired cross-sectional shape in order to build up the object geometry. As yet another example, the appliances herein can be directly fabricated by fused deposition modeling. In some embodiments, fused deposition modeling involves melting and selectively depositing a thin filament of thermoplastic polymer in a layer-by-layer manner in order to form an object. In yet another example, material jetting can be used to directly fabricate the appliances herein. In some embodiments, material jetting involves jetting or extruding one or more materials onto a build surface in order to form successive layers of the object geometry.

Alternatively, or in combination, some embodiments of the appliances herein (or portions thereof) can be produced using indirect fabrication techniques, such as by thermoforming over a positive or negative mold. Indirect fabrication of an orthodontic appliance can involve producing a positive or negative mold of the patient's dentition in a target arrangement (e.g., by rapid prototyping, milling, etc.) and thermoforming one or more sheets of material over the mold in order to generate an appliance shell.

In some embodiments, the direct fabrication methods provided herein build up the object geometry in a layer-by-layer fashion, with successive layers being formed in discrete build steps. Alternatively, or in combination, direct fabrication methods that allow for continuous build-up of an object geometry can be used, referred to herein as "continuous direct fabrication." Various types of continuous direct fabrication methods can be used. As an example, in some embodiments, the appliances herein are fabricated using "continuous liquid interphase printing," in which an object is continuously built up from a reservoir of photopolymerizable resin by forming a gradient of partially cured resin between the building surface of the object and a polymerization-inhibited "dead zone." In some embodiments, a semi-permeable membrane is used to control transport of a photopolymerization inhibitor (e.g., oxygen) into the dead zone in order to form the polymerization gradient. Continuous liquid interphase printing can achieve fabrication speeds about 25 times to about 100 times faster than other direct fabrication methods, and speeds about 1000 times faster can be achieved with the incorporation of cooling systems. Continuous liquid interphase printing is described in U.S. Patent Publication Nos. 2015/0097315, 2015/0097316, and 2015/0102532, the disclosures of each of which are incorporated herein by reference in their entirety.

As another example, a continuous direct fabrication method can achieve continuous build-up of an object geometry by continuous movement of the build platform (e.g., along the vertical or Z-direction) during the irradiation phase, such that the hardening depth of the irradiated photopolymer is controlled by the movement speed. Accordingly, continuous polymerization of material on the build surface can be achieved. Such methods are described in U.S. Pat. No. 7,892,474, the disclosure of which is incorporated herein by reference in its entirety.

In another example, a continuous direct fabrication method can involve extruding a composite material composed of a curable liquid material surrounding a solid strand. The composite material can be extruded along a continuous three-dimensional path in order to form the object. Such methods are described in U.S. Patent Publication No. 2014/0061974, the disclosure of which is incorporated herein by reference in its entirety.

In yet another example, a continuous direct fabrication method utilizes a "heliolithography" approach in which the liquid photopolymer is cured with focused radiation while the build platform is continuously rotated and raised. Accordingly, the object geometry can be continuously built up along a spiral build path. Such methods are described in U.S. Patent Publication No. 2014/0265034, the disclosure of which is incorporated herein by reference in its entirety.

The direct fabrication approaches provided herein are compatible with a wide variety of materials, including but not limited to one or more of the following: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, a polytrimethylene terephthalate, a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, a thermoplastic polyamide elastomer, a thermoset material, or combinations thereof. The materials used for direct fabrication can be provided in an uncured form (e.g., as a liquid, resin, powder, etc.) and can be cured (e.g., by photopolymerization, light curing, gas curing, laser curing, crosslinking, etc.) in order to form an orthodontic appliance or a portion thereof. The properties of the material before curing may differ from the properties of the material after curing. Once cured, the materials herein can exhibit sufficient strength, stiffness, durability, biocompatibility, etc. for use in an orthodontic appliance. The post-curing properties of the materials used can be selected according to the desired properties for the corresponding portions of the appliance.

In some embodiments, relatively rigid portions of the orthodontic appliance can be formed via direct fabrication using one or more of the following materials: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, and/or a polytrimethylene terephthalate.

In some embodiments, relatively elastic portions of the orthodontic appliance can be formed via direct fabrication using one or more of the following materials: a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, and/or a thermoplastic polyamide elastomer.

Machine parameters can include curing parameters. For digital light processing (DLP)-based curing systems, curing parameters can include power, curing time, and/or grayscale of the full image. For laser-based curing systems, curing parameters can include power, speed, beam size, beam shape and/or power distribution of the beam. For printing systems, curing parameters can include material drop size, viscosity, and/or curing power. These machine parameters can be monitored and adjusted on a regular basis (e.g., some parameters at every 1-x layers and some parameters after each build) as part of the process control on the fabrication machine. Process control can be achieved by including a sensor on the machine that measures power and other beam parameters every layer or every few seconds and automatically adjusts them with a feedback loop. For DLP machines, gray scale can be measured and calibrated before, during, and/or at the end of each build, and/or at predetermined time intervals (e.g., every $n^{th}$ build, once per hour, once per day, once per week, etc.), depending on the stability of the system. In addition, material properties and/or photo-characteristics can be provided to the fabrication machine, and a machine process control module can use these parameters to adjust machine parameters (e.g., power, time, gray scale, etc.) to compensate for variability in material properties. By implementing process controls for the fabrication machine, reduced variability in appliance accuracy and residual stress can be achieved.

Optionally, the direct fabrication methods described herein allow for fabrication of an appliance including multiple materials, referred to herein as "multi-material direct fabrication." In some embodiments, a multi-material direct fabrication method involves concurrently forming an object from multiple materials in a single manufacturing step. For instance, a multi-tip extrusion apparatus can be used to selectively dispense multiple types of materials from distinct material supply sources in order to fabricate an object from a plurality of different materials. Such methods are described in U.S. Pat. No. 6,749,414, the disclosure of which is incorporated herein by reference in its entirety. Alternatively, or in combination, a multi-material direct fabrication method can involve forming an object from multiple materials in a plurality of sequential manufacturing steps. For instance, a first portion of the object can be formed from a first material in accordance with any of the direct fabrication methods herein, then a second portion of the object can be formed from a second material in accordance with methods herein, and so on, until the entirety of the object has been formed.

Direct fabrication can provide various advantages compared to other manufacturing approaches. For instance, in contrast to indirect fabrication, direct fabrication permits production of an orthodontic appliance without utilizing any molds or templates for shaping the appliance, thus reducing the number of manufacturing steps involved and improving the resolution and accuracy of the final appliance geometry. Additionally, direct fabrication permits precise control over the three-dimensional geometry of the appliance, such as the appliance thickness. Complex structures and/or auxiliary components can be formed integrally as a single piece with the appliance shell in a single manufacturing step, rather than being added to the shell in a separate manufacturing step. In some embodiments, direct fabrication is used to produce appliance geometries that would be difficult to create using alternative manufacturing techniques, such as appliances with very small or fine features, complex geometric shapes, undercuts, interproximal structures, shells with variable thicknesses, and/or internal structures (e.g., for improving strength with reduced weight and material usage). For example, in some embodiments, the direct fabrication approaches herein permit fabrication of an orthodontic appliance with feature sizes of less than or equal to about 5 μm, or within a range from about 5 μm to about 50 μm, or within a range from about 20 μm to about 50 μm.

The direct fabrication techniques described herein can be used to produce appliances with substantially isotropic material properties, e.g., substantially the same or similar strengths along all directions. In some embodiments, the direct fabrication approaches herein permit production of an orthodontic appliance with a strength that varies by no more than about 25%, about 20%, about 15%, about 10%, about 5%, about 1%, or about 0.5% along all directions. Additionally, the direct fabrication approaches herein can be used to produce orthodontic appliances at a faster speed compared to other manufacturing techniques. In some embodiments, the direct fabrication approaches herein allow for production of an orthodontic appliance in a time interval less than or equal to about 1 hour, about 30 minutes, about 25 minutes, about 20 minutes, about 15 minutes, about 10 minutes, about 5 minutes, about 4 minutes, about 3 minutes, about 2 minutes, about 1 minutes, or about 30 seconds. Such manufacturing speeds allow for rapid "chair-side" production of customized appliances, e.g., during a routine appointment or checkup.

In some embodiments, the direct fabrication methods described herein implement process controls for various machine parameters of a direct fabrication system or device in order to ensure that the resultant appliances are fabricated with a high degree of precision. Such precision can be beneficial for ensuring accurate delivery of a desired force system to the teeth in order to effectively elicit tooth movements. Process controls can be implemented to account for process variability arising from multiple sources, such as the material properties, machine parameters, environmental variables, and/or post-processing parameters.

Material properties may vary depending on the properties of raw materials, purity of raw materials, and/or process variables during mixing of the raw materials. In many embodiments, resins or other materials for direct fabrication should be manufactured with tight process control to ensure little variability in photo-characteristics, material properties (e.g., viscosity, surface tension), physical properties (e.g., modulus, strength, elongation) and/or thermal properties (e.g., glass transition temperature, heat deflection temperature). Process control for a material manufacturing process can be achieved with screening of raw materials for physical properties and/or control of temperature, humidity, and/or other process parameters during the mixing process. By implementing process controls for the material manufacturing procedure, reduced variability of process parameters and more uniform material properties for each batch of material can be achieved. Residual variability in material properties can be compensated with process control on the machine, as discussed further herein.

Machine parameters can include curing parameters. For digital light processing (DLP)-based curing systems, curing parameters can include power, curing time, and/or grayscale of the full image. For laser-based curing systems, curing parameters can include power, speed, beam size, beam shape and/or power distribution of the beam. For printing systems, curing parameters can include material drop size, viscosity, and/or curing power. These machine parameters can be monitored and adjusted on a regular basis (e.g., some parameters at every 1-x layers and some parameters after each build) as part of the process control on the fabrication machine. Process control can be achieved by including a sensor on the machine that measures power and other beam parameters every layer or every few seconds and automatically adjusts them with a feedback loop. For DLP machines, gray scale can be measured and calibrated at the end of each build. In addition, material properties and/or photo-characteristics can be provided to the fabrication machine, and a machine process control module can use these parameters to adjust machine parameters (e.g., power, time, gray scale, etc.) to compensate for variability in material properties. By implementing process controls for the fabrication machine, reduced variability in appliance accuracy and residual stress can be achieved.

In many embodiments, environmental variables (e.g., temperature, humidity, Sunlight or exposure to other energy/curing source) are maintained in a tight range to reduce variability in appliance thickness and/or other properties. Optionally, machine parameters can be adjusted to compensate for environmental variables.

In many embodiments, post-processing of appliances includes cleaning, post-curing, and/or support removal processes. Relevant post-processing parameters can include purity of cleaning agent, cleaning pressure and/or temperature, cleaning time, post-curing energy and/or time, and/or consistency of support removal process. These parameters can be measured and adjusted as part of a process control scheme. In addition, appliance physical properties can be varied by modifying the post-processing parameters. Adjusting post-processing machine parameters can provide another way to compensate for variability in material properties and/or machine properties.

The configuration of the orthodontic appliances herein can be determined according to a treatment plan for a patient, e.g., a treatment plan involving successive administration of a plurality of appliances for incrementally repositioning teeth. Computer-based treatment planning and/or appliance manufacturing methods can be used in order to facilitate the design and fabrication of appliances. For instance, one or more of the appliance components described herein can be digitally designed and fabricated with the aid of computer-controlled manufacturing devices (e.g., computer numerical control (CNC) milling, computer-controlled rapid prototyping such as 3D printing, etc.). The computer-based methods presented herein can improve the accuracy, flexibility, and convenience of appliance fabrication.

Figure 2:
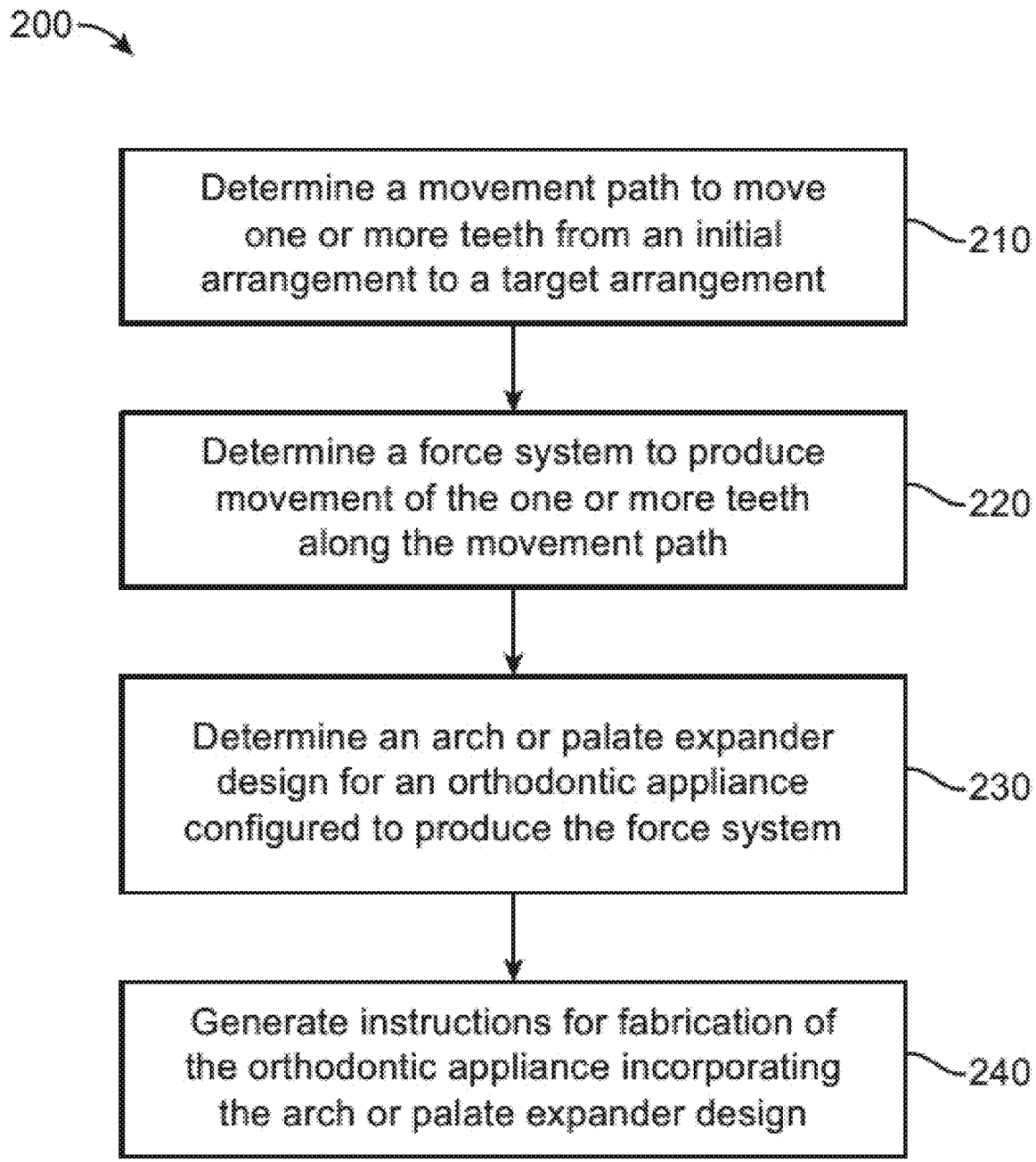
FIG. 2 illustrates a method for designing an orthodontic appliance, in accordance with embodiments.

FIG. 2 illustrates a method 200 for designing an orthodontic appliance to be produced by direct fabrication, in accordance with embodiments. The method 200 can be applied to any embodiment of the orthodontic appliances described herein. Some or all of the steps of the method 200 can be performed by any suitable data processing system or device, e.g., one or more processors configured with suitable instructions.

In step 210, a movement path to move one or more teeth from an initial arrangement to a target arrangement is determined. The initial arrangement can be determined from a mold or a scan of the patient's teeth or mouth tissue, e.g., using wax bites, direct contact scanning, x-ray imaging, tomographic imaging, sonographic imaging, and other techniques for obtaining information about the position and structure of the teeth, jaws, gums and other orthodontically relevant tissue. From the obtained data, a digital data set can be derived that represents the initial (e.g., pretreatment) arrangement of the patient's teeth and other tissues. Optionally, the initial digital data set is processed to segment the tissue constituents from each other. For example, data structures that digitally represent individual tooth crowns can be produced. Advantageously, digital models of entire teeth can be produced, including measured or extrapolated hidden surfaces and root structures, as well as surrounding bone and soft tissue.

The target arrangement of the teeth (e.g., a desired and intended end result of orthodontic treatment) can be received from a clinician in the form of a prescription, can be calculated from basic orthodontic principles, and/or can be extrapolated computationally from a clinical prescription. With a specification of the desired final positions of the teeth and a digital representation of the teeth themselves, the final position and surface geometry of each tooth can be specified to form a complete model of the tooth arrangement at the desired end of treatment.

Having both an initial position and a target position for each tooth, a movement path can be defined for the motion of each tooth. In some embodiments, the movement paths are configured to move the teeth in the quickest fashion with the least amount of round-tripping to bring the teeth from their initial positions to their desired target positions. The tooth paths can optionally be segmented, and the segments can be calculated so that each tooth's motion within a segment stays within threshold limits of linear and rotational translation. In this way, the end points of each path segment can constitute a clinically viable repositioning, and the aggregate of segment end points can constitute a clinically viable sequence of tooth positions, so that moving from one point to the next in the sequence does not result in a collision of teeth.

In step 220, a force system to produce movement of the one or more teeth along the movement path is determined. A force system can include one or more forces and/or one or more torques. Different force systems can result in different types of tooth movement, such as tipping, translation, rotation, extrusion, intrusion, root movement, etc. Biomechanical principles, modeling techniques, force calculation/measurement techniques, and the like, including knowledge and approaches commonly used in orthodontia, may be used to determine the appropriate force system to be applied to the tooth to accomplish the tooth movement. In determining the force system to be applied, sources may be considered including literature, force systems determined by experimentation or virtual modeling, computer-based modeling, clinical experience, minimization of unwanted forces, etc.

The determination of the force system can include constraints on the allowable forces, such as allowable directions and magnitudes, as well as desired motions to be brought about by the applied forces. For example, in fabricating palatal expanders, different movement strategies may be desired for different patients. For example, the amount of force needed to separate the palate can depend on the age of the patient, as very young patients may not have a fully-formed suture. Thus, in juvenile patients and others without fully-closed palatal sutures, palatal expansion can be accomplished with lower force magnitudes. Slower palatal movement can also aid in growing bone to fill the expanding suture. For other patients, a more rapid expansion may be desired, which can be achieved by applying larger forces. These requirements can be incorporated as needed to choose the structure and materials of appliances; for example, by choosing palatal expanders capable of applying large forces for rupturing the palatal suture and/or causing rapid expansion of the palate. Subsequent appliance stages can be designed to apply different amounts of force, such as first applying a large force to break the suture, and then applying smaller forces to keep the suture separated or gradually expand the palate and/or arch.

The determination of the force system can also include modeling of the facial structure of the patient, such as the skeletal structure of the jaw and palate. Scan data of the palate and arch, such as Xray data or 3D optical scanning data, for example, can be used to determine parameters of the skeletal and muscular system of the patient's mouth, so as to determine forces sufficient to provide a desired expansion of the palate and/or arch. In some embodiments, the thickness and/or density of the mid-palatal suture may be measured, or input by a treating professional. In other embodiments, the treating professional can select an appropriate treatment based on physiological characteristics of the patient. For example, the properties of the palate may also be estimated based on factors such as the patient's age—for example, young juvenile patients will typically require lower forces to expand the suture than older patients, as the suture has not yet fully formed.

In step 230, an arch or palate expander design for an orthodontic appliance configured to produce the force system is determined. Determination of the arch or palate expander design, appliance geometry, material composition, and/or properties can be performed using a treatment or force application simulation environment. A simulation environment can include, e.g., computer modeling systems, biomechanical systems or apparatus, and the like. Optionally, digital models of the appliance and/or teeth can be produced, such as finite element models. The finite element models can be created using computer program application software available from a variety of vendors. For creating solid geometry models, computer aided engineering (CAE) or computer aided design (CAD) programs can be used, such as the AutoCAD® software products available from Autodesk, Inc., of San Rafael, CA. For creating finite element models and analyzing them, program products from a number of vendors can be used, including finite element analysis packages from ANSYS, Inc., of Canonsburg, PA, and SIMULIA (Abaqus) software products from Dassault Systèmes of Waltham, MA.

Optionally, one or more arch or palate expander designs can be selected for testing or force modeling. As noted above, a desired tooth movement, as well as a force system required or desired for eliciting the desired tooth movement, can be identified. Using the simulation environment, a candidate arch or palate expander design can be analyzed or modeled for determination of an actual force system resulting from use of the candidate appliance. One or more modifications can optionally be made to a candidate appliance, and force modeling can be further analyzed as described, e.g., in order to iteratively determine an appliance design that produces the desired force system.

In step 240, instructions for fabrication of the orthodontic appliance incorporating the arch or palate expander design are generated. The instructions can be configured to control a fabrication system or device in order to produce the orthodontic appliance with the specified arch or palate expander design. In some embodiments, the instructions are configured for manufacturing the orthodontic appliance using direct fabrication (e.g., stereolithography, selective laser sintering, fused deposition modeling, 3D printing, continuous direct fabrication, multi-material direct fabrication, etc.), in accordance with the various methods presented herein. In alternative embodiments, the instructions can be configured for indirect fabrication of the appliance, e.g., by thermoforming.

Method 200 may comprise additional steps: 1) The upper arch and palate of the patient is scanned intraorally to generate three dimensional data of the palate and upper arch; 2) The three dimensional shape profile of the appliance is determined to provide a gap and teeth engagement structures as described herein.

Although the above steps show a method 200 of designing an orthodontic appliance in accordance with some embodiments, a person of ordinary skill in the art will recognize some variations based on the teaching described herein. Some of the steps may comprise sub-steps. Some of the steps may be repeated as often as desired. One or more steps of the method 200 may be performed with any suitable fabrication system or device, such as the embodiments described herein. Some of the steps may be optional, and the order of the steps can be varied as desired.

Figure 3:
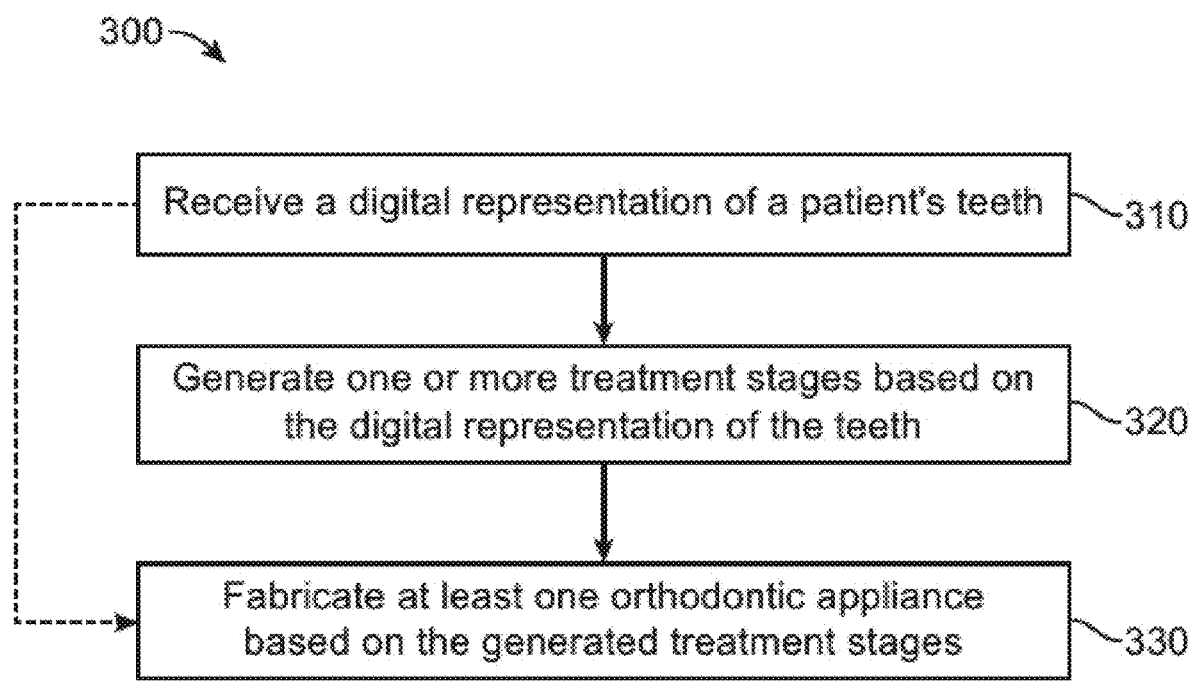
FIG. 3 illustrates a method for digitally planning an orthodontic treatment, in accordance with embodiments.

FIG. 3 illustrates a method 300 for digitally planning an orthodontic treatment and/or design or fabrication of an appliance, in accordance with embodiments. The method 300 can be applied to any of the treatment procedures described herein and can be performed by any suitable data processing system.

In step 310, a digital representation of a patient's teeth is received. The digital representation can include surface topography data for the patient's intraoral cavity (including teeth, gingival tissues, etc.). The surface topography data can be generated by directly scanning the intraoral cavity, a physical model (positive or negative) of the intraoral cavity, or an impression of the intraoral cavity, using a suitable scanning device (e.g., a handheld scanner, desktop scanner, etc.).

In step 320, one or more treatment stages are generated based on the digital representation of the teeth. The treatment stages can be incremental repositioning stages of an orthodontic treatment procedure designed to move one or more of the patient's teeth from an initial tooth arrangement to a target arrangement. For example, the treatment stages can be generated by determining the initial tooth arrangement indicated by the digital representation, determining a target tooth arrangement, and determining movement paths of one or more teeth in the initial arrangement necessary to achieve the target tooth arrangement. The movement path can be optimized based on minimizing the total distance moved, preventing collisions between teeth, avoiding tooth movements that are more difficult to achieve, or any other suitable criteria.

In step 330, at least one orthodontic appliance is fabricated based on the generated treatment stages. For example, a set of appliances can be fabricated, each shaped according a tooth arrangement specified by one of the treatment stages, such that the appliances can be sequentially worn by the patient to incrementally reposition the teeth from the initial arrangement to the target arrangement. The appliance set may include one or more of the orthodontic appliances described herein. The fabrication of the appliance may involve creating a digital model of the appliance to be used as input to a computer-controlled fabrication system. The appliance can be formed using direct fabrication methods, indirect fabrication methods, or combinations thereof, as desired.

In some instances, staging of various arrangements or treatment stages may not be necessary for design and/or fabrication of an appliance. As illustrated by the dashed line in FIG. 3, design and/or fabrication of an orthodontic appliance, and perhaps a particular orthodontic treatment, may include use of a representation of the patient's teeth (e.g., receive a digital representation of the patient's teeth 310), followed by design and/or fabrication of an orthodontic appliance based on a representation of the patient's teeth in the arrangement represented by the received representation.

On-Track Treatment

Figure 4:
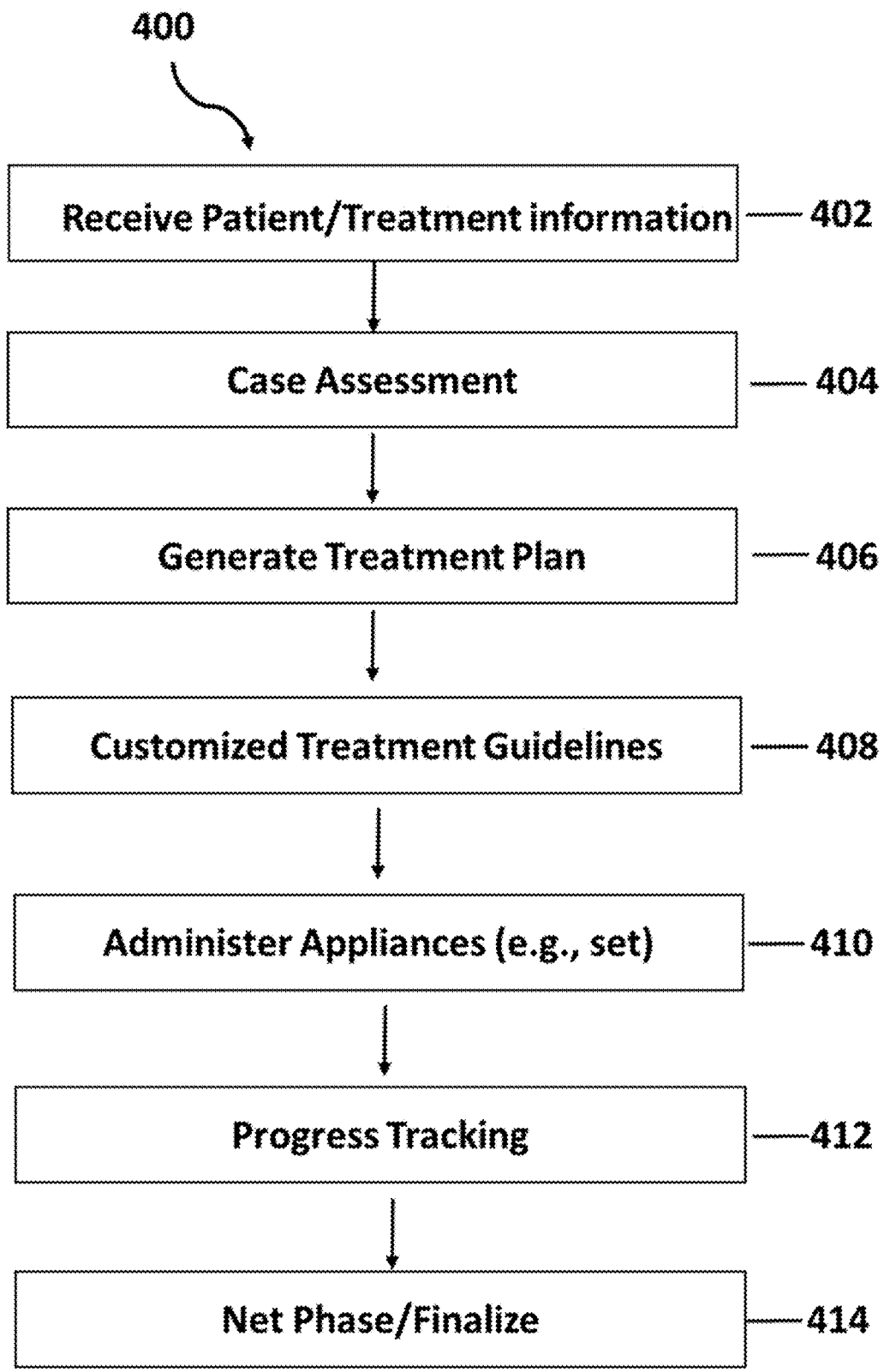
FIG. 4 shows generating and administering treatment according to an embodiment of the present invention.

Further provided herein are methods of repositioning a patient's teeth using one or more orthodontic appliances comprising polymeric materials described herein, e.g., as described in FIG. 4, and in some instances referred to "On-Track treatment." In some instances, provided herein is a method of repositioning a patient's teeth, the method comprising: generating a treatment plan for the patient, the plan comprising a plurality of intermediate tooth arrangements for moving teeth along a treatment path from an initial tooth arrangement toward a final tooth arrangement; producing a orthodontic appliance comprising a polymeric material of the present disclosure; and moving on-track, with the orthodontic appliance, at least one of the patient's teeth toward an intermediate tooth arrangement or the final tooth arrangement. In various cases, production of the orthodontic appliance comprises additive manufacturing.

The method of repositioning a patient's teeth can further comprise tracking progression of the patient's teeth along the treatment path after administration of the orthodontic appliance to the patient, the tracking comprising comparing a current arrangement of the patient's teeth to a planned arrangement of the patient's teeth. In such instances, greater than about 40%, 50%, 60%, or 70% of the patient's teeth can be on track with the treatment plan after 1, 2, 3, 4 or more weeks of treatment. In some cases, greater than 60% of the patient's teeth are on track with the treatment plan after 2 weeks of treatment. In some instances, an orthodontic used in such a method can have a retained repositioning force to the at least one of the patient's teeth after 2 days that is at least 10%, at least 20%, at least 30%, at least 40%, at least 50%, at least 60%, or at least 70% of repositioning force initially provided to the at least one of the patient's teeth.

Further referring to FIG. 4, a process 400 according to the present disclosure is illustrated. Individual aspects of the process are discussed in further detail below. The process includes receiving information regarding the orthodontic condition of the patient and/or treatment information (402), generating an assessment of the case (404), and generating a treatment plan for repositioning a patient's teeth (406). Briefly, a patient/treatment information will include obtaining data comprising an initial arrangement of the patient's teeth, which typically includes obtaining an impression or scan of the patient's teeth prior to the onset of treatment and can further include identification of one or more treatment goals selected by the practitioner and/or patient. A case assessment can be generated (404) so as to assess the complexity or difficulty of moving the particular patient's teeth in general or specifically corresponding to identified treatment goals and may further include practitioner experience and/or comfort level in administering the desired orthodontic treatment. In some cases, however, the assessment can include simply identifying particular treatment options (e.g., appointment planning, progress tracking, etc.) that are of interest to the patient and/or practitioner. The information and/or corresponding treatment plan will include identifying a final or target arrangement of the patient's teeth that is desired, as well as a plurality of planned successive or intermediary tooth arrangements for moving the teeth along a treatment path from the initial arrangement toward the selected final or target arrangement.

The process further includes generating customized treatment guidelines (408). The treatment plan typically includes multiple phases of treatment, with a customized set of treatment guidelines generated that correspond to a phase of the treatment plan. The guidelines will include detailed information on timing and/or content (e.g., specific tasks) to be completed during a given phase of treatment and will be of sufficient detail to guide a practitioner, including a less experienced practitioner or practitioner relatively new to the particular orthodontic treatment process, through the phase of treatment. Since the guidelines are designed to specifically correspond to the treatment plan and provide guidelines on activities specifically identified in the treatment information and/or generated treatment plan, the guidelines are said to be customized. The customized treatment guidelines are then provided to the practitioner so as to help instruct the practitioner as how to deliver a given phase of treatment. As set forth above, appliances can be generated based on the planned arrangements and will be provided to the practitioner and ultimately administered to the patient (410). The appliances are typically provided and/or administered in sets or batches of appliances, such as 2, 3, 4, 5, 6, 7, 8, 9, or more appliances, but are not limited to any particular administrative scheme. Appliances can be provided to the practitioner concurrently with a given set of guidelines, or appliances and guidelines can be provided separately.

After the treatment according to the plan begins and following administration of appliances to the patient, treatment progress tracking, e.g., by teeth matching, is done to assess a current and actual arrangement of the patient's teeth compared to a planned arrangement (412). If the patient's teeth are determined to be "on-track" and progressing according to the treatment plan, then treatment progresses as planned and treatment progresses to the next stage of treatment (414). If the patient's teeth have substantially reached the initially planned final arrangement, then treatment progresses to the final stages of treatment (414). Where the patient's teeth are determined to be tracking according to the treatment plan, but have not yet reached the final arrangement, the next set of appliances can be administered to the patient.

The threshold difference values of a planned position of teeth to actual positions selected as indicating that a patient's teeth have progressed on-track are provided below in TABLE 1. If a patient's teeth have progressed at or within the threshold values, the progress is considered to be on-track. If a patient's teeth have progressed beyond the threshold values, the progress is considered to be off-track.

TABLE 1

Exemplary On-Track Treatment

| Type Movement | Difference Actual/Planned |
|---|---|
| Rotations | |
| Upper Central Incisors | 9 degrees |
| Upper Lateral Incisors | 11 degrees |
| Lower Incisors | 11 degrees |
| Upper Cuspids | 11 degrees |
| Lower Cuspids | 9.25 degrees |
| Upper Bicuspids | 7.25 degrees |
| Lower First Bicuspid | 7.25 degrees |
| Lower Second Bicuspid | 7.25 degrees |
| Molars | 6 degrees |
| Extrusion | |
| Anterior | 0.75 mm |
| Posterior | 0.75 mm |
| Intrusion | |
| Anterior | 0.75 mm |
| Posterior | 0.75 mm |
| Angulation | |
| Anterior | 5.5 degrees |
| Posterior | 3.7 degrees |
| Inclination | |
| Anterior | 5.5 degrees |
| Posterior | 3.7 degrees |
| Translation | |
| BL Anterior | 0.7 mm |
| BL Posterior Cuspids | 0.9 mm |
| MD Anterior | 0.45 mm |
| MD Cuspids | 0.45 mm |
| MD Posterior | 0.5 mm |

The patient's teeth are determined to be on track by comparison of the teeth in their current positions with teeth in their expected or planned positions, and by confirming the teeth are within the parameter variance disclosed in TABLE 1. If the patient's teeth are determined to be on track, then treatment can progress according to the existing or original treatment plan. For example, a patient determined to be progressing on track can be administered one or more subsequent appliances according to the treatment plan, such as the next set of appliances. Treatment can progress to the final stages and/or can reach a point in the treatment plan where bite matching is repeated for a determination of whether a patient's teeth are progressing as planned or if the teeth are off track.

In some embodiments, as further disclosed herein, this disclosure provides methods of treating a patient using a 3D printed orthodontic appliance. In certain embodiments, the method of repositioning a patient's teeth (or, in some embodiments, a singular tooth) comprises: generating a treatment plan for the patient, the plan comprising tooth arrangements for moving teeth along a treatment path from an initial arrangement toward a final arrangement; producing a 3D printed orthodontic appliance comprising a polymeric material of the present disclosure; and moving on-track, with the orthodontic appliance, at least one of the patient's teeth toward an intermediate arrangement or a final tooth arrangement. In preferred embodiments, the method further comprises achieving on-track the movement of the patient's teeth to the intermediate arrangement or final tooth arrangement. In some embodiments, producing the 3D printed orthodontic appliance uses the photo-curable resins disclosed further herein. On-track performance can be determined, e.g., from TABLE 1, above.

In some embodiments, the method further comprises tracking the progression of the patient's teeth along the treatment path after administration of the orthodontic appliance. In certain embodiments, the tracking comprises comparing a current arrangement of the patient's teeth to a planned arrangement of the teeth. As a non-limiting example, following the initial administration of the orthodontic appliance, a period of time passes (e.g., two weeks), a comparison of the now-current arrangement of the patient's teeth (i.e., at two weeks of treatment) can be compared with the teeth arrangement of the treatment plan. In some embodiments, the progression can also be tracked by comparing the current arrangement of the patient's teeth with the initial configuration of the patient's teeth. The period of time can be, for example, greater than 3 days, greater than 4 days, greater than 5 days, greater than 6 days, greater than 7 days, greater than 8 days, greater than 9 days, greater than 10 days, greater than 11 days, greater than 12 days, greater than 13 days, greater than 2 weeks, greater than 3 weeks, greater than 4 weeks, or greater than 2 months. In some embodiments, the period of time can be from at least 3 days to at most 4 weeks, from at least 3 days to at most 3 weeks, from at least 3 days to at most 2 weeks, from at least 4 days to at most 4 weeks, from at least 4 days to at most 3 weeks, or from at least 4 days to at most 2 weeks. In certain embodiments, the period of time can restart following the administration of a new orthodontic appliance.

In some embodiments, greater than 50%, greater than 55%, greater than 60%, greater than 65%, greater than 70%, greater than 75%, greater than 80%, greater than 85%, greater than 90%, greater than 91%, greater than 92%, greater than 93%, greater than 94%, greater than 95%, greater than 96%, greater than 97%, greater than 98%, or greater than 99% of the patient's teeth are on track with the treatment plan after a period of time of using an orthodontic appliance as disclosed further herein. In some embodiments, the period of time is 3 days, 4 days, 5 days, 6 days, 7 days, 8 days, 9 days, 10 days, 11 days, 12 days, 13 days, 2 weeks, 3 weeks, 4 weeks, or greater than 4 weeks.

In some embodiments of the method disclosed above, the 3D printed orthodontic appliance has a retained repositioning force (i.e., the repositioning force after the orthodontic appliance has been applied to or worn by the patient over a period of time), and the retained repositioning force to at least one of the patient's teeth after the period of time is at least 10%, at least 20%, at least 30%, at least 40%, at least 50%, at least 55%, at least 60%, at least 65%, at least 70%, at least 75%, at least 80%, at least 85%, at least 90%, at least 95%, at least 96%, at least 97%, at least 98%, or at least 99% of the repositioning force initially provided to the at least one of the patient's teeth (i.e., with initial application of the orthodontic appliance). In some embodiments, the period of time is 3 days, 4 days, 5 days, 6 days, 7 days, 8 days, 9 days, 10 days, 11 days, 12 days, 13 days, 2 weeks, 3 weeks, 4 weeks, or greater than 4 weeks.

In preferred embodiments, the orthodontic appliances disclosed herein can provide on-track movement of at least one of the patient's teeth. On-track movement has been described further herein, e.g., at TABLE 1. In some embodiments, the orthodontic appliances disclosed herein can be used to achieve on-track movement of at least one of the patient's teeth to an intermediate tooth arrangement. In some embodiments, the orthodontic appliances disclosed herein can be used to achieve on-track movement of at least one of the patient's teeth to a final tooth arrangement.

In some embodiments, prior to moving on-track, with the orthodontic appliance, at least one of the patient's teeth toward the intermediate arrangement or the final tooth arrangement, the orthodontic appliance comprises a first flexural stress; and after achieving on-track the movement of the at least one of the patient's teeth to the intermediate arrangement or the final tooth arrangement, the orthodontic appliance comprises a second flexural stress.

As provided herein, the methods disclosed can use the orthodontic appliances further disclosed herein. Said orthodontic appliances can be directly fabricated using, e.g., the resins disclosed herein. In certain embodiments, the direct fabrication comprises cross-linking the resin.

The appliances formed from the resins disclosed herein provide improved durability, strength, and flexibility, which in turn improve the rate of on-track progression in treatment plans. In some embodiments, greater than 60%, greater than 70%, greater than 80%, greater than 90%, or greater than 95% of patients treated with the orthodontic appliances disclosed herein (e.g., an aligner) are classified as on-track in a given treatment stage. In certain embodiments, greater than 60%, greater than 70%, greater than 80%, greater than 90%, or greater than 95% of patients treated with the orthodontic appliances disclosed herein (e.g., an aligner) have greater than 50%, greater than 55%, greater than 60%, greater than 65%, greater than 70%, greater than 75%, greater than 80%, greater than 85%, greater than 90%, or greater than 95% of their tooth movements classified as on-track.

Experimental Methods

In some embodiments, the stress relaxation of a material or device can be measured by monitoring the time-dependent stress resulting from a steady strain. The extent of stress relaxation can also depend on the temperature, relative humidity and other applicable conditions (e.g., presence of water). In embodiments, the test conditions for stress relaxation are a temperature of 37±2° C. at 100% relative humidity or a temperature of 37±2° C. in water.

The dynamic viscosity of a fluid indicates its resistance to shearing flows. The SI unit for dynamic viscosity is the Poiseuille (Pa·s). Dynamic viscosity is commonly given in units of centipoise, where 1 centipoise (cP) is equivalent to 1 mPa·s. Kinematic viscosity is the ratio of the dynamic viscosity to the density of the fluid; the SI unit is $m^2/s$. Devices for measuring viscosity include viscometers and rheometers.

Figure 5:
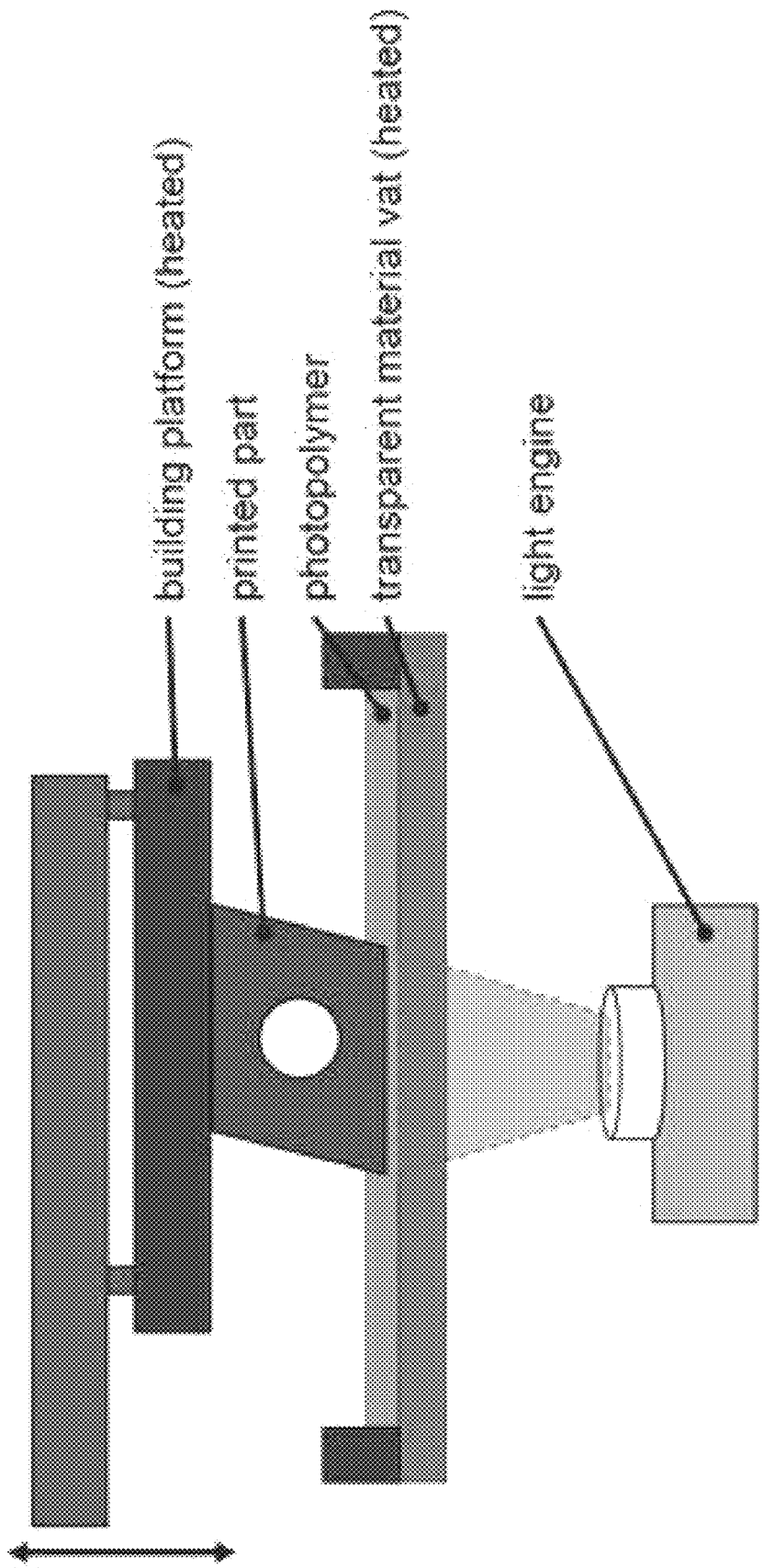
FIG. 5 shows a schematic configuration of a high temperature additive manufacturing device used for curing a curable compositions of the present disclosure by using a 3D printing process.

Additive manufacturing or 3D printing processes for generating a device herein (e.g., an orthodontic appliance) can be conducted using a Hot Lithography apparatus prototype from Cubicure (Vienna, Austria), which can substantially be configured as schematically shown in FIG. 5. In such cases, a photo-curable composition (e.g., resin) according to the present disclosure can be filled into the transparent material vat of the apparatus shown in FIG. 5, which vat can be heated to 90-110° C. The building platform can be heated to 90-110° C., too, and lowered to establish holohedral contact with the upper surface of the curable composition. By irradiating the composition with 375 nm UV radiation using a diode laser from Soliton, which can have an output power of 70 mW, which can be controlled to trace a predefined prototype design, and alternately raising the building platform, the composition can be cured layer by layer by a photopolymerization process according to the disclosure, resulting in a polymeric material according to present disclosure.

VII. Experimental Methods

All chemicals were purchased from commercial sources and were used without further purification, unless otherwise stated.

$^1$H NMR and $^{13}$C NMR spectra were recorded on a BRUKER AC-E-200 FT-NMR spectrometer or a BRUKER Avance DRX-400 FT-NMR spectrometer. The chemical shifts are reported in ppm (s: singlet, d: doublet, t: triplet, q: quartet, m: multiplet). The solvents used were deuterated chloroform ($CDCl_3$, 99.5% deuteration) and deuterated DMSO ($d_6$-DMSO, 99.8% deuteration).

In some embodiments, the stress relaxation of a material or device can be measured by monitoring the time-dependent stress resulting from a steady strain. The extent of stress relaxation can also depend on the temperature, relative humidity and other applicable conditions (e.g., presence of water). In embodiments, the test conditions for stress relaxation are a temperature of 37±2° C. at 100% relative humidity or a temperature of 37±2° C. in water.

The dynamic viscosity of a fluid indicates its resistance to shearing flows. The SI unit for dynamic viscosity is the Poiseuille (Pa·s). Dynamic viscosity is commonly given in units of centipoise, where 1 centipoise (cP) is equivalent to 1 mPa·s. Kinematic viscosity is the ratio of the dynamic viscosity to the density of the fluid; the SI unit is $m^2/s$. Devices for measuring viscosity include viscometers and rheometers. For example, an MCR 301 rheometer from Anton Paar may be used for rheological measurement in rotation mode (PP-25, 50 s-1, 50-115° C., 3° C./min).

Determining the water content when fully saturated at use temperature can comprise exposing the polymeric material to 100% humidity at the use temperature (e.g., 40° C.) for a period of 24 hours, then determining water content by methods known in the art, such as by weight.

In some embodiments, the presence of a crystalline phase and an amorphous phase provide favorable material properties to the polymeric materials. Property values of the cured polymeric materials can be determined, for example, by using the following methods:

flexural modulus, remaining flexural stress, and stress relaxation properties can be assessed using an RSA-G2 instrument from TA Instruments, with a 3-point bending, according to ASTM D790; for example, stress relaxation can be measured at 30° C. and submerged in water, and reported as the remaining load after 24 hours, as either the percent (%) of initial load, and/or in MPa;

storage modulus can be measured at 37° C. and is reported in MPa;

$T_g$ of the cured polymeric material can be assessed using dynamic mechanical analysis (DMA) and is provided herein as the tan δ peak;

tensile modulus, tensile strength, elongation at yield and elongation at break can be assessed according to ISO 527-2 5B; and tensile strength at yield, elongation at break, tensile strength, and Young's modulus can be assessed according to ASTM D1708;

molecular weight can be measured by size exclusion chromatography or gel permeation chromatography.

Additive manufacturing or 3D printing processes for generating a device herein (e.g., an orthodontic appliance) can be conducted using a Hot Lithography apparatus prototype from Cubicure (Vienna, Austria), which can substantially be configured as schematically shown in FIG. 5. In such cases, a photo-curable composition (e.g., resin) according to the present disclosure can be filled into the transparent material vat of the apparatus shown in FIG. 5, which vat can be heated to 90-110° C. The building platform can be heated to 90-110° C., too, and lowered to establish holohedral contact with the upper surface of the curable composition. By irradiating the composition with 375 nm UV radiation using a diode laser from Soliton, which can have an output power of 70 mW, which can be controlled to trace a predefined prototype design, and alternately raising the building platform, the composition can be cured layer by layer by a photopolymerization process according to the disclosure, resulting in a polymeric material according to present disclosure.

EXAMPLES

The following examples are given for the purpose of illustrating various embodiments of the invention and are not meant to limit the present disclosure in any fashion. The present examples, along with the methods described herein are presently representative of some embodiments, are exemplary, and are not intended as limitations on the scope of the invention. Changes therein and other uses which are encompassed within the spirit of the invention as defined by the scope of the claims will occur to those skilled in the art.

Example 1

Preparation of Poly-(Isobornyl Acrylate) [2, HO—PIBOA-Br]

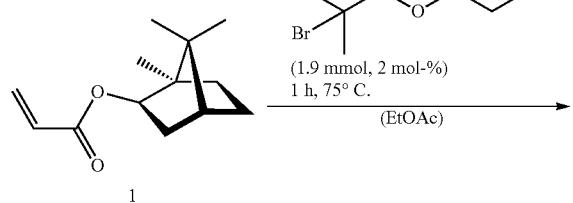

This example describes the synthesis of a polymer 2 that is a precursor to a photo-polymerizable polymer as described herein.

To a 100-mL schlenk flask equipped with a magnetic stir bar were added isobornyl acrylate (20.0 mL, 94.9 mmol), ethyl acetate (20 mL), and pentamethyldiethylenetriamine (PMDETA) (297 uL, 1.42 mmol). The mixture was sparged with nitrogen for 1 h. Then, copper(I) bromide (CuBr) (136 mg, 0.949 mmol) was added to the flask and the mixture heated at 75° C. with stirring. 2-Hydroxylethyl 2-bromoisobutyrate (275 uL, 1.90 mmol) in ethyl acetate (1 mL) was injected to the flask to begin the reaction. After 1 h at 75° C., the reaction was quenched by cooling the flask in an ice-water bath, opening the flask to atmosphere, and adding dichloromethane. The mixture was passed through neutral alumina using dichloromethane to remove the copper catalyst and precipitated in methanol to remove unreacted monomer, yielding poly(isobornyl acrylate) with terminal hydroxyl and bromine end groups, HO—PIBOA-Br (2).

Example 2

Preparation of Poly-(Isobornyl Acrylate) with Terminal Hydroxy Groups [3, HO—PIBOA-OH]

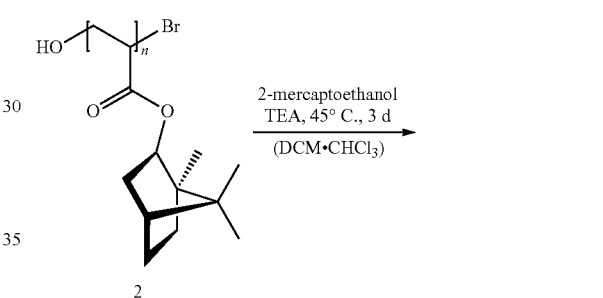

The previously synthesized polymer HO—PIBOA-Br (2) was stirred with TEA (6 equiv per chain) and triethylamine (6 equiv) in dimethylformamide/chloroform at 45° C. for 3 days to obtain dihydroxyl-terminated HO—PIBOA-OH (3).

Alternative routes towards HO—PIBOA-OH (3) include reacting HO—PIBOA-Br (2) first with acrylic acid and 1,8-diazabicycloundec-7-ene to install an acrylate group in place of the bromine, or atom transfer radical coupling of HO—PIBOA-Br in the presence of styrene, which promotes faster coupling. For the latter approach, a mixture of 1:1:2:4:1-5 [HO—PIBOA-Br]$_0$:[CuBr]$_0$:-[PMDETA]$_0$:[Cu$^0$]$_{90}$ in toluene is stirred at 70° C. for several hours to achieve high (≥0.90) coupling efficiency.

Example 3

Preparation of Diacryloyl-Terminated and Di(Meth)Acryloyl-Terminated Poly-(Isobornyl Acrylate)—Photopolymerizable Telechelic Polymers (4, 5)

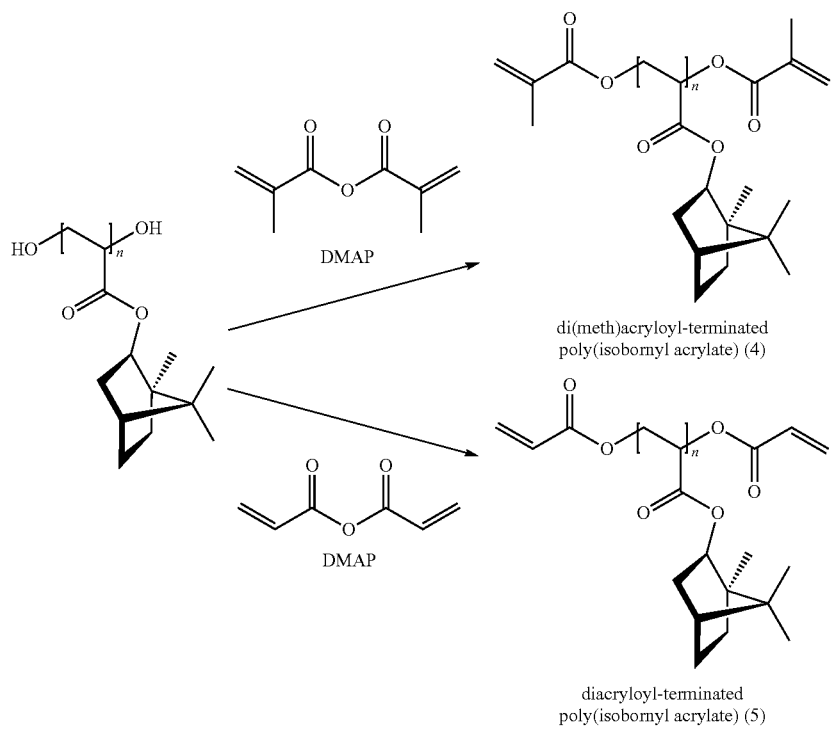

di(meth)acryloyl-terminated poly(isobornyl acrylate) (4)

diacryloyl-terminated poly(isobornyl acrylate) (5)

HO—PIBOA-OH (3) was then reacted with (meth)acrylic anhydride and 4-dimethylaminopyridine to obtain di(meth)acryloyl-terminated poly(isobornyl acrylate) (4), and acrylic anhydride and 4-dimethylaminopyridine obtain the telechelic polymer diacryloyl-terminated poly(isobornyl acrylate) (5).

Example 4

Formation of Polymeric Materials from Photo-Curable Resins

This example describes the generation of photo-curable resins comprising one or more telechelic polymers and/or telechelic block copolymers described herein, and the formation of polymeric materials from the photo-curable resins. Also described are exemplary materials properties from the polymeric materials.

A photo-curable resins is generated by combining about 70 wt % of a telechelic block copolymer (e.g., compound 5) and 30 wt % of a reactive diluent comprising photoreactive end groups. The photoreactive end groups of the polymerizable components of this resin are acrylate or methacrylate moieties that can comprise various substituents as described herein.

Example 5

Direct Fabrication of Polymeric Materials from Photo-Curable Resins

This example describes the direct fabrication of polymeric materials from photo-curable resins as described herein, e.g., in EXAMPLE 4.

Printed parts are obtained using an Asiga digital light projection (DLP) printer. The photo-curable resin from EXAMPLE 4 is introduced to the DLP printer, and cured polymeric material is obtained in specified shapes. The photo-curable low-viscosity resins are compatible with use of conventional 3D printers, and the cured polymeric materials have good mechanical properties.

Example 6

Treatment Using an Orthodontic Appliance

This example describes the use of a directly 3D printed orthodontic appliance to move a patient's teeth according to a treatment plan. This example also describes the characteristics that the orthodontic appliance can have following its use, in contrast to its characteristics prior to use.

A patient in need of, or desirous of, a therapeutic treatment to rearrange at least one tooth has their teeth arrangement assessed. An orthodontic treatment plan is generated for the patient. The orthodontic treatment plan comprises a plurality of intermediate tooth arrangements for moving teeth along a treatment path, from the initial arrangement (e.g., that which was initially assessed) toward a final arrangement. The treatment plan includes the use of an orthodontic appliance, fabricated using photo-curable resins and methods disclosed further herein, to provide orthodontic appliances having low levels of hydrogen bonding units. In some embodiments, a plurality of orthodontic appliances is used, each of which can be fabricated using the photo-curable resins and methods disclosed further herein.

The orthodontic appliances are provided, and iteratively applied to the patient's teeth to move the teeth through each of the intermediate tooth arrangements toward the final arrangement. The patient's tooth movement is tracked. A comparison is made between the patient's actual teeth arrangement and the planned intermediate arrangement. Where the patient's teeth are determined to be tracking according to the treatment plan, but have not yet reached the final arrangement, the next set of appliances can be administered to the patient. The threshold difference values of a planned position of teeth to actual positions selected as indicating that a patient's teeth have progressed on-track are provided above in TABLE 1. If a patient's teeth have progressed at or within the threshold values, the progress is considered to be on-track. Favorably, the use of the appliances disclosed herein increases the probability of on-track tooth movement.

The assessment and determination of whether treatment is on-track can be conducted, for example, 1 week (7 days) following the initial application of an orthodontic appliance. Following this period of application, additional parameters relating to assessing the durability of the orthodontic appliance can also be conducted. For example, relative repositioning force (compared to that which was initially provided by the appliance), remaining flexural stress, relative flexural modulus, and relative elongation at break can be determined.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by some embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

What is claimed is:

1. A photo-curable resin comprising:
a telechelic polymer, the telechelic polymer comprising a polymer chain including, in a polymerized form, a first monomer and a reactive end functional group located at each terminus of the polymer chain; and
a reactive diluent,
wherein the first monomer comprises a first reactive functional group and has a vapor pressure from 2 Pa to 10 Pa at 60° C. in its monomeric state,
wherein the following conditions are met:
(i) following 2 h heating at 90° C., the first monomer has a mass loss rate of less than 0.25% per hour at 90° C. in its monomeric state;
(ii) a number average molecular weight of the telechelic polymer is not more than 50 kDa; and
(iii) the reactive end functional group and the first reactive functional group independently comprise a photopolymerizable moiety, and
wherein the photo-curable resin is capable of being 3D printed to form an article.

2. The photo-curable resin of claim 1, wherein the first monomer has a vapor pressure from 2 Pa to 5 Pa at 60° C. in its monomeric state.

3. The photo-curable resin of claim 1, wherein following the 2 h heating at 90° C., the first monomer has a mass loss from 0.05% to 0.225% per hour at 90° C. in its monomeric state.

4. The photo-curable resin of claim 1, wherein following the 2 h heating at 90° C., the first monomer has a mass loss rate from 0.025% to 0.125% at 90° ° C. in its monomeric state.

5. The photo-curable resin of claim 1, wherein the number average molecular weight of the telechelic polymer is from 5 kDa to 40 kDa.

6. The photo-curable resin of claim 5, wherein the number average molecular weight of the telechelic polymer is from 5 kDa to 30 kDa.

7. The photo-curable resin of claim 5, wherein the number average molecular weight of the telechelic polymer is from 5 kDa to 20 kDa.

8. The photo-curable resin of claim 5, wherein the number average molecular weight of the telechelic polymer is from 5 kDa to 15 kDa.

9. The photo-curable resin of claim 1, wherein the photopolymerizable moiety comprises an acrylate, methacrylate, vinyl acrylate, vinyl methacrylate, allyl ether, silene, alkyne, alkene, vinyl ether, maleimide, fumarate, maleate, itoconate, styrenyl, epoxide, oxetane, or thiol moiety.

10. The photo-curable resin of claim 1, wherein the photopolymerizable moiety comprises an acrylate or methacrylate moiety.

11. The photo-curable resin of claim 1, wherein the photopolymerizable moiety is capable of undergoing a photo-induced Diels-Alder click reaction or a photodimerization reaction.

12. The photo-curable resin of claim 1, wherein the first monomer has a melting point of at least 25° C. when in its monomeric state.

13. The photo-curable resin of claim 1, wherein the first monomer is a compound according to Formula (I):

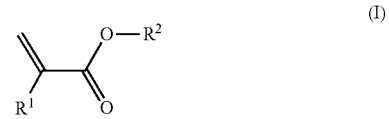

wherein,
$R^1$ is H, substituted or unsubstituted $C_{1-3}$ alkyl or halogen; and
$R^2$ is substituted or unsubstituted $C_{1-6}$ alkyl, substituted or unsubstituted $C_{1-6}$ heteroalkyl, substituted or unsubstituted $C_{1-6}$ carbonyl, substituted or unsubstituted $C_{1-6}$ carboxy, substituted or unsubstituted aryl, substituted or unsubstituted heteroaryl, substituted or unsubstituted cyclo($C_{3-8}$) alkyl, or substituted or unsubstituted cyclo ($C_{3-8}$) heteroalkyl.

14. The photo-curable resin of claim 1, comprising less than 20 wt % hydrogen bonding units.

15. The photo-curable resin of claim 1, further comprising a crosslinking modifier, a light blocker, a solvent, a glass transition temperature modifier, or a combination thereof.

16. A medical device comprising a polymeric material formed from the photo-curable resin of claim 1.

17. The photo-curable resin of claim 1, wherein the telechelic polymer is a compound according to Formula (IV):

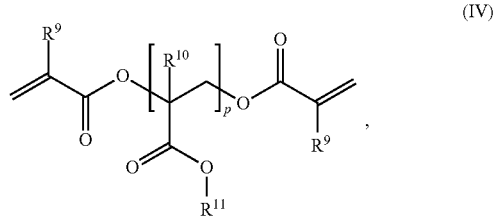

(IV)

wherein:
each instance of $R^9$ is H, substituted or unsubstituted $C_{1-3}$ alkyl, or halogen;
each instance of $R^{10}$ is H, substituted or unsubstituted $C_{1-3}$ alkyl, or halogen;
$R^{11}$ is substituted or unsubstituted bicyclic alkyl; and
p is a positive integer from 1 to 200.

18. The photo-curable resin of claim 17, wherein $R^{11}$ is selected from the group consisting of:

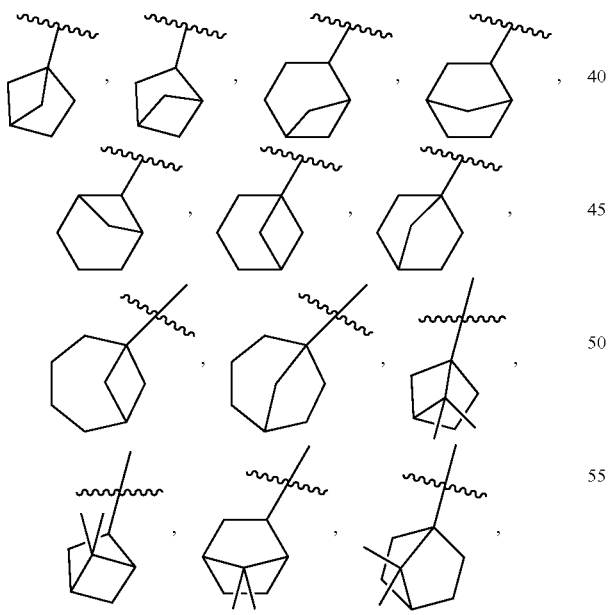

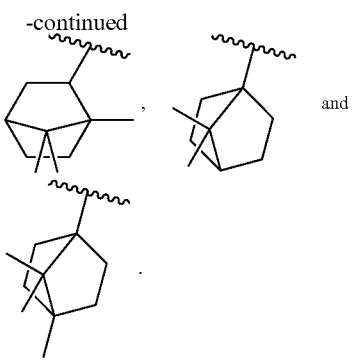

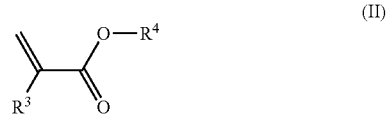

and.

19. The photo-curable resin of claim 13, further comprising another telechelic polymer, the another telechelic polymer comprising a polymer chain including, in a polymerized form, a second monomer that is different from the first monomer and a reactive end functional group located at each terminus of the polymer chain, wherein the second monomer is a compound according to Formula (II):

$$\text{(II)}$$

wherein,
$R^3$ is H, substituted or unsubstituted $C_{1-3}$ alkyl or halogen; and
$R^4$ is substituted or unsubstituted $C_{1-6}$ alkyl, substituted or unsubstituted $C_{1-6}$ heteroalkyl, substituted or unsubstituted $C_{1-6}$ carbonyl, substituted or unsubstituted $C_{1-6}$ carboxy, substituted or unsubstituted aryl, substituted or unsubstituted heteroaryl, substituted or unsubstituted cyclo($C_{3-8}$) alkyl, or substituted or unsubstituted cyclo ($C_{3-8}$) heteroalkyl.

20. The photo-curable resin of claim 1, wherein the polymer chain of the telechelic polymer further comprises, in a polymerized form, a second monomer different from the first monomer, wherein the second monomer has a vapor pressure from 2 Pa to 10 Pa at 60° C. in its monomeric state, and following the 2 h heating at 90° C., the second monomer has a mass loss rate from 0.05% to 0.225% per hour at 90° ° C. in its monomeric state, wherein the first monomer, in the polymerized form, constitutes a first block of the polymer chain and the second monomer, in the polymerized form, constitutes a second block of the polymer chain.

21. The photo-curable resin of claim 1, wherein the article comprises an orthodontic appliance.

22. The photo-curable resin of claim 21, wherein the orthodontic appliance comprises a dental aligner of a series of dental aligners, an incremental palatal expander of a series of incremental palatal expanders or a retainer.

* * * * *